US011447775B2

(12) United States Patent
Olson et al.

(10) Patent No.: US 11,447,775 B2
(45) Date of Patent: *Sep. 20, 2022

(54) ANTISENSE OLIGONUCLEOTIDES TARGETING ALPHA-SYNUCLEIN AND USES THEREOF

(71) Applicants: Bristol-Myers Squibb Company, Princeton, NJ (US); Roche Innovation Center Copenhagen A/S, Hørsholm (DK)

(72) Inventors: Richard E. Olson, Cambridge, MA (US); Angela M. Cacace, Haddam Neck, CT (US); Jere E. Meredith, Jr., Haddam, CT (US); Nino Devidze, Conshohocken, PA (US); James K. Loy, Gales Ferry, CT (US); Carl J. Baldick, Pennington, NJ (US); Annapurna Pendri, South Glastonbury, CT (US); Ivar M. McDonald, Woodstock, CT (US); Peter Hagedorn, Hørsholm (DK); Marianne Lerbech Jensen, Køge (DK)

(73) Assignees: Bristol-Myers Squibb Company, Princeton, NJ (US); Roche Innovation Center Copenhagen A/S, Hørsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/961,624

(22) PCT Filed: Jan. 11, 2019

(86) PCT No.: PCT/US2019/013249
§ 371 (c)(1),
(2) Date: Jul. 10, 2020

(87) PCT Pub. No.: WO2019/140231
PCT Pub. Date: Jul. 18, 2019

(65) Prior Publication Data
US 2020/0354720 A1 Nov. 12, 2020

Related U.S. Application Data

(60) Provisional application No. 62/616,937, filed on Jan. 12, 2018.

(51) Int. Cl.
C07H 21/04 (2006.01)
C12N 15/113 (2010.01)

(52) U.S. Cl.
CPC ........ *C12N 15/113* (2013.01); *C12N 2310/11* (2013.01); *C12N 2310/315* (2013.01); *C12N 2310/3231* (2013.01); *C12N 2310/351* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Dinh et al. |
| 5,102,785 A | 4/1992 | Livak et al. |
| 5,130,302 A | 7/1992 | Spielvogel et al. |
| 5,175,273 A | 12/1992 | Bischofberger et al. |
| 5,367,066 A | 11/1994 | Urdea et al. |
| 5,432,272 A | 7/1995 | Benner |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,587,469 A | 12/1996 | Cook et al. |
| 5,594,121 A | 1/1997 | Froehler et al. |
| 5,596,091 A | 1/1997 | Switzer |
| 5,681,941 A | 10/1997 | Cook et al. |
| 5,750,692 A | 5/1998 | Cook et al. |
| 5,840,708 A | 11/1998 | Weiss |
| 5,932,557 A | 8/1999 | Mustafa et al. |
| 5,981,279 A | 11/1999 | Weiss |
| 6,025,193 A | 2/2000 | Weiss |
| 6,268,490 B1 | 7/2001 | Imanishi et al. |
| 6,277,640 B1 | 8/2001 | Bennett et al. |
| 6,455,308 B1 | 9/2002 | Freier |
| 6,525,191 B1 | 2/2003 | Ramasamy |
| 6,599,718 B1 | 7/2003 | Liu et al. |
| 6,670,461 B1 | 12/2003 | Wengel et al. |
| 6,770,748 B2 | 8/2004 | Imanishi et al. |
| 6,794,499 B2 | 9/2004 | Wengel et al. |

(Continued)

FOREIGN PATENT DOCUMENTS

CA 2817960 C 6/2020
EP 0673252 A1 9/1995

(Continued)

OTHER PUBLICATIONS

Abeliovich, A. et al., "Mice lacking α-synuclein display functional deficits in the nigrostriatal dopamine system," *Neuron*, 25: 239-252, Elsevier, Inc., Netherlands (2000).

Akinc, A., et al., "A combinatorial library of lipid-like materials for delivery of RNAi therapeutics," *Nature Biotechnology*, 26(5):561-569, Springer Nature Limited, Germany (2008).

Alarcon-Aris D., et al., "Selective α-Synuclein Knockdown in Monoamine Neurons by Intranasal Oligonucleotide Delivery: Potential Therapy for Parkinson's Disease," Molecular Therapy, 26(2):550-567, Cell Press, Cambridge. (Feb. 2018).

Albaek, N. et al., "Analogues of a Locked Nucleic Acid with Three-Carbon 2',4'-Linkages: Synthesis by Ring-Closing Metathesis and Influence on Nucleic Acid Duplex Stability and Structure," *J Org Chem.*, 71(20): 7731-7740, Supplemental Information, American Chemical Society, United States (2006).

(Continued)

*Primary Examiner* — Kimberly Chong
(74) *Attorney, Agent, or Firm* — Sterne, Kessler, Goldstein & Fox P.L.L.C.

(57) ABSTRACT

The present disclosure relates to antisense oligonucleotides, which target SNCA mRNA (e.g., at an intron exon junction) in a cell, leading to reduced expression of SNCA protein. Reduction of SNCA protein expression is beneficial for the treatment of certain medical disorders, e.g., a neurological disorder.

20 Claims, 16 Drawing Sheets

Specification includes a Sequence Listing.

(56) References Cited

U.S. PATENT DOCUMENTS

| | | |
|---|---|---|
| 6,833,361 B2 | 12/2004 | Hong et al. |
| 6,890,535 B1 | 5/2005 | Schenk |
| 7,034,133 B2 | 4/2006 | Wengel et al. |
| 7,053,207 B2 | 5/2006 | Wengel |
| 7,101,993 B1 | 9/2006 | Cook et al. |
| 7,399,845 B2 | 7/2008 | Seth et al. |
| 7,414,034 B2 | 8/2008 | Schneider |
| 7,427,672 B2 | 9/2008 | Imanishi et al. |
| 7,595,306 B2 | 9/2009 | Bumcrot et al. |
| 7,691,563 B2 | 4/2010 | Michaelis et al. |
| 7,705,016 B2 | 4/2010 | Rossei et al. |
| 7,727,957 B2 | 6/2010 | Schenk et al. |
| 7,750,141 B2 | 7/2010 | Crooke et al. |
| 7,763,747 B2 | 7/2010 | Snow et al. |
| 7,776,538 B2 | 8/2010 | Nitta et al. |
| 7,838,657 B2 | 11/2010 | Singh et al. |
| 8,012,116 B2 | 9/2011 | Del Bigio et al. |
| 8,022,045 B1 | 9/2011 | Bogdahan et al. |
| 8,110,560 B2 | 2/2012 | Singh et al. |
| 8,283,334 B2 | 10/2012 | Bogdahan et al. |
| 8,361,977 B2 | 1/2013 | Baker et al. |
| 8,580,756 B2 | 11/2013 | Hansen et al. |
| 8,703,728 B2 | 4/2014 | Swayze et al. |
| 8,980,853 B2 | 3/2015 | Bennett et al. |
| 9,193,969 B2 | 11/2015 | Montefeltro et al. |
| 9,271,992 B2 | 3/2016 | Michaelis et al. |
| 9,492,415 B2 | 11/2016 | Bankiewicz et al. |
| 9,605,263 B2 | 3/2017 | Rigo |
| 9,663,783 B2 | 5/2017 | Freier |
| 9,701,708 B2 | 7/2017 | Cedillo et al. |
| 9,717,750 B2 | 8/2017 | Bennett et al. |
| 9,803,200 B2 | 10/2017 | Henshall et al. |
| 9,872,900 B2 | 1/2018 | Ciaramella et al. |
| 9,925,277 B2 | 3/2018 | Almarsson et al. |
| 9,926,559 B2 | 3/2018 | Bennett et al. |
| 9,994,850 B2 | 6/2018 | Christensen et al. |
| 10,022,435 B2 | 7/2018 | Ciaramella et al. |
| 10,023,626 B2 | 7/2018 | Bolen et al. |
| 10,138,482 B2 | 11/2018 | Rigo |
| 10,221,414 B2 | 3/2019 | Freier et al. |
| 10,258,698 B2 | 4/2019 | Hog et al. |
| 10,266,822 B2 | 4/2019 | Singh et al. |
| 10,323,076 B2 | 6/2019 | Ellsworth et al. |
| 10,407,680 B2 | 9/2019 | Kordasiewicz |
| 10,436,802 B2 | 10/2019 | Rigo et al. |
| 10,479,995 B2 | 11/2019 | Vargeese et al. |
| 10,709,779 B2 | 7/2020 | Ciaramella et al. |
| 10,724,035 B2 | 7/2020 | Vargeese et al. |
| 10,815,480 B2 | 10/2020 | Freier |
| 11,359,197 B2 | 6/2022 | Olson et al. |
| 2003/0032791 A1 | 2/2003 | Alan et al. |
| 2003/0060436 A1 | 3/2003 | Schneider |
| 2003/0060438 A1 | 3/2003 | Henry et al. |
| 2003/0143738 A1 | 7/2003 | Yokata |
| 2004/0171570 A1 | 9/2004 | Allerson et al. |
| 2004/0226056 A1 | 11/2004 | Roch et al. |
| 2004/0241651 A1 | 12/2004 | Olek et al. |
| 2005/0014689 A1 | 1/2005 | Sugaru et al. |
| 2005/0019320 A1 | 1/2005 | Sugaru et al. |
| 2005/0020530 A1 | 1/2005 | Schneider |
| 2005/0032695 A1 | 2/2005 | Michaelis et al. |
| 2005/0032744 A1 | 2/2005 | Michaelis et al. |
| 2005/0064548 A1 | 3/2005 | Lindquist et al. |
| 2005/0130923 A1 | 6/2005 | Bhat et al. |
| 2007/0161595 A1 | 7/2007 | Bumcrot et al. |
| 2007/0213366 A1 | 9/2007 | Justman et al. |
| 2007/0225209 A1 | 9/2007 | Roch et al. |
| 2007/0287831 A1 | 12/2007 | Seth et al. |
| 2008/0003570 A1 | 1/2008 | Rogers et al. |
| 2008/0039418 A1 | 2/2008 | Freier |
| 2008/0039618 A1 | 2/2008 | Allerson et al. |
| 2008/0206253 A1 | 8/2008 | Hua et al. |
| 2008/0300204 A1 | 12/2008 | Federoff et al. |
| 2008/0306143 A1 | 12/2008 | Choi et al. |
| 2009/0012281 A1 | 1/2009 | Swayze et al. |
| 2009/0092981 A1 | 4/2009 | Swayze et al. |
| 2009/0123575 A1 | 5/2009 | Lake et al. |
| 2009/0155778 A1 | 6/2009 | Niita et al. |
| 2009/0176729 A1 | 7/2009 | Tan |
| 2009/0286745 A1 | 11/2009 | Zurdo et al. |
| 2009/0306190 A1 | 12/2009 | Stenzel-Poore et al. |
| 2010/0031377 A1 | 2/2010 | Schenk et al. |
| 2010/0036122 A1 | 2/2010 | Suh |
| 2010/0056622 A1 | 3/2010 | Lauterbach |
| 2010/0137257 A1 | 6/2010 | Michaelis et al. |
| 2010/0151520 A1 | 6/2010 | Rogers et al. |
| 2010/0179223 A1 | 7/2010 | Esposito et al. |
| 2010/0204306 A1 | 8/2010 | Tan |
| 2010/0261753 A1 | 10/2010 | Boyd et al. |
| 2010/0278814 A1 | 11/2010 | Schenk et al. |
| 2011/0009445 A1 | 1/2011 | Stenzel-Poore et al. |
| 2011/0105405 A1 | 5/2011 | Michaelis et al. |
| 2011/0130441 A1 | 6/2011 | Seth et al. |
| 2011/0263678 A1 | 10/2011 | Bogdahn et al. |
| 2012/0322851 A1 | 12/2012 | Hardee et al. |
| 2014/0005252 A1 | 1/2014 | Bennett et al. |
| 2014/0235696 A1 | 8/2014 | Henshall et al. |
| 2016/0002627 A1 | 1/2016 | Bennett et al. |
| 2016/0038612 A1 | 2/2016 | Hoge et al. |
| 2016/0194368 A1 | 7/2016 | Hoge et al. |
| 2016/0194625 A1 | 7/2016 | Hoge et al. |
| 2016/0235856 A1 | 8/2016 | Montefeltro et al. |
| 2016/0243221 A1 | 8/2016 | Hoge et al. |
| 2016/0243259 A1 | 8/2016 | Örn et al. |
| 2016/0244501 A1 | 8/2016 | Ellsworth et al. |
| 2016/0244502 A1 | 8/2016 | Bolen et al. |
| 2016/0251655 A1 | 9/2016 | Freier et al. |
| 2016/0304871 A1 | 10/2016 | Frank |
| 2016/0317647 A1 | 11/2016 | Ciaramella et al. |
| 2016/0331828 A1 | 11/2016 | Ciaramella et al. |
| 2016/0369270 A1 | 12/2016 | Henshall et al. |
| 2017/0002060 A1 | 1/2017 | Bolen et al. |
| 2017/0173128 A1 | 6/2017 | Hoge et al. |
| 2017/0349897 A1 | 12/2017 | Frank |
| 2018/0073022 A1 | 3/2018 | Freier |
| 2018/0085391 A1 | 3/2018 | Bouchon et al. |
| 2018/0092992 A1 | 4/2018 | Harley et al. |
| 2018/0119145 A1 | 5/2018 | Kordasiewicz |
| 2018/0208925 A1 | 7/2018 | Henshall et al. |
| 2018/0214579 A1 | 8/2018 | Örn et al. |
| 2018/0216108 A1 | 8/2018 | Vargeese et al. |
| 2019/0000959 A1 | 1/2019 | Ciaramella et al. |
| 2019/0008886 A1 | 1/2019 | Nakamori et al. |
| 2019/0008948 A1 | 1/2019 | Ciaramella et al. |
| 2019/0015501 A1 | 1/2019 | Ciaramella et al. |
| 2019/0016781 A1 | 1/2019 | Bolen et al. |
| 2019/0142971 A1 | 5/2019 | Hoge et al. |
| 2019/0192653 A1 | 6/2019 | Hoge et al. |
| 2019/0211332 A1 | 7/2019 | Kordasiewicz |
| 2019/0224339 A1 | 7/2019 | Paul et al. |
| 2019/0248864 A1 | 8/2019 | Ellsworth et al. |
| 2019/0264204 A1 | 8/2019 | Rigo |
| 2019/0270990 A1 | 9/2019 | Kordasiewicz et al. |
| 2019/0367916 A1 | 12/2019 | Freier et al. |
| 2020/0056173 A1 | 2/2020 | Vargeese et al. |
| 2020/0056179 A1 | 2/2020 | Freier et al. |
| 2020/0080083 A1 | 3/2020 | Vargeese et al. |
| 2020/0172903 A1 | 6/2020 | Nakamori et al. |
| 2020/0199589 A1 | 6/2020 | Kordasiewicz |
| 2020/0362347 A1 | 11/2020 | Olson et al. |
| 2020/0392494 A1 | 12/2020 | Kordasiewicz et al. |

FOREIGN PATENT DOCUMENTS

| | | |
|---|---|---|
| EP | 1135113 A1 | 9/2001 |
| EP | 1152009 A1 | 11/2001 |
| EP | 1238069 A2 | 9/2002 |
| EP | 1468694 A1 | 10/2004 |
| EP | 1481680 A1 | 12/2004 |
| EP | 1481685 A1 | 12/2004 |
| EP | 1635859 A2 | 3/2006 |
| EP | 1641468 A2 | 4/2006 |
| EP | 1716235 A2 | 11/2006 |
| EP | 1940419 A2 | 7/2008 |

(56) References Cited

FOREIGN PATENT DOCUMENTS

| | | |
|---|---|---|
| EP | 1135113 B1 | 10/2008 |
| EP | 1635859 B1 | 4/2010 |
| EP | 2322178 A2 | 5/2011 |
| EP | 1641468 B1 | 11/2011 |
| EP | 1716235 B1 | 6/2012 |
| EP | 2761002 A1 | 8/2014 |
| EP | 1670896 B1 | 1/2015 |
| EP | 2906255 A2 | 8/2015 |
| EP | 3041938 A1 | 7/2016 |
| EP | 3055414 A2 | 8/2016 |
| EP | 3076994 A2 | 10/2016 |
| EP | 3283080 A2 | 2/2018 |
| EP | 3325017 A1 | 5/2018 |
| EP | 2640853 B1 | 12/2018 |
| EP | 3415524 A1 | 12/2018 |
| EP | 3452596 A1 | 3/2019 |
| EP | 3519572 A1 | 5/2019 |
| EP | 3521451 A1 | 8/2019 |
| EP | 3283080 B1 | 3/2020 |
| EP | 2971010 B1 | 6/2020 |
| JP | 6126009 B2 | 5/2017 |
| WO | WO 1992/02258 A1 | 2/1992 |
| WO | WO 1993/007883 A1 | 4/1993 |
| WO | WO 1993/010820 A1 | 6/1993 |
| WO | WO 1994/013303 A1 | 6/1994 |
| WO | WO 1997/033550 A2 | 9/1997 |
| WO | WO 1998/039352 A1 | 9/1998 |
| WO | WO 1999/014226 A2 | 3/1999 |
| WO | WO 1999/060855 A1 | 12/1999 |
| WO | WO 1999/061066 A2 | 12/1999 |
| WO | WO 2000/002919 A1 | 1/2000 |
| WO | WO 2000/025798 A1 | 5/2000 |
| WO | WO 2000/037483 A1 | 6/2000 |
| WO | WO 2000/047599 A1 | 8/2000 |
| WO | WO 2000/066604 A2 | 11/2000 |
| WO | WO 2000/066725 A1 | 11/2000 |
| WO | WO 2001/005963 A2 | 1/2001 |
| WO | WO 2001/023613 A1 | 4/2001 |
| WO | WO 2001/057277 A2 | 8/2001 |
| WO | WO 2001/077384 A2 | 10/2001 |
| WO | WO 2001/086003 A2 | 11/2001 |
| WO | WO 2002/013799 A2 | 2/2002 |
| WO | WO 2002/032286 A2 | 4/2002 |
| WO | WO 2002/033112 A2 | 4/2002 |
| WO | WO 2002/033113 A2 | 4/2002 |
| WO | WO 2002/033114 A2 | 4/2002 |
| WO | WO 2003/004602 A2 | 1/2003 |
| WO | WO 2003/055507 A1 | 7/2003 |
| WO | WO 2004/046160 A2 | 6/2004 |
| WO | WO 2004/093783 A2 | 11/2004 |
| WO | WO 2004/093790 A2 | 11/2004 |
| WO | WO 2004/105773 A2 | 12/2004 |
| WO | WO 2004/105785 A2 | 12/2004 |
| WO | WO 2004/106356 A1 | 12/2004 |
| WO | WO 2005/004794 A2 | 1/2005 |
| WO | WO 2005/021570 A1 | 3/2005 |
| WO | WO 2005/074981 A2 | 8/2005 |
| WO | WO 2005/097817 A2 | 10/2005 |
| WO | WO 2006/034348 A2 | 3/2006 |
| WO | WO 2006/039253 | 4/2006 |
| WO | WO 2006/093034 A1 | 9/2006 |
| WO | WO 2006/099495 A2 | 9/2006 |
| WO | WO 2007/030580 A2 | 3/2007 |
| WO | WO 2007/030581 A2 | 3/2007 |
| WO | WO-2007031081 A2 | 3/2007 |
| WO | WO-2007031091 A2 | 3/2007 |
| WO | WO 2007/089584 A2 | 8/2007 |
| WO | WO 2007/089611 A2 | 8/2007 |
| WO | WO-2007090071 A2 | 8/2007 |
| WO | WO 2007/135426 A2 | 11/2007 |
| WO | WO-2007134181 A2 | 11/2007 |
| WO | WO 2007/146511 A2 | 12/2007 |
| WO | WO 2008/101157 A1 | 8/2008 |
| WO | WO 2008/113832 A2 | 9/2008 |
| WO | WO-2008150729 A2 | 12/2008 |
| WO | WO-2008154401 A2 | 12/2008 |
| WO | WO-2009006478 A2 | 1/2009 |
| WO | WO 2009/023855 | 2/2009 |
| WO | WO-2009043354 A2 | 4/2009 |
| WO | WO-2009067647 A1 | 5/2009 |
| WO | WO 2009/079399 A2 | 6/2009 |
| WO | WO-2010036698 A1 | 4/2010 |
| WO | WO-2010077578 A1 | 7/2010 |
| WO | WO-2011017521 A2 | 2/2011 |
| WO | WO-2011156202 A1 | 12/2011 |
| WO | WO 2012/027558 | 3/2012 |
| WO | WO-2012068405 A2 | 5/2012 |
| WO | WO-2013033230 A1 | 3/2013 |
| WO | WO-2013036868 A1 | 3/2013 |
| WO | WO 2013/045652 A1 | 4/2013 |
| WO | WO-2013154798 A1 | 10/2013 |
| WO | WO 2014/056298 A1 | 4/2014 |
| WO | WO 2014/059341 A2 | 4/2014 |
| WO | WO-2014076196 A1 | 5/2014 |
| WO | WO 2014/110291 A1 | 7/2014 |
| WO | WO-2014179620 A1 | 11/2014 |
| WO | WO-2014207232 A1 | 12/2014 |
| WO | WO 2015/034925 A1 | 3/2015 |
| WO | WO 2015/054676 A2 | 4/2015 |
| WO | WO 2015/085318 A2 | 6/2015 |
| WO | WO 2016/040748 A1 | 3/2016 |
| WO | WO-2016079181 A1 | 5/2016 |
| WO | WO-2016/164977 A1 | 10/2016 |
| WO | WO 2016/168592 A2 | 10/2016 |
| WO | WO 2017/015555 A1 | 1/2017 |
| WO | WO 2017/053995 A1 | 3/2017 |
| WO | WO 2017/053999 A1 | 3/2017 |
| WO | WO 2017/192664 A1 | 11/2017 |
| WO | WO-2018/064593 A1 | 4/2018 |
| WO | WO 2019/009298 A1 | 1/2019 |
| WO | WO 2019/009299 A1 | 1/2019 |
| WO | WO 2019/138057 A1 | 7/2019 |
| WO | WO 2019/140231 A1 | 7/2019 |
| WO | WO 2019/140236 A1 | 7/2019 |
| WO | WO 2019/164562 A2 | 8/2019 |
| WO | WO 2019/195519 A1 | 10/2019 |
| WO | WO 2019/217708 A1 | 11/2019 |
| WO | WO 2019/241648 A1 | 12/2019 |
| WO | WO 2020/006267 A1 | 1/2020 |
| WO | WO 2020/023737 A1 | 1/2020 |
| WO | WO 2020/055917 A1 | 3/2020 |
| WO | WO 2020/061497 A1 | 3/2020 |
| WO | WO 2020/106996 A1 | 5/2020 |
| WO | WO 2020/132558 A1 | 6/2020 |
| WO | WO 2020/160163 A1 | 8/2020 |

OTHER PUBLICATIONS

Altmann, K.H. et al., "Second generation of antisense oligonucleotides: from nuclease resistance to biological efficacy in animals," *Chimia*, 50(4): 168-176, New Swiss Chemical Society, Switzerland (1996).

Altmann, K.H. et al., "Second-generation antisense oligonucleotides: structure—activity relationships and the design of improved signal-transduction inhibitors," *Biochem Soc Trans.*, 24(3): 630-637, Portland Press, United Kingdom (1996).

Altmann, K.H. et al., "Second Generation Antisense Oligonucleotides—Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides," *Nucleosides and Nucleotides*, 16: 917-926, Informa UK Limited, England (1997).

Baker, B.F. et al., "2'-O-(2-Methoxy)ethyl-modified Anti-intercellular Adhesion Molecule 1 (ICAM-1) Oligonucleotides Selectively Increase the ICAM-1mRNA Level and Inhibit Formation of the ICAM-1 Translation Initiation Complex in Human Umbilical Vein Endothelial Cells," *J Biol Chem.*, 272(18): 11994-12000, The American Society of Biochemistry and Molecular Biology, Inc., United States (1997).

Bergstrom, D.E., "Unnatural Nucleosides With Unusual Base Pairing Properties," Current Protocols in Nucleic Acid Chemistry 37(1):1. 4.1-1.4.32, Wiley, United States (2009).

(56) References Cited

OTHER PUBLICATIONS

Bodles, A.M., et al., "Inhibition of fibril formation and toxicity of a fragment of α-synuclein by an N-methylated peptide analogue," *Neuroscience Letters*, 359 (1-2): 89-93, Elsevier, Netherlands (2004).

Braasch, D.A. and Corey, D.R., "Locked nucleic acid (LNA): fine-tuning the recognition of DNA and RNA," *Chem. Biol.*, 8(1): 1-7, Elsevier, Netherlands (2001).

Braga, C.A., et al., "The Anti-Parkinsonian Drug Selegiline Delays the Nucleation Phase of α-Synuclein Aggregation Leading to the Formation of Nontoxic Species," *Journal of Molecular Biology*, 405(1): 254-273, Elsevier, Netherlands (2011).

Burre, J. et al., "α-Synuclein promotes SNARE-complex assembly in vivo and in vitro," *Science*, 329(5999): 1663-1667, America Association for the Advancement of Science, United States (2010).

Cabin, D.E. et al., "Synaptic vesicle depletion correlates with attenuated synaptic responses to prolonged repetitive stimulation in mice lacking α-synuclein," *J Neurosci.*, 22(20): 8797-8807, Society for Neuroscience, United States (2002).

Chan, J.H.P. et al., "Antisense oligonucleotides: from design to therapeutic application," *Clinical and Experimental Pharmacology and Physiology*, 33(5-6): 533-540, Blackwell Publishing Asia Pty Ltd., Australia (2006).

Chiasson, B.J. et al., "The application of antisense oligonucleotide technology to the brain: some pitfalls," *Cell Mol Neurobiol.*, 14: 507-521, Springer Nature, United Kingdom (1994).

Chun, S., et al., "Effect of infusion of vasoactive intestinal peptide (VIP)-antisense oligodeoxynucleotide into the third cerebral ventricle above the hypothalamic suprachiasmatic nucleus on the hyperglycemia caused by intracranial injection of 2-deoxy-D-glucose in rats," *Neuroscience Letters*, 257:135-138, Elsevier, Netherlands (1998).

Clayton, D.F. and George, J.M., "Synucleins in synaptic plasticity and neurodegenerative disorders," *J. Neurosci.*, 58: 120-129, John Wiley & Sons, Inc., United States (1999).

Cole, T., et al., "Alpha-synuclein antisense oligonucleotides as a disease-modifying therapy for Parkinson's disease," *bioRxiv* 830554, doi: https://doi.org/10.1101/830554, pp. 1-42, Supplementary Materials, Cold Spring Harbor Laboratory, United States (Nov. 4, 2019).

Conway, K.A. et al., "Kinetic stabilization of the α-synuclein protofibril by a dopamine-α-synuclein adduct," *Science*, 294(5545): 1346-1349, American Association for the Advancement of Science, United States (2001).

Dass, C.R., "Vehicles for Oligonucleotide Delivery to Tumours," *The Journal of Pharmacy and Pharmacology* 54(1):3-27, Wiley, England (2002).

Database Geneseq [Online]., "Human SCNA mRNA targeted modified antisense oligonucleotide, SEQ ID 11," XP002789807. retrieved from EBI accession No. GSN:AZW44940, Database accession No. AZW44940 sequence, Jul. 5, 2012.

Database Geneseq [Online]., "Human SCNA mRNA targeted modified antisense oligonucleotide, SEQ ID 86," XP002789806. retrieved from EBI accession No. GSN:AZW45015, Database Accession No. AZW45015 sequence, Jul. 5, 2012.

Davidson, W.S. et al., "Stabilization of α-synuclein secondary structure upon binding to synthetic membranes," *J Biol Chem.*, 273: 9443-9449, The American Society for Biochemistry and Molecular Biology, Inc., United States (1998).

Deleavey, G.R. and Damha, M.J., "Designing Chemically Modified Oligonucleotides for Targeted Gene Silencing," Chemistry & Biology 19(8):937-954, Elsevier, United States (2012).

Dravid, S.M and Murray, T.F., "Spontaneous Synchronized Calcium Oscillations in Neocortical Neurons in the Presence of Physiological [Mg(2+)]: Involvement of Ampa/kainate and Metabotropic Glutamate Receptors," Brain Research 1006(1):8-17, Elsevier/North-Holland Biomedical Press, Netherlands (2004).

Dyllick-Brenzinger, M., et al., "Reciprocal Effects of α-Synuclein Overexpression and Proteasome Inhibition in Neuronal Cells and Tissue," *Neurotoxicity Research*, 17: 215-227, Springer Nature Switzerland AG, Switzerland (2010).

El-Agnaf, O.M.A. et al., "A strategy for designing inhibitors of α synuclein aggregation and toxicity as a novel treatment for Parkinson's disease and related disorders," *The FASEB Journal*, 18(11): 1315-1317, John Wiley & Sons, Inc., United States (2004).

Elayadi, A.N. and Corey, D.R., "Application of PNA and LNA oligomers to chemotherapy," *Current Opinion in Investigational Drugs*, 2(4): 558-561, PharmaPress Ltd, London (2001).

Fairman, M., et al., "Physiologically Based Pharmacokinetic (PBPK) Modeling of RNAi Therapeutics: Opportunities and Challenges," *Biochemical Pharmacology*, https://doi.org/10.1016/j.bcp.2021.114468, pp. 1-39, Elsevier, Inc., Netherlands (Feb. 10, 2021).

Freier, S.M. and Altmann, K.H., "The Ups and Downs of Nucleic Acid Duplex Stability: Structure-stability Studies on Chemically-modified DNA: RNA Duplexes," Nucleic Acids Research 25(22):4429-4443, Oxford University Press, England (1997).

Frieden, M. et al., "Expanding the design horizon of antisense oligonucleotides with alpha-I-LNA," *Nucleic Acids Research*, 31(21): 6365-6372, Oxford University Press, England (2003).

Galvin J. E., et al., "Synucleinopathies: Clinical and Pathological Implications," Archives of Neurology, 58(2):186-190, American Medical Assn., Chicago. (2001).

Gautschi, O., et al., "Activity of a Novel bcl-2/bcl-xL-Bispecific Antisense Oligonucleotide Against Tumors of Diverse Histologic Origins," *J Natl Cancer Inst.*, 93(6): 463-471, Oxford University Press, England (2001).

GenBank Accession No. BC013293.2, "*Homa sapiens* synuclein, alpha (non A4 component o amyloied precursor), mRNA (cDNA clone MGC:3484 IMAGE:3604532), complete cds," available at (https://www.ncbi.nlm.nih.gov/nuccore/BC013293.2).

GenBank Accession No. BG701026.1, "602682033F1 NIH_MGC_95 *Homo sapiens* cDNA clone IMAGE:4814505 5',mRNA dequence," available at (https://www.ncbi.nlm.nih.gov/nuccore/BG701026).

GenBank Accession No. BM069769.1, "ie89b06.y1 Melton Normalized Human Islet 4 N4-HIS 1 *Homo sapiens* cDNA clone IMAGE:5673946 5' similar to SW:SYUA_HUMAN P37840 Alpha-Synuclein, mRNA sequence," available at (https://www.ncbi.nlm.nih.gov/nuccore/BM069769).

GenBank Accession No. L36674.1, "Human (clone 2-5) synuclein (NACP) mRNA, complete cds," available at (https://www.ncbi.nlm.nih.gov/nuccore/L36674).

Gerard, M., et al., "Inhibition of FK506 Binding Proteins Reduces α-Synuclein Aggregation and Parkinson's Disease-Like Pathology," *The Journal of Neuroscience*, 30(7): 2454-2463, The Society for Neurosciences, United States (2010).

Glaser, C.B., et al., "Methionine oxidation, α-synuclein and Parkinson's disease," *Biochimica et Biophysica Acta*, 1703(2): 157-169, Elsevier, Netherlands (2005).

Goodchild, J., (ed), Methods in Molecular Biology, Therapeutic Oligonucleotides, Methods and Protocols, vol. 764, pp. 1-340, Humana Press, United States (2011).

Grunweller A., et al., "Locked Nucleic Acid Oligonucleotides: The Next Generation of Antisense Agents?," Bio Drugs, 21(4):235-243, Springer International, Adis. (2007).

Henry, S. et al., "Chemically modified oligonucleotides exhibit decreased immune stimulation in mice," *The Journal of Pharmacology and Experimental Therapeutics*, 292(2): 468-479, The American Society for Pharmacology and Experimental Therapeutics, United States (2000).

Herrera, F.E., et al., "Inhibition of α-Synuclein Fibrillization by Dopamine Is Mediated by Interactions with Five C-Terminal Residues and with E83 in the NAC Region," *PLoS One*, 3(10): e3394, (2008).

Hillmer, A.S., et al., "Converse modulation of toxic α-synuclein oligomers in living cells by N'-benzylidene-benzohydrazide derivates and ferric iron," *Biochem Biophys Res Commun.*, 391(1): 461-466, Elsevier, Netherlands (2010).

Hirao, I., et al., "Natural Versus Artificial Creation of Base Pairs in DNA: Origin of Nucleobases From the Perspectives of Unnatural Base Pair Studies," Accounts of Chemical Research 45(12):2055-2065, American Chemical Society, United States (2012).

Hughes, E., et al., "Inhibition of Toxicity in the β-Amyloid Peptide Fragment β-(25-35) Using N-Methylated Derivatives: A General Strategy To Prevent Amyloid Formation," *J. Biol. Chem.*,

(56) References Cited

OTHER PUBLICATIONS

275(33):25109-25112, The American Society for Biochemistry and Molecular Biology, Inc., United States (2000).
International Search Report and Written Opinion for International Application No. PCT/US2019/013255, European Patent Office, Netherlands, dated Apr. 8, 2019.
International Search Report and Written Opinion for International Application No. PCT/US2019/013249, dated Apr. 2, 2019, 13 pages.
Ishido, M., "Melatonin inhibits maneb-induced aggregation of α-synuclein in rat pheochromocytoma cells," *Journal of Pineal Research*, 42(2): 125-130, Wiley-Blackwell, United States (2007).
Iwai, A. et al., "The precursor protein of non-Aβ component of Alzheimer's disease amyloid is a presynaptic protein of the central nervous system," *Neuron*, 14: 467-475, Cell Press, United States (1995).
Jafar-Nejad, P., et al., "The atlas of RNase H antisense oligonucleotide distribution and activity in the CNS of rodents and non-human primates following central administration," *Nucleic Acids Research*, 49(2):657-673, Oxford University Press, England (Dec. 24, 2020).
Jiang, M., et al., "Baicalein reduces E46K α synuclein aggregation in vitro and protects cells against E46K α synuclein toxicity in cell models of familiar Parkinsonism," *Journal of Neurochemistry*, 114(2): 419-429, International Society for Neurochemistry, Switzerland (2010).
Kalivendi, S., et al., "α-Synuclein Up-regulation and Aggregation during MPP$^+$-induced Apoptosis in Neuroblastoma Cells: Intermediacy of Transferrin Receptor Iron and Hydrogen Peroxide," *The Journal of Biological Chemistry*, 279(15):15240-15247, The American Society for Biochemistry and Molecular Biology, Inc., United State (2004).
Karimy, JK, et al., "Inflammation-dependent cerebrospinal fluid hypersecretion by the choroid plexus epithelium in posthemorrhagic hydrocephalus," *Nature Medicine*, 23:997-1003, Supplemental Information, Springer Nature Limited, Germany (2017).
Koshkin, A.A., et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," *Tetrahedron*, 54(14): 3607-3630, Elsevier, Netherlands (1998).
Kramer, M.L. and Schulz-Schaeffer, W.J., "Presynaptic α-synuclein aggregates, not Lewy bodies, cause neurodegeneration in dementia with Lewy bodies," *J. Neurosci.*, 27: 1405-1410, Society for Neuroscience, United States (2007).
Kumar, R. et al., "The first analogues of LNA (Locked Nucleic Acids)" phosphorothioate-LNA and 2'-thio-LNA,*Bioorg Med Chem Lett.*, 8: 2219-2222, Elsevier, Netherlands (1998).
Kuo Y. M., et al., "Extensive Enteric Nervous System Abnormalities in Mice Transgenic for Artificial Chromosomes Containing Parkinson Disease-Associated Alpha-Synuclein Gene Mutations Precede Central Nervous System Changes," Human Molecular Genetics, 19(9):1633-1650, Oxford University Press, Oxford. (2010).
Lamberto, G.R., et al., "Structural and mechanistic basis behind the inhibitory interaction of PcTS on α-synuclein amyloid fibril formation," *Proc Natl Acad Sci USA*, 106(50): 21057-21062 (2009).
Ledochowitsch, P., et al., "Fabrication and testing of a large area, high density, parylene MEMS μECoG array," 2011 IEEE 24th International Conference on Micro Electro Mechanical Systems, Cancun, Mexico Jan. 23-27, 2011, pp. 1031-1034 (2011).
Lee, H.J. at al., "Membrane-bound α-synuclein has a high aggregation propensity and the ability to seed the aggregation of the cytosolic form," *J. Biol. Chem.*, 277(1): 671-678, Elsevier, Netherlands (2002).
Lendel, C., et al., "On the Mechanism of Nonspecific Inhibitors of Protein Aggregation: Dissecting the Interactions of α-Synuclein with Congo Red and Lacmoid," *Biochemistry*, 48(35): 8322-8334, Supplemental Information, American Chemical Society, United States (2009).
Leumann, C.J., "DNA analogues: from supramolecular principles to biological properties," *Bioorganic & Medicinal Chemistry*, 10:841-854, Elsevier Science Ltd., Netherlands (2002).
Li, J., et al., "Rifampicin Inhibits α-Synuclein Fibrillation and Disaggregates Fibrils," *Chem Biol.*, 11(11): 1513-1521, Elsevier Science Ltd., Netherlands (2004).
Liu, S., et al., "α-Synuclein produces a long-lasting increase in neurotransmitter release," *The EMBO Journal*, 23(2): 4506-4516, European Molecular Biology Organization, Germany (2004).
Lotharius, J. and Brundin, P., "Pathogenesis of parkinson's disease: dopamine, vesicles and α-synuclein," *Nature Reviews Neuroscience*, 3:932-942, Springer Nature Limited, Germany (2002).
Lu, Z.J., and D.H. Mathews, "Fundamental differences in the equilibrium considerations for siRNA and antisense oligodeoxynucleotide design," *Nucleic Acids Research*, 36(11): 3738-3745, Oxford University Press, England (2008).
Lucking, C.B. and Brice, A., "Alpha-synuclein and Parkinson's disease," *Cell. Mol. Life Sci. CMLS*, 57:1894-1908 (2000).
Maguire-Zeiss, K.A., "α-Synuclein: A therapeutic target for Parkinson's disease," *Pharmacol Res.*, 58: 271-280, Elsevier, Netherlands (2008).
Maher, L.J. and B.J. Dolnick, "Comparative hybrid arrest by tandem antisense oligodeoxyribonucleotides or oligodeoxyribonucleoside methylpbosphonates in a cell-free system," *Nucleic Acids Research*, 16(8): 3341-3358, IRL Press Limited, Oxford, England (1988).
Manoharan M., "Oligonucleotide Conjugates as Potential Antisense Drugs with Improved Uptake, Biodistribution, Targeted Delivery, and Mechanism of Action," Antisense and Nucleic Acid Drug Development, 12(2):103-128, Mary Ann Liebert, Inc., New York. (2002).
Marques O., et al., "Alpha-Synuclein: From Secretion to Dysfunction and Death," Cell Death & Disease, 3(7):e350, Nature Pub. Group, London. (2012).
Martin, P., Ein neuerZugang zu 2' O Alkylribonucleosiden und Eigenschaften deren Oligonucleotide,: *Helv Chim Acta*, 78: 486-504, John Wiley & Sons, Switzerland (1995) (English Language Abstract).
Martinez, Z., et al., "GM1 Specifically Interacts with α-Synuclein and Inhibits Fibrillation," *Biochemistry*, 46(7): 1868-1877, American Chemical Society, United States (2007).
McCormack, A., et al., "α-Synuclein Suppression by Targeted Small Interfering RNA in the Primate Substantia Nigra," *PLoS ONE*, 5(8): e12122, pp. 1-8, Public Library of Sciene, United States (2010).
Meng, X., et al., "Molecular Mechanisms Underlying the Flavonoid-Induced Inhibition of α-Synuclein Fibrillation," *Biochemistry*, 48(43): 8206-8224, American Chemical Society, United States (2009).
Mitsuoka Y., et al., "A Bridged Nucleic Acid, 2',4'-BNA COC: Synthesis of Fully Modified Oligonucleotides Bearing Thymine, 5-Methylcytosine, Adenine and Guanine 2',4'-BNA COC Monomers and RNA-Selective Nucleic-Acid Recognition," Nucleic Acids Research, 37(4):1225-1238, Oxford University Press, Oxford. (2009).
Monti, B., et al., "Alpha-synuclein protects cerebellar granule neurons against 6-hydroxydopamine-induced death," *Journal of Neurochemistry*, 103(2): 518-530, International Society for Neurochemistry, Switzerland (2007).
Monti, B., et al., "Valproic Acid is Neuroprotective in the Rotenone Rat Model of Parkinson's Disease: Involvement of α-Synuclein," *Neurotoxicity Research*, 17: 130-141, Springer, Germany (2010).
Morita K., et al., "2'-O,4'-C-Ethylene-Bridged Nucleic Acids (ENA): Highly Nuclease-Resistant and Thermodynamically Stable Oligonucleotides for Antisense Drug," Bioorganic and Medicinal Chemistry Letters, 12(1):73-76, Elsevier Science Ltd, Oxford. (2002).
Murphy, D.D., et al., "Synucleins are Developmentally Expressed, and α-Synuclein Regulates the Size of the Presynaptic Vesicular Pool in Primary Hippocampal Neurons," *Journal of Neuroscience*, 20(9):3214-3220, Society for Neuroscience, United States (2000).
NCBI Accession No. NC_000004.12, "*Homo sapiens* chromosome 4, GRCh38.p13 Primary Assembly," available at (https://www.ncbi.nlm.nih.gov/nuccore/NC_000004.12/).
NCBI, "*Homo sapiens* Synuclein Alpha (Snca), RefSeqGene on Chromosome 4," Accession No. NG_011851.1, accessed at https://www.ncbi.nlm.nih.gov/nuccore/NG_011851.1.

(56) References Cited

OTHER PUBLICATIONS

NCBI Accession No. NM_000345.3, "NM_000345.3(SNCA):c. *2501C>A and Parkinson Disease, Dominant," available at (https://www.ncbi.nlm.nih.gov/clinvar/21945055/).

NCBI Accession No. NM_007308.1, "*Homo sapiens* synuclein, alpha (non A4 component of amyloid precursor) (SNCA), transcript variant NACP112, mRNA," available at (https://www.ncbi.nlm.nih.gov/nuccore/NM_007308.1).

NCBI Accession No. NM_001042451.1, "Mus musculus synuclein, alpha (Snca), transcript variant 1, mRNA," available at (https://www.ncbi.nlm.nih.gov/nuccore/NM_001042451.1).

NCBI Accession No. NT_016354.17, "*Homo sapiens* chromosome 4 genomic contig," available at (https://www.ncbi.nlm.nih.gov/nuccore/NT_016354.17).

Ono, K., et al., "α-Synuclein Assembly as a Therapeutic Target of Parkinson's Disease and Related Disorders," *Curr. Pharm. Des.*, 14(30): 3247-3266 (2008).

Orum, H. and J. Wengel, "Locked nucleic acids: a promising molecular family for gene-function analysis and antisense drug development," *Current Opinion in Molecular Therapeutics*, 3(3): 239-243 (2001).

Paleologou, K.E., et al., "α-Synuclein aggregation in neurodegenerative diseases and its inhibition as a potential therapeutic strategy," *Biochem Soc Trans.*, 33(5): 1106-1110, Biochemical Society, London (2005).

Pasti, L., et al., "Cytosolic Calcium Oscillations in Astrocytes May Regulate Exocytotic Release of Glutamate," The Journal of Neuroscience 21(2):477-484, Society for Neuroscience, United States (Jan. 2001).

Putcha, P., et al., "Brain-Permeable Small-Molecule Inhibitors of Hsp90 Prevent α-Synuclein Oligomer Formation and Rescue α-Synuclein-Induced Toxicity," *J Pharmacol Exp Ther*, 332(3): 849-857, The American Society for Pharmacology and Experimental Therapeutics, United States (2010).

Qin, Z., et al., "Effect of 4-Hydroxy-2-nonenal Modification on α-Synuclein Aggregation," *J Biol Chem.*, 282: 5862-5870, The American Society for Biochemistry and Molecular Biology, Inc., United States (2007).

Rayburn, E.R. and Zhang, R., "Antisense, RNAi, and gene silencing strategies for therapy: Mission possible or impossible?," *Drug Discovery Today*, 13(11-12):513-521, Elsevier, Netherlands (2008).

Recchia A., et al., "Alpha-Synuclein and Parkinson's Disease," FASEB J, 18(6):617-626, Hoboken, NJ. (2004).

Rekas, A., et al., "PAMAM Dendrimers as Potential Agents against Fibrillation of α-Synuclein, a Parkinson's Disease-Related Protein," *Macromolecular Bioscience*, 9(3): 230-238, WILEY-VCH Verlag GmbH & Co. KGaA, Weinheim (2009).

Rockenstein, E. et al., "Differential neuropathological alterations in transgenic mice expressing α-synuclein from the platelet-derived growth factor and Thy-1 promoters," *J Neurosci Res.*, 68: 568-578, Wiley-Liss, Inc., United States (2002).

Rose, C.R. and Konnerth, A., "Exciting Glial Oscillations," Nature Neuroscience 4(8):773-774, Nature Publishing Group, United States (2001).

Sarkar, S., et al., "Trehalose, a Novel mTOR-independent Autophagy Enhancer, Accelerates the Clearance of Mutant Huntingtin and α-Synuclein," *J Biol Chem.*, 282: 5641-5652, The American Society for Biochemistry and Molecular Biology, Inc., United States (2007).

Segers-Nolten, I.M.J., "Tissue transglutaminase modulates α synuclein oligomerization," *Protein Science*, 17(8): 1395-1402, Cold Spring Harbor Laboratory Press, United States (2008).

Seth, P.P., et al., "Synthesis and Biophysical Evaluation of 2',4'-constrained 2'O-methyoxyethyl and 2',4'-constrained 2'O-ethyl Nucleic Acid Analogues," Journal of Organic Chemistry 75(5):1569-1581, American Chemical Society, United States (Mar. 2010).

Schulze-Schaeffer, W.J., "The synaptic pathology of α-synuclein aggregation in dementia with Lewy bodies, Parkinson's disease and Parkinson's disease dementia," *Acta Neuropathol.*, 120: 131-143, Springer, Germany (2010).

Singh, S.K. et al., "LNA (locked nucleic acids): synthesis and high-affinity nucleic acid recognition," *Chem Commun.*, 4: 455-456, Elsevier B.V., Netherlands (1998).

Singh, S.K. et al., "Synthesis of 2'-Amino-LNA: A Novel Conformationally Restricted High-Affinity Oligonucleotide Analogue with a Handle," *J Org Chem.*, 63(26): 10035-10039, American Chemical Society, United States (1998).

Smith, L., et al., "Rational selection of antisense oligonucleotide sequences," *European Journal of Pharmaceutical Sciences*, 11:191-198, Elsevier Sciences B.V., Netherlands (2000).

Snyder, H., et al., "β-Synuclein Reduces Proteasomal Inhibition by α-Synuclein but Not γ-Synuclein," *Journal of Biological Chemistry*, 280(9): 7562-7569, Elsevier, Netherlands (2005).

Sohail, M. and Southern, E.M., "Selecting optimal antisense reagents," *Advanced Drug Delivery Reviews*, 44:23-34, Elsevier, Netherlands (2000).

Souza, J.M. et al., "Chaperone-like activity of synucleins," *FEBS Lett.*, 474: 116-119, Elsevier, Netherlands (2000).

Srivastava, P., et al., "Five- and Six-Membered Conformationally Locked 2',4'-Carbocyclic ribo-Thymidines: Synthesis, Structure, and Biochemical Studies," *J Am Chem Soc.*, 129 (26): 8362-8379, American Chemical Society, United States (2007).

Stowe, R.P., et al., "Detection and Quantification of Epstein-Barr Virus EBER1 in EBV-infected Cells by Fluorescent in situ Hybridization and Flow Cytometry," Journal of Virological Methods 75(1):83-91, Elsevier/North-Holland Biomedical Press, Netherlands (1998).

Touboul, M., et al., "Early Detection of Chemoresistance in Vivo through the use of a Radiolabeled Antisense Oligonucleotide," Anticancer Research 22(6A):3349-3356, International Institute of Anticancer Research, Greece (2002).

Uehara T., et al., "Anti Sense Oligonucleotides Containing Amido-Bridged Nucleic Acid Reduce SNCA Expression and Improve Motor Function in Parkinson's Disease Animal Models," A Journal of Neurological Sciences, vol. 381:1044-1045, Science Direct. (2017).

Uehara, T., "Amido-bridged nucleic acid (AmNA)-modified antisense oligonucleotides targeting α-synuclein as a novel therapy for Parkinson's disease," *Scientific Reports*, 9:7567, Springer Nature Limited, Germany (May 21, 2019).

Uhlmann, E., "Recent Advances in the Medicinal Chemistry of Antisense Oligonucleotides," Current Opinion in Drug Discovery and Development 3(2):203-213, Thomson Reuters Scientific Ltd., England (2000).

UniProtKB Primary Accession No. P37840; Secondary Accession Nos. A8K2A4, Q6IAU6, Q13701, Q4JHI3, Q6IAU6 available at (https://www.uniprot.org/uniprot/P37840).

Uversky, V.N., "Neuropathology, biochemistry, and biophysics of α synuclein aggregation," *J. Neurochem.*, 103:17-37, International Society for Neurochemistry, Switzerland (2007).

Valera E., et al., "Therapeutic Approaches in Parkinson's Disease and Related Disorders," Journal of Neurochemistry, 139 Suppl 1(Suppl 1):346-352, Wiley on behalf of the International Society for Neurochemistry, Oxford. (2016).

Verjat et al., "Detection of 8-oxoG DNA glycosylase activity and OGG1 transcripts in the rat CNS," *Mutat. Res.*, 640: 127-38, Elsevier, Netherlands (2000).

Vickers, T.A. et al., "Effects of RNA secondary structure on cellular antisense activity," *Nucleic Acids Research*, 28(6): 1340-1347, Oxford University Press, England (2000).

Vickers, T.A. et al., "Efficient reduction of target RNAs by small interfering RNA and RNase H-dependent antisense agents—A comparative analysis," *The Journal of Biological Chemistry*, 278(9): 7108-7118, The American Society for Biochemistry and Molecular Biology, Inc., United States (2003).

Wahlestedt, C. et al., "Potent and nontoxic antisense oligonucleotides containing locked nucleic acids," *Proc Natl Acad Sci USA*, 97(10): 5633-5638 (2000).

Wan W. B., et al., "The Medicinal Chemistry of Therapeutic Oligonucleotides," Journal of Medicinal Chemistry, 59(21):9645-9667, American Chemical Society, Washington. (2016).

Woolf, T.M., et al., "Specificity of antisense oligonucleotides in vivo," *Proc Natl Acad Sci USA*, 89(16): 7305-7309 (1992).

(56) References Cited

OTHER PUBLICATIONS

Xu, J., "Rifampicin protects PC12 cells against MPP+-induced apoptosis and inhibits the expression of an α-Synuclein multimer," *Brain Research*, 1139: 220-225, Elsevier, Netherlands (2007).
Yoshida, M., "Multiple system atrophy: a-synuclein and neuronal degeneration," *Neuropathology*, 27: 484-493, Japanese Society of Neuropathology, Tokyo (2007).
Zhou, C., et al., "A human single-chain Fv intrabody blocks aberrant cellular effects of overexpressed α-synuclein," *Molecular Therapy*, 10(6): 1023-1031, The American Society of Gene Therapy, United States (2004).
Zhou, C. et al., "Fine Tuning of Electrostatics around the Internucleotidic Phosphate through Incorporation of Modified 2',4'-Carbocyclic-LNAs and -ENAs Leads to Significant Modulation of Antisense Properties," *J Org Chem*, 74(1): 118-134, Supplemental Information, American Chemical Society, United States (2009).
Zhou, W., et al., "At Low Concentrations, 3,4-Dihydroxyphenylacetic Acid (DOPAC) Binds Non-Covalently to α-Synuclein and Prevents Its Fibrillation," *Journal of Molecular Biology*, 388(3): 597-610, Elsevier, Netherlands (2009).
Zhu, M. and A.L. Fink, "Lipid Binding Inhibits α-Synuclein Fibril Formation," *J Biol Chem.*, 278: 16873-16877, The American Society for Biochemistry and Molecular Biology, Inc., United States (2003).
Zonta, M. and Carmignoto, G., "Calcium Oscillations Encoding Neuron-to-astrocyte Communication," Journal of Physiology 96(3-4):193-198, Editions Scientifiques Elsevier, France (2002).
Toth, Z.E., et al., "Bone Marrow-Derived Nonreactive Astrocytes in the Mouse Brain After Permanent Middle Cerebral Artery Occlusion," *Stem Cells and Development*, 20(3):539-546, Mary Ann Liebert, Inc., United States (2011).
Kole, R., et al., "RNA therapeutics: beyond RNA interference and antisense oligonucleotides," Nature Reviews, 11:125-140, Macmillan Publishers Limited, United States (2012).
Peng, B., et al., "Tissue Distribution and Physiologically Based Pharmacokinetics of Antisense Phosphorothioate Oligonucleotide ISIS 1082 in Rat," *Antisense & Nucleic Acid Drug Development*, 11:15-27, Mary Ann Liebert, Inc., United States (2001).
Beaucage, S.L. and R.P. Iyer, "Advances in the Synthesis of Oligonucleotides by the Phosphoramidite Approach," *Tetrahedron*, 48(12):2223-2311, Elsevier, Netherlands (1992).
U.S. Appl. No. 08/050,698, inventors Froehler, B., et al., filed Apr. 19, 1993 (Not Published).
U.S. Appl. No. 17/165,841, inventors Richard E. Olson, et al., filed Feb. 2, 2021 (Not Published).
Alterman, J.F., et al., "A divalent siRNA chemical scaffold for potent and sustained modulation of gene expression throughout the central nervous system," Nature Biotechnology 37:884-894, Nature Publishing Group, England (Aug. 2019).
Bennett, C.F., et al., "RNA Targeting Therapeutics: Molecular Mechanisms of Antisense Oligonucleotides as a Therapeutic Platform," Annu. Rev. Pharmacol. Toxicol 50:259-293, Annual Reviews, United States (2010).
Burel, S.A., et al., "Hepatotoxicity of high affinity gapmer antisense oligonucleotides is mediated by RNase H1 dependent promiscuous reduction of very long pre-mRNA transcripts," Nucleic Acids Research 44(5):2093-2109, Oxford University Press, England (2016).
Chan, J.HP., et al., "Antisense Oligonucleotides: From design to Therapeutic Application," Clinical and Experimental Pharmacology and Physiology 33:533-540, Blackwell Publishing Asia Pty Ltd., Australia (2006).
Crooke, S.T., et al., "Antisense technology: A review," J. Biol. Chem 296: 1-39, Elsevier, Netherlands (Feb. 2021).
Crooke, S.T., et al., "Antisense drug discovery and development technology considered in a pharmacological context," Biochemical Pharmacology 189:114196, Elsevier, Netherlands (Aug. 2020).
Crooke, S.T., et al., "Antisense technology: an overview and prospectus," Nature Rev Drug Discov. 20(6):427-453, Nature Publishing Group, England (Mar. 2021).
European Patent Register, "European Patent EP2640853 File History," retrieved from: <https://register.epo.org/application?number=EP11840796&lng=en&tab=doclist>, retrieved on Jan. 25, 2022, 3258 pages.
Jahns, H., et al., "Chirality matters: stereo-defined phosphorothioate linkages at the termini of small interfering RNAs improve pharmacology in vivo," Nucleic Acids Research: 1-20, Oxford University Press, England (Jul. 2021).
Kamola, P.J., et al., "In silico and in vitro evaluation of exonic and intronic off-target effects form a critical element of therapeutic ASO gapmer optimization," Nucleic Acids Research 43(18):8638-8650, Oxford University Press, England (2015).
Karaki, S., et al., "Antisense Oligonucleotides, A Novel Developing Targeting Therapy," Antisense Therapy:1-19, IntechOpen, France (Feb. 2019).
Khvorova, A., et al., "The chemical evolution of oligonucleotide therapies of clinical utility," Nature Biotechnology 35(3):238-248, Nature Publishing Group, England (Mar. 2017).
Lewis, J., et al., "In vivo silencing of alpha-synuclein using naked siRNA," Molecular Neurodegeneration 3(19): 1-10, BioMed Central, United Kingdom (2008).
Martinez, J., et al., "Single-Stranded Antisense siRNAs Guide Target RNA Cleavage in RNAi," Cell 110:563-574, Cell Press, United States (2002).
Possin, K.L., et al., "Visual Spatial Cognition in Neurodegenerative disease," Neurocase 16(6):466-487, Taylor & Francis Online, United States (2010).
Rudin, C.M., et al., "Delivery of a Liposomal c-raf-1 Antisense Oligonucleotide by Weekly Bolus dosing in Patients with Advanced Solid Tumors: A Phase I Study," Clinical Cancer Research 10:7244-7251, American Association for Cancer Research, United States (2004).
Scoles, D.R., et al., "Antisense oligonucleotides," Neurology: Genetics 5(2):1-8, American Academy of Neurology, United States (Apr. 2019).
Seth, P.P., et al., "Short Antisense Oligonucleotides with Novel 2'-4' Conformationaly Restricted Nucleoside Analogues Show Improved Potency without Increased Toxicity in Animals," J. Med. Chem 52:10-13, American Chemical Society, United States (2008).
Seth, P.P., et al., "Design, Synthesis and Evaluation of Constrained Methoxyethyl (cMOE) and Constrained Ethyl (cEt) Nucleoside Analogs," Nucleic Acids Symposium Series 52:553-554, Oxford University Press, England (2008).
Swayze, E.C., et al., "Antisense oligonucleotides containing locked nucleic acid improve potency but cause significant hepatotoxicity in animals," Nucleic Acid Research 35(2): 687-700, Oxford University Press, England (2007).
Yu, R.Z., et al., "Cross-Species Pharmacokinetic Comparison from Mouse to Man of a Second-Generation Antisense Oligonucleotide, ISIS 301012, Targeting Human Apolipoprotein B-100," Drug Metabolism and Disposition 35(3):460-468, American Society for Pharmacology and Experimental Therapeutics, United States (2007).
Yu, R.Z., et al., "Comparison of Pharmacokinetics and Tissue Disposition of an Antisense Phosphorothioate Oligonucleotide Targeting Human Ha-ras mRNA in Mouse and Mickey," Journal of Pharmaceutical Sciences 90(2):182-193, Wiley-Liss, United States (2001).
Office Action dated Jul. 13, 2021 in U.S. Appl. No. 17/165,841, inventor Olson; Richard E., filed Feb. 2, 2021, 7 pages.
Office Action dated Mar. 31, 2021 in U.S. Appl. No. 17/165,841, inventor Olson; Richard E.,filed Feb. 2, 2021, 9 pages.

OxyAs DNAts OxyTs DNAcs DNAcs DNAts DNAts DNAts DNAas DNAcs DNAts DNAcs OxyAs OxyMCs OxyAs OxyMC

SEQ ID NO: 4

ANTISENSE OLIGONUCLEOTIDES TARGETING ALPHA-SYNUCLEIN AND USES THEREOF

REFERENCE TO SEQUENCE LISTING SUBMITTED ELECTRONICALLY

The content of the electronically submitted sequence listing (Name: 3338_107PC01_SequenceListing_ST25.txt, Size: 10,458 bytes; and Date of Creation: Jan. 10, 2019) submitted in this application is incorporated herein by reference in its entirety.

FIELD OF THE DISCLOSURE

The present disclosure relates to an antisense oligomeric compound (ASO) that targets the junction of intron 1 and exon 2 of alpha-synuclein (SNCA) transcript in a cell, leading to reduced expression of alpha-synuclein (SNCA) protein. Reduction of SNCA protein expression can be beneficial for a range of medical disorders, such as multiple system atrophy, Parkinson's disease, Parkinson's Disease Dementia (PDD), and dementia with Lewy bodies.

BACKGROUND OF THE DISCLOSURE

Alpha-synuclein (SNCA), a member of the synuclein protein family, is a small soluble protein that is expressed primarily within the neural tissues. See Marques O et al., *Cell Death Dis.* 19: e350 (2012). It is expressed in many cell types but is predominantly localized within the presynaptic terminals of neurons. While the precise function has yet to be fully elucidated, SNCA has been suggested to play an important role in the regulation of synaptic transmission. For instance, SNCA functions as a molecular chaperone in the formation of SNARE complexes, which mediate the docking of synaptic vesicles with the presynaptic membranes of neurons. SNCA can also interact with other proteins like the microtubule-associated protein tau, which helps stabilize microtubules and regulate vesicle trafficking.

Due to SNCA's role in the regulation of synaptic transmission, alterations of SNCA expression and/or function can disrupt critical biological processes. Such disruptions have been thought to contribute to α-synucleinopathies, which are neurodegenerative diseases characterized by abnormal accumulation of SNCA protein aggregates within the brain. Accordingly, insoluble inclusions of misfolded, aggregated, and phosphorylated SNCA protein are a pathological hallmark for diseases such as Parkinson's disease (PD), Parkinson's Disease Dementia (PDD), dementia with Lewy bodies (DLB), and multiple system atrophy (MSA). See Galvin J E et al., *Archives of Neurology* 58: 186-190 (2001); and Valera E et al., *J Neurochem* 139 Suppl 1: 346-352 (October 2016).

α-Synucleinopathies, such as Parkinson's disease, are highly prevalent progressive neurodegenerative brain disorders, especially among the elderly. See Recchia A et al., *FASEB J.* 18: 617-26 (2004). It is estimated that approximately seven to ten million people worldwide are living with such disorders, with about 60,000 new cases each year in the United States alone. Medication costs for an individual person can easily exceed $2,500 a year and therapeutic surgery can cost up to $100,000 per patient. Therefore, a more robust and cost-effective treatment options are greatly needed.

BRIEF SUMMARY OF THE DISCLOSURE

The present disclosure is directed to an antisense oligonucleotide (ASO) comprising, consisting essentially of, or consisting of the contiguous nucleotide sequence of AtTcctt-tacaccACAC (SEQ ID NO: 4), wherein the upper letter is beta-D-oxy-LNA and the lower letter is DNA. In other embodiments, the ASO comprises an internucleotide linkage selected from the group consisting of a phosphodiester linkage, a phosphotriester linkage, a methylphosonate linkage, a phosphoramidate linkage, a phosphorothioate linkage, and combinations thereof. In certain embodiments, the internucleotide linkage is a phosphorothioate linkage.

In some embodiments, the ASO comprises, consists essentially of, or consists of OxyAs DNAts OxyTs DNAcs DNAcs DNAts DNAts DNAts DNAas DNAcs DNAas DNAcs DNAcs OxyAs OxyMCs OxyAs OxyMC, wherein OxyA, OxyT, and Oxy MC are adenine beta D-oxy-LNA, thymine beta D-oxy-LNA, and methyl cytosine beta D-oxy-LNA, respectively, and wherein DNAt, DNAc, and DNAa are thymine DNA, cytosine DNA, and adenine DNA, respectively. In some embodiments, the ASO of the present disclosure comprises a molecular formula of $C_{171}H_{214}N_{56}O_{90}P_{16}S_{16}$ and a structure as shown in FIG. 1B, wherein $M^+$ is a counterion. In some embodiments, the counterion is selected from the group consisting of $H^+$, $Na^+$, $NH4^+$, and any combination thereof. In certain embodiments, the counterion is $Na^+$.

The present disclosure also provides a conjugate comprising the ASO as disclosed herein, wherein the ASO is covalently attached to at least one non-nucleotide or non-polynucleotide moiety. In some embodiments, the non-nucleotide or non-polynucleotide moiety comprises a protein, a fatty acid chain, a sugar residue, a glycoprotein, a polymer, or any combinations thereof.

Also provided herein is a pharmaceutical composition comprising the ASO or the conjugate as disclosed herein and a pharmaceutically acceptable carrier. In some embodiments, the composition further comprises a therapeutic agent. In certain embodiments, the therapeutic agent is an alpha-synuclein antagonist. In some embodiments, the alpha-synuclein antagonist is an anti-alpha-synuclein antibody or fragment thereof.

The present disclosure further provides a kit comprising the ASO, the conjugate, or the composition as disclosed herein. Also disclosed is a diagnostic kit comprising the ASO, the conjugate, or the composition of the present disclosure.

The present disclosure is also directed to method of inhibiting or reducing SNCA protein expression in a cell, the method comprising administering the ASO, the conjugate, or the composition as disclosed herein to the cell expressing SNCA protein, wherein the SNCA protein expression in the cell is inhibited or reduced after the administration. In some embodiments, the ASO inhibits or reduces expression of SNCA mRNA in the cell after the administration. In certain embodiments, the expression of SNCA mRNA is reduced by at least about 20%, at least about 30%, at least about 40%, at least about 50%, at least about 60%, at least about 70%, at least about 80%, at least about 90%, or about 100% after the administration compared to a cell not exposed to the ASO. In other embodiments, the ASO reduces expression of SNCA protein in the cell after the administration by at least about 60%, at least about 70%, at least about 80%, or at least about 90% compared to a cell not exposed to the ASO. In some embodiments, the cell is a neuron.

Provided herein is a method for treating a synucleinopathy in a subject in need thereof, comprising administering an effective amount of the ASO, the conjugate, or the composition of the present disclosure. In some embodiments, the synucleinopathy is selected from the group consisting of Parkinson's disease, Parkinson's Disease Dementia (PDD), multiple system atrophy, dementia with Lewy bodies, and any combinations thereof.

Also provided herein is a use of the ASO, the conjugate, or the composition of the present disclosure for the manufacture of a medicament. The present disclosure also provides the use of the ASO, the conjugate, or the composition for the manufacture of a medicament for the treatment of a synucleinopathy in a subject in need thereof. In some embodiments, the ASO, the conjugates, or the composition of the present disclosure is for use in therapy of a synucleinopathy in a subject in need thereof. In other embodiments, the ASO, the conjugates, or the composition of the present disclosure is for use in therapy.

In some embodiments, the subject is a human. In some embodiments, the ASO, the conjugates, or the compositions is administered orally, parenterally, intrathecally, intra-cerebroventricularly, pulmonarily, topically, or intraventricularly.

BRIEF DESCRIPTION OF THE FIGURES

In FIG. 5A, the A53T-PAC mice were dosed with 3.13 μg, 12.5 μg, 25 μg, or 50 μg of ASO-005459 and their bodyweights measured at weeks 0, 1, and 2 post-treatment. In FIG. 5B, C57BL/6 mice were dosed with 100 μg of ASO-005459 and the animals' body weight was measured once a week during a course of 28 days. In both FIGS. 5A and 5B, animals receiving the vehicle control were used as controls. Data shown represents the mean±SD from multiple animals (n=5). Statistics shown is based on 2-way ANOVA.

FIG. 8D shows the data from the hippocampus (circle), brainstem (square), and striatum (triangle) in combination. Each data point represents an individual animal. A four-parameter, nonlinear fit is shown for the hippocampus (FIG. 8A) and the brainstem (FIG. 8B).

DETAILED DESCRIPTION OF THE DISCLOSURE

I. Definitions

Figures 1A, 1B:
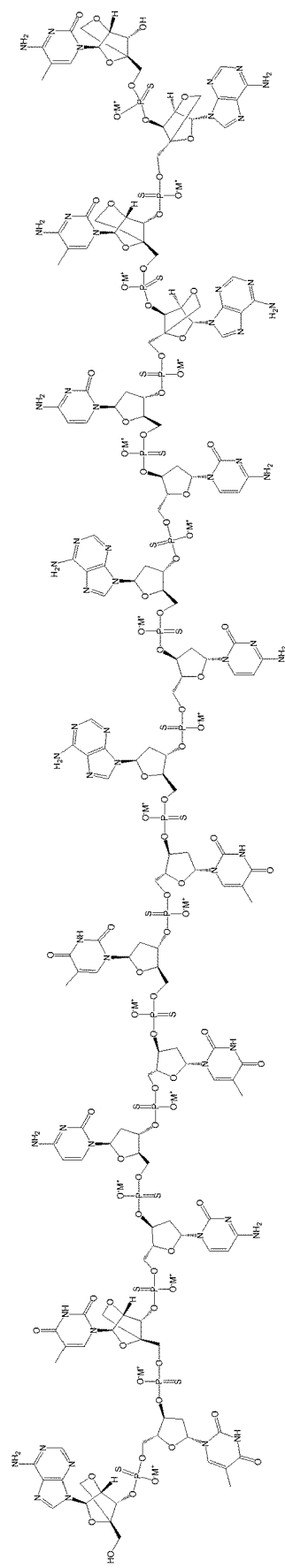
FIG. 1A shows the contiguous nucleotide sequence of ASO-005459. OxyA, OxyT, and Oxy MC are adenine beta D-oxy-LNA, thymine beta D-oxy-LNA, and methyl cytosine beta D-oxy-LNA, respectively; DNAt, DNAc, and DNAa are thymine DNA, cytosine DNA, and adenine DNA, respectively; and s is a phosphorothioate linkage.
FIG. 1B shows the molecular structure of ASO-005459 as disclosed herein. The provided structure has a molecular formula of $C_{171}H_{214}N_{56}O_{90}P_{16}S_{16}$ and each of the M+ is a pharmaceutically acceptable counterion such as $H^+$, $Na^+$, or $NH_4^+$.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower). For example, if it is stated that "the ASO reduces expression of SNCA protein in a cell following administration of the ASO by at least about 60%," it is implied that the SNCA levels are reduced by a range of 50% to 70%.

The term "antisense oligonucleotide" (ASO) refers to an oligomer or polymer of nucleosides, such as naturally-occurring nucleosides or modified forms thereof, that are covalently linked to each other through internucleotide linkages. The ASO useful for the disclosure includes at least one non-naturally occurring nucleoside. An ASO is complementary to a target nucleic acid, such that the ASO hybridizes to the target nucleic acid sequence. The terms "antisense ASO," "ASO," and "oligomer" as used herein are interchangeable with the term "ASO."

The term "nucleic acids" or "nucleotides" is intended to encompass plural nucleic acids. In some embodiments, the term "nucleic acids" or "nucleotides" refers to a target sequence, e.g., pre-mRNAs, mRNAs, or DNAs in vivo or in vitro. When the term refers to the nucleic acids or nucleotides in a target sequence, the nucleic acids or nucleotides can be naturally occurring sequences within a cell. In other embodiments, "nucleic acids" or "nucleotides" refer to a sequence in the ASOs of the disclosure. When the term refers to a sequence in the ASOs, the nucleic acids or nucleotides are not naturally occurring, i.e., chemically synthesized, enzymatically produced, recombinantly produced, or any combination thereof. In one embodiment, the nucleic acids or nucleotides in the ASOs are produced synthetically or recombinantly, but are not a naturally occurring sequence or a fragment thereof. In another embodiment, the nucleic acids or nucleotides in the ASOs are not naturally occurring because they contain at least one nucleotide analog that is not naturally occurring in nature. The term "nucleic acid" or "nucleoside" refers to a single nucleic acid segment, e.g., a DNA, an RNA, or an analog thereof, present in a polynucleotide. "Nucleic acid" or "nucleoside" includes naturally occurring nucleic acids or non-naturally occurring nucleic acids. In some embodiments, the terms "nucleotide", "unit" and "monomer" are used interchangeably. It will be recognized that when referring to a sequence of nucleotides or monomers, what is referred to is the sequence of bases, such as A, T, G, C or U, and analogs thereof.

The term "nucleotide" as used herein, refers to a glycoside comprising a sugar moiety, a base moiety and a covalently linked group (linkage group), such as a phosphate or phosphorothioate internucleotide linkage group, and covers both naturally occurring nucleotides, such as DNA or RNA, and non-naturally occurring nucleotides comprising modified sugar and/or base. Herein, a single nucleotide (unit) can also be referred to as a monomer or nucleic acid unit.

The term "nucleoside" as used herein is used to refer to a glycoside comprising a sugar moiety and a base moiety, which can be covalently linked by the internucleotide linkages between the nucleosides of the ASO. In the field of biotechnology, the term "nucleoside" is often used to refer to a nucleic acid monomer or unit. In the context of an ASO, the term "nucleoside" can refer to the base alone, i.e., a nucleobase sequence comprising cytosine (DNA and RNA), guanine (DNA and RNA), adenine (DNA and RNA), thymine (DNA) and uracil (RNA), in which the presence of the sugar backbone and internucleotide linkages are implicit. Likewise, particularly in the case of oligonucleotides where one or more of the internucleotide linkage groups are modified, the term "nucleotide" can refer to a "nucleoside." For example the term "nucleotide" can be used, even when specifying the presence or nature of the linkages between the nucleosides.

As one of ordinary skill in the art would recognize, the 5' terminal nucleotide of an oligonucleotide does not comprise a 5' internucleotide linkage group, although it can comprise a 5' terminal group.

The term "downstream," when referring to a nucleotide sequence, means that a nucleic acid or a nucleotide sequence is located 3' to a reference nucleotide sequence. In certain embodiments, downstream nucleotide sequences relate to sequences that follow the starting point of transcription. For example, the translation initiation codon of a gene is located downstream of the start site of transcription.

Unless otherwise indicated, the sequences provided herein are listed from 5' end (left) to 3' end (right).

The term "upstream" refers to a nucleotide sequence that is located 5' to a reference nucleotide sequence.

The term "transcript" as used herein can refer to a primary transcript that is synthesized by transcription of DNA and becomes a messenger RNA (mRNA) after processing, i.e., a precursor messenger RNA (pre-mRNA), and the processed mRNA itself. The term "transcript" can be interchangeably used with "pre-mRNA" and "mRNA." After DNA strands are transcribed to primary transcripts, the newly synthesized primary transcripts are modified in several ways to be converted to their mature, functional forms such as mRNA, tRNA, rRNA, lncRNA, miRNA and others. Thus, the term "transcript" can include exons, introns, 5' UTRs, and 3' UTRs.

The term "expression" as used herein refers to a process by which a polynucleotide produces a gene product, for example, a RNA or a polypeptide. It includes, without limitation, transcription of the polynucleotide into messenger RNA (mRNA) and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

The term "naturally occurring variant" of the SNCA polypeptide refers to variants of the SNCA polypeptide sequence or SNCA nucleic acid sequence (e.g., transcript) which exist naturally within the defined taxonomic group, such as mammalian, such as mouse, monkey, and human. Typically, when referring to "naturally occurring variants" of a SNCA polynucleotide the term can also encompass any allelic variant of the SNCA-encoding genomic DNA which is found at Chromosomal position 17q21 by chromosomal translocation or duplication, and the RNA, such as mRNA derived therefrom. "Naturally occurring variants" can also include variants derived from alternative splicing of the SNCA mRNA. When referenced to a specific polypeptide sequence, e.g., the term also includes naturally occurring forms of the protein, which can therefore be processed, e.g., by co- or post-translational modifications, such as signal peptide cleavage, proteolytic cleavage, glycosylation, etc.

The term "complement" as used herein indicates a sequence that is complementary to a reference sequence. It is well known that complementarity is the base principle of DNA replication and transcription as it is a property shared between two DNA or RNA sequences, such that when they are aligned antiparallel to each other, the nucleotide bases at each position in the sequences will be complementary, much like looking in the mirror and seeing the reverse of things. Therefore, for example, the complement of a sequence of 5' "ATGC" 3' can be written as 3' "TACG" 5' or 5' "GCAT" 3'. The terms "reverse complement", "reverse complementary" and "reverse complementarity" as used herein are interchangeable with the terms "complement", "complementary" and "complementarity." Therefore, the sequence of 5' attcctttacaccacac 3'(SEQ ID NO: 4) can be complementary to 5' gtgtggtgtaaaggaat 3'.

As used herein, a reference to a SEQ ID number (i.e., SEQ ID NO: 4) includes a particular nucleobase sequence, but does not include any design or full chemical structure. When this specification refers to a specific ASO number (i.e., ASO-005459), the reference includes the sequence, the specific ASO design, and the chemical structure.

"Potency" is normally expressed as an $IC_{50}$ or $EC_{50}$ value, in μM, nM or pM unless otherwise stated. Potency can also be expressed in terms of percent inhibition. $IC_{50}$ is the median inhibitory concentration of a therapeutic molecule. $EC_{50}$ is the median effective concentration of a therapeutic molecule relative to a vehicle or control (e.g., saline). In functional assays, $IC_{50}$ is the concentration of a therapeutic molecule that reduces a biological response, e.g., transcription of mRNA or protein expression, by 50% of the biological response that is achieved by the therapeutic molecule. In functional assays, $EC_{50}$ is the concentration of a therapeutic molecule that produces 50% of the biological response, e.g., transcription of mRNA or protein expression. $IC_{50}$ or $EC_{50}$ can be calculated by any number of means known in the art.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals including, e.g., humans, non-human primates, dogs, cats, guinea pigs, rabbits, rats, mice, horses, cattle, bears, and so on.

The term "pharmaceutical composition" refers to a preparation which is in such form as to permit the biological activity of the active ingredient to be effective, and which contains no additional components which are unacceptably toxic to a subject to which the composition would be administered. Such composition can be sterile.

An "effective amount" of an ASO as disclosed herein is an amount sufficient to carry out a specifically stated purpose. An "effective amount" can be determined empirically and in a routine manner, in relation to the stated purpose.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for a disease or condition disclosed elsewhere herein according to the methods provided herein if the patient shows, e.g., total, partial, or transient alleviation or elimination of symptoms associated with the disease or disorder.

II. ASO-005459

The ASO of the disclosure (i.e., ASO-005459) comprises a contiguous nucleotide sequence of 17 nucleotides in length, which corresponds to the complement of a region (i.e., junction between intron 1 and exon 2) of SNCA transcript, i.e., nucleotides 7,604-7,620 of SEQ ID NO: 1. The ASO of the disclosure has the nucleotide sequence as set forth in SEQ ID NO: 4 (i.e., attcctttacaccacac) with an ASO design of LDLDDDDDDDDDDDLLLL (i.e., AtTccttttacac-cACAC), wherein the L indicates a locked nucleic acid nucleoside (i.e., LNA, e.g., beta-D-oxy-LNA) and the D indicates a deoxyribonucleic acid (DNA). Accordingly, the $1^{st}$, $3^{rd}$ and the $14^{th}$-$17^{th}$ nucleotides from the 5' end of ASO-005459 is beta-D-oxy-LNA and each of the other nucleotides is, DNA. The ASO disclosed herein also has the following chemical structure: OxyAs DNAts OxyTs DNAcs DNAcs DNAts DNAts DNAts DNAas DNAcs DNAas DNAcs DNAcs OxyAs OxyMCs OxyAs OxyMC, wherein "s" indicates a phosphorothioate linkage. The structural formula for ASO-005459 is provided in FIG. 1B, wherein M+ is a pharmaceutically acceptable counterion. The term "pharmaceutically acceptable counterion," as used herein," refers to an ion that accompanies an ionic species in order to maintain electric neutrality that is not biologically or otherwise undesirable and thereby, allowing for the production of a pharmaceutically acceptable salt form. Accordingly, in some embodiments, pharmaceutically acceptable counterion can be $H^+$, $Na^+$, $K^+$, $NH_4^+$, $Li^+$, or any other cation with a charge of $1^+$. In some embodiments, the pharmaceutically acceptable counterion is $H^+$, $Na^+$, $NH_4^+$, and combinations thereof.

The term "pharmaceutically acceptable salts" as used herein refers to derivatives of ASO-005459 wherein the ASO-005459 is modified (e.g., addition of a cation disclosed herein) by making salts thereof. Such salts retain the desired biological activity of the ASO without imparting undesired toxicological effects. The ASO of the disclosure can be in any salt form. In some embodiments, the ASO of the disclosure is in the form of a sodium salt. In other embodiments, the ASO is in the form of a potassium salt.

ASO-005459 can bind to intron1/exon2 junction of SNCA mRNA and prevent translation of SNCA mRNA. In some embodiments, because of the sugar modification, the ASO of the disclosure has a binding affinity to a target RNA sequence that is enhanced by at least 5%, at least 10%, at least 20%, at least 30%, at least 40%, at least 50%, at least 60%, at least 70%, at least 80%, at least 90%, or at least 100% compared to a control (e.g., an ASO without such sugar modification).

The monomers of the ASO described herein are coupled together via linkage groups. Suitably, each monomer is linked to the 3' adjacent monomer via a linkage group.

The person having ordinary skill in the art would understand that, in the context of the present disclosure, the 5' monomer at the end of an ASO does not comprise a 5' linkage group, although it may or may not comprise a 5' terminal group.

The terms "linkage group" and "internucleotide linkage" are intended to mean a group capable of covalently coupling together two nucleotides. Examples include phosphate groups and phosphorothioate groups.

Examples of internucleotide linkages include phosphodiester linkage, a phosphotriester linkage, a methylphosphonate linkage, a phosphoramidate linkage, a phosphorothioate linkage, and combinations thereof. See also WO2007/031091, which is hereby incorporated by reference in its entirety.

In one aspect of the ASO of the disclosure, the nucleotides are linked to each other by means of phosphorothioate groups.

It is recognized that the inclusion of phosphodiester linkages, such as one or two linkages, into an otherwise phosphorothioate ASO, particularly between or adjacent to nucleotides can modify the bioavailability and/or bio-distribution of an ASO—see WO2008/113832, hereby incorporated by reference.

In some embodiments, such as the embodiments referred to above, where suitable and not specifically indicated, all remaining linkage groups are either phosphodiester or phosphorothioate, or a mixture thereof.

In some embodiments, all the internucleotide linkage groups are phosphorothioate.

A "LNA nucleoside" is a 2'-modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81, and Mitsuoka et al., Nucleic Acids Research 2009, 37(4), 1225-1238, and Wan and Seth, J. Medical Chemistry 2016, 59, 9645-9667.

Further non limiting, exemplary LNA nucleosides are disclosed in Scheme 1.

Scheme 1

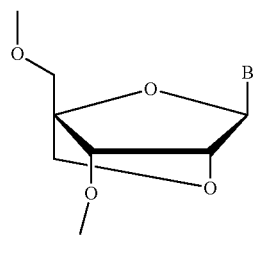

β-D-oxy LNA

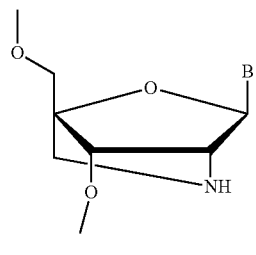

β-D-amino LNA

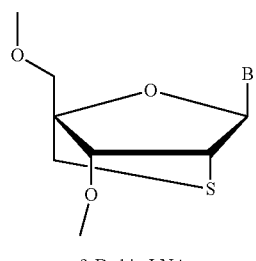

β-D-thio LNA

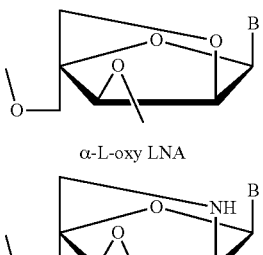

α-L-oxy LNA

α-L-amino LNA

-continued

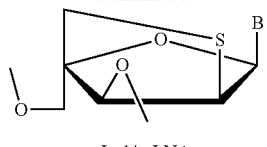

α-L-thio LNA

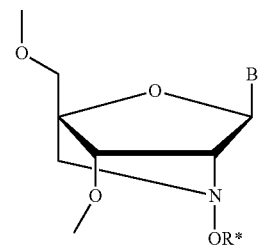

β-D-amino substituted LNA

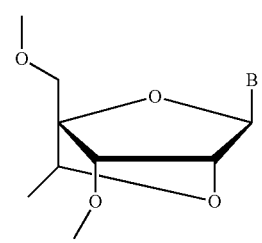

6' methyl β-D-oxy LNA

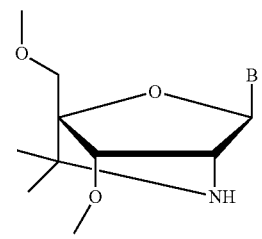

6' dimethyl β-D-oxy LNA

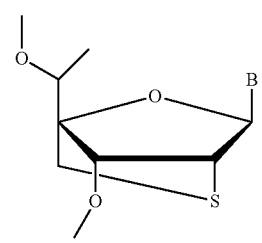

5' methyl β-D-oxy LNA

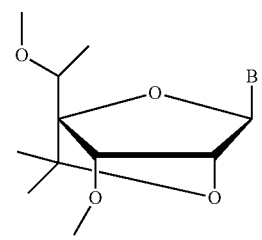

5' methyl, 6'dimethyl β-D-oxy LNA

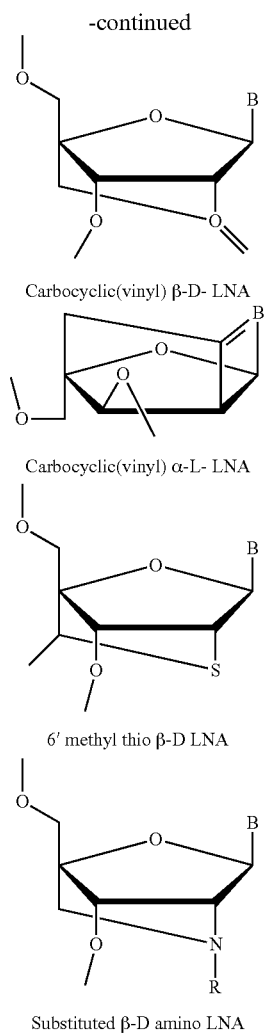

Carbocyclic(vinyl) β-D- LNA

Carbocyclic(vinyl) α-L- LNA

6' methyl thio β-D LNA

Substituted β-D amino LNA

In a particular embodiment, the LNA useful for the disclosure is beta-D-oxy-LNA.

IIA. Conjugates

The term conjugate as used herein refers to ASO-005459 covalently linked to a non-nucleotide moiety.

Conjugation of ASO-005459 to one or more non-nucleotide moieties may improve the pharmacology of the ASO, e.g., by affecting the activity, cellular distribution, cellular uptake or stability of the ASO. In some embodiments the conjugate moiety modify or enhance the pharmacokinetic properties of the ASO by improving cellular distribution, bioavailability, metabolism, excretion, permeability, and/or cellular uptake of the ASO. In particular the conjugate may target the ASO to a specific organ, tissue or cell type and thereby enhance the effectiveness of the ASO in that organ, tissue or cell type. At the same time the conjugate can serve to reduce activity of the ASO in non-target cell types, tissues or organs, e.g., off target activity or activity in non-target cell types, tissues or organs. WO 93/07883 and WO2013/033230 provide suitable conjugate moieties. Further suitable conjugate moieties are those capable of binding to the asialoglycoprotein receptor (ASGPr). In particular tri-valent N-acetylgalactosamine conjugate moieties are suitable for binding to the ASGPr, see for example WO 2014/076196, WO 2014/207232, and WO 2014/179620.

ASO conjugates and their synthesis have also been reported in comprehensive reviews by Manoharan in Antisense Drug Technology, Principles, Strategies, and Applications, S. T. Crooke, ed., Ch. 16, Marcel Dekker, Inc., 2001 and Manoharan, *Antisense and Nucleic Acid Drug Development,* 2002, 12, 103.

In some embodiments, the non-nucleotide moiety (conjugate moiety) is selected from the group consisting of carbohydrates, cell surface receptor ligands, drug substances, hormones, lipophilic substances, polymers, proteins, peptides, toxins (e.g., bacterial toxins), vitamins, viral proteins (e.g., capsids), and combinations thereof.

IIB. Activated ASOs

The term "activated ASO," as used herein, refers to an ASO of the disclosure that is covalently linked (i.e., functionalized) to at least one functional moiety that permits covalent linkage of the ASO to one or more conjugated moieties, i.e., moieties that are not themselves nucleic acids or monomers, to form the conjugates herein described. Typically, a functional moiety will comprise a chemical group that is capable of covalently bonding to the ASO via, e.g., a 3-hydroxyl group or the exocyclic $NH_2$ group of the adenine base, a spacer that can be hydrophilic and a terminal group that is capable of binding to a conjugated moiety (e.g., an amino, sulfhydryl or hydroxyl group). In some embodiments, this terminal group is not protected, e.g., is an $NH_2$ group. In other embodiments, the terminal group is protected, for example, by any suitable protecting group such as those described in "Protective Groups in Organic Synthesis" by Theodora W Greene and Peter G M Wuts, 3rd edition (John Wiley & Sons, 1999).

In some embodiments, ASO-005459 is functionalized at the 5' end in order to allow covalent attachment of the conjugated moiety to the 5' end of the ASO. In other embodiments, the ASO of the disclosure can be functionalized at the 3' end. In still other embodiments, the ASO of the disclosure can be functionalized along the backbone or on the heterocyclic base moiety. In yet other embodiments, the ASO of the disclosure can be functionalized at more than one position independently selected from the 5' end, the 3' end, the backbone, and the base.

In some embodiments, activated ASO of the disclosure is synthesized by incorporating during the synthesis one or more monomers that is covalently attached to a functional moiety. In other embodiments, activated ASO of the disclosure is synthesized with monomers that have not been functionalized, and the ASO is functionalized upon completion of synthesis.

III. Pharmaceutical Compositions and Administration Routes

ASO-005459 can be used in pharmaceutical formulations and compositions. Suitably, such compositions comprise a pharmaceutically acceptable diluent, carrier, salt, or adjuvant.

ASO-005459 can be included in a unit formulation such as in a pharmaceutically acceptable carrier or diluent in an amount sufficient to deliver to a patient a therapeutically effective amount without causing serious side effects in the treated patient. However, in some forms of therapy, serious side effects may be acceptable in terms of ensuring a positive outcome to the therapeutic treatment.

The formulated drug can comprise pharmaceutically acceptable binding agents and adjuvants. Capsules, tablets, or pills can contain for example the following compounds: microcrystalline cellulose, gum or gelatin as binders; starch or lactose as excipients; stearates as lubricants; various sweetening or flavoring agents. For capsules, the dosage unit may contain a liquid carrier like fatty oils. Likewise, coatings of sugar or enteric agents may be part of the dosage unit. The oligonucleotide formulations can also be emulsions of the active pharmaceutical ingredients and a lipid forming a micellular emulsion.

The pharmaceutical compositions of the present disclosure can be administered in a number of ways depending upon whether local or systemic treatment is desired and upon the area to be treated. Administration can be (a) oral (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal, intra-cerebroventricular, or intraventricular, administration. In one embodiment ASO-005459 is administered IV, IP, orally, topically or as a bolus injection or administered directly in to the target organ. In some embodiments, ASO-005459 is administered intrathecal or intra-cerebroventricular as a bolus injection.

Pharmaceutical compositions and formulations for topical administration can include transdermal patches, ointments, lotions, creams, gels, drops, sprays, suppositories, liquids, and powders. Conventional pharmaceutical carriers, aqueous, powder or oily bases, thickeners and the like may be necessary or desirable. Examples of topical formulations include those in which ASO-005459 is in admixture with a topical delivery agent such as lipids, liposomes, fatty acids, fatty acid esters, steroids, chelating agents, and surfactants. Compositions and formulations for oral administration include but are not limited to powders or granules, microparticulates, nanoparticulates, suspensions or solutions in water or non-aqueous media, capsules, gel capsules, sachets, tablets, or minitablets. Compositions and formulations for parenteral, intrathecal, intra-cerebroventricular, or intraventricular administration can include sterile aqueous solutions which can also contain buffers, diluents and other suitable additives such as, but not limited to, penetration enhancers, carrier compounds, and other pharmaceutically acceptable carriers or excipients.

Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids. Delivery of drug to the target tissue can be enhanced by carrier-mediated delivery including, but not limited to, cationic liposomes, cyclodextrins, porphyrin derivatives, branched chain dendrimers, polyethylenimine polymers, nanoparticles and microspheres (Dass C R. *J Pharm Pharmacol* 2002; 54(1):3-27).

The pharmaceutical formulations of the present disclosure, which can conveniently be presented in unit dosage form, can be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

For parenteral, subcutaneous, intradermal or topical administration the formulation can include a sterile diluent, buffers, regulators of tonicity and antibacterials. The active ASOs can be prepared with carriers that protect against degradation or immediate elimination from the body, including implants or microcapsules with controlled release properties. For intravenous administration the carriers can be physiological saline or phosphate buffered saline. International Publication No. WO2007/031091 (A2), published Mar. 22, 2007, further provides suitable pharmaceutically acceptable diluent, carrier and adjuvants—which are hereby incorporated by reference.

IV. Diagnostics

This disclosure further provides a diagnostic method useful during diagnosis of SNCA related diseases, e.g., a synucleinopathy. Non-limiting examples of synucleinopathy include, but are not limited to, Parkinson's disease, Parkinson's Disease Dementia (PDD), dementia with Lewy bodies, and multiple system atrophy.

ASO-005459 can be used to measure expression of SNCA transcript in a tissue or body fluid from an individual and comparing the measured expression level with a standard SNCA transcript expression level in normal tissue or body fluid, whereby an increase in the expression level compared to the standard is indicative of a disorder treatable by ASO-005459.

ASO-005459 can be used to assay SNCA transcript levels in a biological sample using any methods known to those of skill in the art. (Touboul et. al., *Anticancer Res.* (2002) 22 (6A): 3349-56; Verjout et. al., *Mutat. Res.* (2000) 640: 127-38); Stowe et. al., *J. Virol. Methods* (1998) 75 (1): 93-91).

By "biological sample" is intended any biological sample obtained from an individual, cell line, tissue culture, or other source of cells potentially expressing SNCA transcript. Methods for obtaining tissue biopsies and body fluids from mammals are well known in the art.

V. Kits Comprising ASO

This disclosure further provides kits that comprise ASO-005459 described herein and that can be used to perform the methods described herein. In certain embodiments, a kit comprises at least ASO-005459 in one or more containers. In some embodiments, the kits contain all of the components necessary and/or sufficient to perform a detection assay, including all controls, directions for performing assays, and any necessary software for analysis and presentation of results. One skilled in the art will readily recognize that ASO-005459 can be readily incorporated into one of the established kit formats which are well known in the art.

VI. Methods of Using

ASO-005459 can be utilized for therapeutics and prophylaxis. SNCA is a 140 amino acid protein preferentially expressed in neurons at pre-synaptic terminals where it is thought to play a role in regulating synaptic transmission. It has been proposed to exist natively as both an unfolded monomer and a stable tetramer of α-helices and has been shown to undergo several posttranslational modifications. One modification that has been extensively studied is phosphorylation of SNCA at amino acid serine 129 (S129). Normally, only a small percentage of SNCA is constitutively phosphorylated at S129 (pS129), whereas the vast majority of SNCA found in pathological intracellular inclusions is pS129 SNCA. These pathological inclusions consist of aggregated, insoluble accumulations of misfolded SNCA proteins and are a characteristic feature of a group of neurodegenerative diseases collectively known as synucleinopathies (or α-synucleinopathies).

In synucleinopathies, SNCA can form pathological aggregates in neurons known as Lewy bodies, which are characteristic of both Parkinson's Disease (PD), Parkinson's Disease Dementia (PDD), and dementia with Lewy bodies (DLB). ASO-005459 therefore can reduce the number of the SNCA pathological aggregates or prevent formation of the SNCA pathological aggregates. Additionally, abnormal SNCA-rich lesions called glial cytoplasmic inclusions (GCIs) are found in oligodendrocytes, and represent the hallmark of a rapidly progressing, fatal synucleinopathy known as multiple systems atrophy (MSA). In some embodiments, ASO-005459 reduces the number of GCIs or prevents formation of GCIs. Reports of either undetectable or low levels of SNCA mRNA expression in oligodendrocytes suggest that some pathological form of SNCA is propagated from neurons, where it is highly expressed, to oligodendrocytes. In certain embodiments, ASO-005459 reduces or prevents propagation of SNCA, e.g., pathological form of SNCA, from neurons.

ASO-005459 can be used in research, e.g., to specifically inhibit the synthesis of SNCA protein (typically by degrading or inhibiting the mRNA and thereby prevent protein formation) in cells and experimental animals thereby facilitating functional analysis of the target or an appraisal of its usefulness as a target for therapeutic intervention. Further provided are methods of down-regulating the expression of SNCA mRNA and/or SNCA protein in cells or tissues comprising contacting the cells or tissues, in vitro or in vivo, with an effective amount of ASO-005459, conjugates, or compositions of the disclosure.

For therapeutics, an animal or a human, suspected of having a disease or disorder, which can be treated by modulating the expression of SNCA transcript and/or SNCA protein is treated by administering ASO-005459 in accordance with this disclosure. Further provided are methods of treating a mammal, such as treating a human, suspected of having or being prone to a disease or condition, associated with expression of SNCA transcript and/or SNCA protein by administering a therapeutically or prophylactically effective amount of ASO-005459 or compositions of the disclosure. The ASO, a conjugate, or a pharmaceutical composition according to the disclosure is typically administered in an effective amount. In some embodiments, the ASO or conjugate of the disclosure is used in therapy.

The disclosure further provides for ASO-005459 for use in treating one or more of the diseases referred to herein, such as a disease selected from the group consisting of Parkinson's disease, Parkinson's Disease Dementia (PDD), dementia with Lewy bodies, multiple system atrophy, and any combinations thereof.

The disclosure further provides for a method for treating α-synucleinopathies, the method comprising administering an effective amount of the ASO, conjugates, or pharmaceutical compositions thereof to an animal in need thereof (such as a patient in need thereof).

In certain embodiments, the disease, disorder, or condition is associated with overexpression of SNCA gene transcript and/or SNCA protein.

The disclosure also provides for methods of inhibiting (e.g., by reducing) the expression of SNCA gene transcript and/or SNCA protein in a cell or a tissue, the method comprising contacting the cell or tissue, in vitro or in vivo, with an effective amount of the ASO, conjugates, or pharmaceutical compositions thereof, of the disclosure to affect degradation of expression of SNCA gene transcript thereby reducing SNCA protein.

In certain embodiments, ASO-005459 is used to reduce the expression of SNCA mRNA in one or more sections of brain, e.g., hippocampus, brainstem, striatum, or any combinations thereof. In other embodiments, ASO-005459 reduces the expression of SNCA mRNA, e.g., in brain stem and/or striatum, less than 70%, less than 60%, less than 50%, less than 40%, less than 30%, less than 20%, less than 10%, or less than 5% compared to the SNCA mRNA expression after administration of or exposure to a vehicle (no ASO), at day 3, day 5, day 7, day 10, day 14, day 15, day 20, day 21, or day 25. In some embodiments, the expression of SNCA mRNA is maintained below 70%, below 60%, below 50%, below 40%, below 30%, below 20%, below 10%, or below 5% compared to the SNCA mRNA expression after administration of or exposure to a vehicle (no ASO) until day 28, day 30, day 32, day 35, day 40, day 42, day 45, day 49, day 50, day 56, day 60, day 63, day 70, or day 75.

In other embodiments, ASO-005459 reduces SNCA mRNA and/or SNCA protein expression in medulla, caudate putamen, pons cerebellum, lumbar spinal cord, frontal cortex, and/or any combinations thereof.

The disclosure also provides for the use of ASO-005459 or a conjugate of the disclosure as described for the manufacture of a medicament. The disclosure also provides for a composition comprising ASO-005459 or a conjugate thereof for use in treating a disorder as referred to herein, or for a method of the treatment of as a disorder as referred to herein. The present disclosure also provides ASO-005459 or the conjugates for use in therapy. The present disclosure additionally provides ASO-005459 or the conjugates for use in the treatment of synucleinopathy.

The disclosure further provides for a method for inhibiting SNCA protein in a cell which is expressing SNCA comprising administering ASO-005459 or a conjugate according to the disclosure to the cell so as to affect the inhibition of SNCA protein in the cell.

The disclosure includes a method of reducing, ameliorating, preventing, or treating neuronal hyperexcitability in a subject in need thereof comprising administering ASO-005459 or a conjugate according to the disclosure.

The disclosure also provides for a method for treating a disorder as referred to herein the method comprising administering ASO-005459 or a conjugate according to the disclosure as herein described and/or a pharmaceutical composition according to the disclosure to a patient in need thereof.

ASO-005459 and other compositions according to the disclosure can be used for the treatment of conditions associated with over expression or expression of mutated version of SNCA protein.

The disclosure provides for ASO-005459 or the conjugate according to disclosure, for use as a medicament, such as for the treatment of α-Synucleinopathies. In some embodiments the α-Synucleinopathy is a disease selected from the group consisting of Parkinson's disease, Parkinson's Disease Dementia (PDD), dementia with Lewy bodies, multiple system atrophy, and any combinations thereof.

The disclosure further provides use of ASO-005459 in the manufacture of a medicament for the treatment of a disease, disorder or condition as referred to herein. In some embodiments, ASO-005459 or a conjugate thereof is used for the manufacture of a medicament for the treatment of a α-Synucleinopathy, a seizure disorder, or a combination thereof.

Generally stated, one aspect of the disclosure is directed to a method of treating a mammal suffering from or susceptible to conditions associated with abnormal levels of SNCA (i.e., a α-synucleinopathy), comprising administering to the mammal a therapeutically effective amount of the ASO as described herein.

The disease or disorder, as referred to herein, can, in some embodiments, be associated with a mutation in the SNCA gene or a gene whose protein product is associated with or interacts with SNCA protein. Therefore, in some embodiments, the target mRNA is a mutated form of the SNCA sequence.

An interesting aspect of the disclosure is directed to the use of ASO-005459 as defined herein or a conjugate as defined herein for the preparation of a medicament for the treatment of a disease, disorder or condition as referred to herein.

The methods of the disclosure can be employed for treatment or prophylaxis against diseases caused by abnormal levels of SNCA protein. In some embodiments, diseases caused by abnormal levels of SNCA protein are α-synucleinopathies. In certain embodiments, α-synucleinopathies include Parkinson's disease, Parkinson's Disease Dementia (PDD), dementia with Lewy bodies, and multiple system atrophy.

Alternatively stated, in some embodiments, the disclosure is furthermore directed to a method for treating abnormal levels of SNCA protein, the method comprising administering ASO-005459, or a conjugate of the disclosure, or a pharmaceutical composition of the disclosure to a patient in need thereof.

The disclosure also relates to ASO-005459, a composition or a conjugate as defined herein for use as a medicament.

The disclosure further relates to use of a compound, composition, or a conjugate as defined herein for the manufacture of a medicament for the treatment of abnormal levels of SNCA protein or expression of mutant forms of SNCA protein (such as allelic variants, such as those associated with one of the diseases referred to herein).

A patient who is in need of treatment is a patient suffering from or likely to suffer from the disease or disorder.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); Crooke, Antisense drug Technology: Principles, Strategies and Applications, $2^{nd}$ Ed. CRC Press (2007) and in Ausubel et al. (1989) Current Protocols in Molecular Biology (John Wiley and Sons, Baltimore, Md.).

All of the references cited above, as well as all references cited herein, are incorporated herein by reference in their entireties.

The following examples are offered by way of illustration and not by way of limitation.

EXAMPLES

Example 1: Construction of ASO-005459

The ASO described herein (i.e., ASO-005459) was designed to target the junction between intron 1 and exon 2 of SNCA pre-mRNA (i.e., nucleotides 7,604 to 7,620 of SEQ ID NO: 1). ASO-005459 was designed to be a gapmer (e.g., alternating gapmer) and contains locked nucleic acids—LNAs (upper case letters), beta-deoxy LNA at the 5' end and the 3' end, and a phosphorothioate backbone. But the backbone can be other types of backbones (e.g., a phosphodiester linkage, a phosphotriester linkage, a methylphosphonate linkage, a phosphoramidate linkage, or combinations thereof).

The ASO of the present disclosure was synthesized using methods well known in the art. Exemplary methods of preparing such ASOs are described in Barciszewski et al., Chapter 10—"Locked Nucleic Acid Aptamers" in *Nucleic Acid and Peptide Aptamers: Methods and Protocols*, vol. 535, Gunter Mayer (ed.) (2009), the entire contents of which is hereby expressly incorporated by reference herein.

Example 2. High Content Assay to Measure Reduction of SNCA Protein in Primary Neurons ASO-005459 was tested for its ability to reduce SNCA protein expression in primary mouse neurons. The primary neuronal cultures were established from the forebrain of PAC-Tg(SNCA$^{A53T}$)$^{+/+}$; SNCA$^{-/-}$ ("PAC-A53T") mice carrying the entire human SNCA gene with a A53T mutation on a mouse SNCA knockout background. See Kuo Y et al., *Hum Mol Genet.*, 19: 1633-50 (2010). All procedures involving mice were conducted according to Animal Test Methods (ATM) approved by the Bristol-Myers Squibb Animal Care and Use Committee (ACUC). Primary neurons were generated by papain digestion according to manufacturer's protocol (Worthington Biochemical Corporation, LK0031050). Isolated neurons were washed and resuspended in Neurobasal medium (NBM, Invitrogen) supplemented with B27 (Gibco), 1.25 µM Glutamax (Gibco), 100 unit/ml penicillin, 100 µg/ml streptomycin, and 25 µg/ml Amphotericin B.

Cells were plated on multi-well poly D-Lysine coated plates at 5,400 cells/cm$^2$ (for example in 384 well plates 6,000 cells/well in 25 µl NBM). The ASO was diluted in water and added to the cells at DIV01 (i.e., 1 day post plating). The ASO was added to 2× final concentration in medium then delivered to cells manually. Alternatively, the ASO in water was dispensed using a Labcyte ECHO acoustic dispenser. For ECHO dispense, 250 nl of ASO in water was added to cells in medium followed by the addition of an equal volume aliquot of fresh aliquot of NBM. For primary screening, the ASO was added to final concentrations of 5 µM, 3.3 µM, 1 µM, 200 nM, or 40 nM. For potency determination, 8-10 point titrations of the ASO was prepared from 0.75 mM stock then delivered to cultured cells for a final concentration range of 2.7-4000 nM or 4.5-10,000 nM. ASO-000010 (TCTgtcttggctTTG, SEQ ID NO: 5) and ASO-000838 (AGAaataagtggtAGT, SEQ ID NO: 6) (5 µM) were included in each plate as reference control inhibitors for tubulin and SNCA, respectively. The cells were incubated with the ASOs for 14 days to achieve steady state reduction of mRNA.

After the 14-day incubation, the cells were fixed by the addition of fixative to final concentrations of 4% formaldehyde (J.T. Baker) and 4% sucrose (Sigma) in the wells. The cells were fixed for 15 minutes, and then, the fixative aspirated from the wells. Then, the cells were permeabilized for 20 minutes with a phosphate buffered saline (PBS) solution containing 0.3% Triton-X 100 and 3% bovine serum albumin (BSA) or 3% Normal goat serum. Afterwards, the permeabilization buffer was aspirated from the wells, and the cells were washed once with PBS. The primary antibodies were then diluted in PBS containing 0.1% Triton X-100 and 3% BSA. Dilutions of 1:1000 of rabbit anti-SNCA (Abcam) and 1:500 of chicken anti-tubulin (Abcam) were used. Cells were incubated with the primary antibodies between 2 hours to overnight. Following the incubation, the primary antibody staining solution was aspirated, and the cells were washed 2-times with PBS. A secondary staining solution containing 1:500 dilution of goat-anti-chicken Alexa 567 antibody, goat anti-rabbit-Alexa 488 antibody, and Hoechst (10 µg/ml) in PBS containing 0.1% Triton X-100 with 3% BSA was added to the wells, and the plates were incubated for 1 hour. Afterwards, the secondary staining solution was aspirated from the wells, and the cells were washed 3-times with PBS. After washing the cells, 60 µl of PBS was added to each well. Plates were then stored in the PBS until imaging.

For imaging, the plates were scanned on a Thermo-Fisher (Cellomics) CX5 imager using the Spot Detector bio-application (Cellomics) to quantify nuclei (Hoechst stain, Channel 1), tubulin extensions (Alexa 567, channel 2) and SNCA (Alexa 488, channel 3). Object count (nuclei) was monitored but not published to the database. The total area covered by tubulin was quantified as the feature SpotTotalAreaCh2 and total intensity of staining for SNCA quantified as SpotTotalIntenCh3. The tubulin measure was included to monitor toxicity. To determine the reduction of SNCA protein, the ratio of SNCA intensity to the tubulin staining area was calculated and results normalized as % inhibition median using the median of vehicle treated wells as total and ASO-000010 or ASO-000838 wells as maximally inhibited wells for tubulin or SNCA, respectively.

Example 3: QUANTIGENE® Analysis (96-Well Assay) to Measure mRNA Reduction in Human Neurons The ability of ASO-005459 to reduce human SNCA mRNA and/or possible human off target mRNA species was measured in vitro by QUANTIGENE® analysis. Human neurons (Cellular Dynamics Inc., "iNeurons"), were thawed, plated, and cultured per manufacturer's specifications. These iNeurons are highly pure population of human neurons derived from induced pluripotent stem (iPS) cells using Cellular Dynamic's proprietary differentiation and purification protocols.

Lysis: Cells were plated on poly-L-ornithine/laminin coated 96-well plates at 50,000 to 100,000 cells per well (dependent on the expression of the off target being investigated) and maintained in Neurobasal media supplemented with B27, glutamax, and Penicillin-Streptomycin. The ASO was diluted in water and added to cells at DIV01 (i.e., 1 day post plating). For single point measurements, a final ASO concentration of 0.5 µM was typically used. For $IC_{50}$ determinations, the neurons were treated with a seven-point concentration response dilution of 1:4, with the highest concentration as 5 µM to define the $IC_{50}$. The cells were then incubated at 37° C. and 5% $CO_2$ for 6 days to achieve steady state reduction of mRNA.

After the incubation, the media was removed and cells were washed 1× in DPBS and lysed as follows. Measurement of lysate messenger RNA was performed using the QUANTIGENE® 2.0 Reagent System (AFFYMETRIX®), which quantitates RNA using a branched DNA-signal amplification method reliant on the specifically designed RNA capture probe set. The working cell lysis buffer solution was made by adding 50 µl proteinase K to 5 ml of pre-warmed (37° C.) Lysis mix and diluted in $dH_2O$ to a 1:4 final dilution. The working lysis buffer was added to the plates (100 to 150 µl/well, depending on the expression of the off target being investigated), triturated 10 times, sealed and incubated for 30 min at 55° C. Following the lysis, the wells were triturated 10 more times, and the plates were stored at −80° C. or assayed immediately.

Assay: Depending on the specific capture probe used (i.e., SNCA, PROS1, or tubulin), the lysates were diluted (or not diluted) in the lysis mix. Then, the lysates were added to the capture plates (96-well polystyrene plate coated with capture probes) at a total volume of 80 µl/well. Working probe sets reagents were generated by combining nuclease-free water (12.1 µl), lysis mixture (6.6 µl), blocking reagent (1 µl), and specific 2.0 probe set (0.3 µl) (human SNCA catalogue #SA-50528, human PROS1 catalogue #SA-10542, or human beta 3 tubulin catalogue #SA-15628) per manufacturer's instructions (QUANTIGENE® 2.0 AFFYMETRIX®). Next, 20 µl working probe set reagents were added to 80 µl lysate dilution (or 80 µl lysis mix for background samples) on the capture plate. Plates were centrifuged at 240 g for 20 seconds and then incubated for 16-20 hours at 55° C. to hybridize (target RNA capture).

Signal amplification and detection of target RNA began by washing plates with buffer 3 times (300 µl/well) to remove any unbound material. Next, the 2.0 Pre-Amplifier hybridization reagent (100 µl/well) was added, incubated at 55° C. for 1 hour, then aspirated, and wash buffer was added and aspirated 3 times. The 2.0 Amplifier hybridization reagent was then added as described (100 µl/well), incubated for 1 hour at 55° C. and the wash step repeated as described previously. The 2.0 Label Probe hybridization reagent was added next (100 µl/well), incubated for 1 hour at 50° C. and the wash step was repeated as described previously. The plates were again centrifuged at 240 g for 20 seconds to remove any excess wash buffer and then, the 2.0 Substrate was added (100 µl/well) to the plates. Plates were incubated for 5 minutes at room temperature and then, the plates were imaged on a PerkinElmer Envision multilabel reader in luminometer mode within 15 minutes.

Data determination: For the gene of interest, the average assay background signal was subtracted from the average signal of each technical replicate. The background-subtracted, average signals for the gene of interest were then normalized to the background-subtracted average signal for the housekeeping tubulin RNA. The percent inhibition for the treated sample was calculated relative to the control treated sample lysate. Results of QUANTIGENE® assays for cells treated with the ASOs are shown in e.g., FIG. 3.

Example 4: QUANTIGENE® Analysis (96-Well Assay) to Measure mRNA Reduction in Ramos Cells To measure possible human off target IKZF3 (IKAROS family zinc finger 3) mRNA reduction, Ramos cells (a human lymphocytic cell line) were used. Since Ramos cells do not express SNCA, RB1 (RB transcriptional corepressor 1), which is expressed in Ramos cells, was used as a positive control for assessing ASO-mediated knockdown IKZF3 mRNA expression. Two ASOs were synthesized to bind to and knockdown human RB1 mRNA expression. Beta-2 microglobulin (02M) was used as a housekeeping gene control. The Ramos cells were grown in suspension in RPMI media supplemented with FBS, glutamine, and Pen/Strep.

Lysis: Cells were plated on poly-L-ornithine/laminin coated 96 well plates at 20,000 cells per well and maintained in Neurobasal media containing B27, glutamax and Penicillin-Streptomycin. The ASO was diluted in water and added to cells at 1 day post plating (DIV01) to a final concentration of 1 µM. Following ASO treatment, the cells were incubated at 37° C. for 4 days to achieve steady state reduction of mRNA. After the incubation, the media was removed and cells lysed as follows. Measurement of lysate messenger RNA was performed using the QUANTIGENE® 2.0 Reagent System (AFFYMETRIX®), which quantitated RNA using a branched DNA-signal amplification method reliant on the specifically designed RNA capture probe set. Lysis mix (QUANTIGENE®2.0 AFFYMETRIX®) was pre-warmed in an incubator at 37° C. for 30 minutes. For lysing cells in suspension, 100 µl of 3× Lysis Buffer (with 10 µl/ml proteinase K) was added to 200 µl of cells in suspension. The cells were then triturated 10 times to lyse, and the plate sealed and incubated for 30 min at 55° C. Afterwards, the lysates were stored at −80° C. or assayed immediately.

Assay: Depending on the specific capture probe used (i.e., IKZF3, RB1, and β2M), the lysates were diluted (or not diluted) in the lysis mix. Then, the lysates were added to the capture plate (96 well polystyrene plate coated with capture probes) at a total volume of 80 µl/well. Working probe sets reagents were generated by combining nuclease-free water 12.1 µl, lysis mixture 6.6 µl, blocking reagent 1 µl, specific 2.0 probe set 0.3 µl (human IKZF3 catalogue #SA-17027, human RB1 catalogue #SA-10550, or human beta-2 microglobulin catalogue #SA-10012) per manufacturer instructions (QUANTIGENE® 2.0 AFFYMETRIX®). Then 20 µl working probe set reagents were added to 80 µl lysate dilution (or 80 µl lysis mix for background samples) on the capture plate. Plates were then incubated for 16-20 hours at 55° C. to hybridize (target RNA capture). Signal amplification and detection of target RNA was begun by washing plates with buffer 3 times (300 µl/well) to remove any unbound material. Next, the 2.0 Pre-Amplifier hybridization reagent (100 µl/well) was added, incubated at 55° C. for 1 hour then aspirated and wash buffer was added and aspirated 3 times. The 2.0 Amplifier hybridization reagent was then added as described (100 µl/well), incubated for 1 hour at 55° C. and the wash step was repeated as described previously. The 2.0 Label Probe hybridization reagent was added next (100 µl/well), incubated for 1 hour at 50° C. and the wash step again was repeated as described previously. The plates were again centrifuged at 240 g for 20 seconds to remove any excess wash buffer and then, the 2.0 Substrate was added (100 µl/well) to the plates. Plates were incubated for 5 minutes at room temperature, and then, the plates were imaged on a PerkinElmer Envision multilabel reader in luminometer mode within 15 minutes.

Data determination: For the gene of interest, the average assay background signal (i.e., no lysate, just 1× lysis buffer) was subtracted from the average signal of each technical replicate. The background-subtracted, average signals for the gene of interest were then normalized to the background-subtracted average signal for the housekeeping mRNA (for Ramos cells, it was beta-2-microglobulin). The percent inhibition for the treated sample was calculated relative to the average of the untreated sample lysate. Results of QUANTIGENE® assays for cells treated with ASO-005459 is shown in Table 4.

Example 5: qPCR Assay to Measure Reduction of SNCA mRNA in SK-N-BE(2) Cells

ASO-005459 targeting SNCA was tested for its ability to reduce SNCA mRNA expression in human SK-N-BE(2) neuroblastoma cell acquired from ATCC (CRL-2271).

SK-N-BE(2) cells were grown in cell culturing media (MEM [Sigma, cat. no M2279] supplemented with 10% Fetal Bovine Serum [Sigma, cat. no F7524], 1× Glutamax™ [Sigma, cat. no 3050-038] 1× MEM Non-essential amino acid solution [Sigma, cat. no M7145] and 0.025 mg/ml Gentamycin [Sigma, cat. no G1397]). Cells were trypsinized every 5 days, by washing with Phosphate Buffered Saline (PBS), [Sigma cat. no 14190-094] followed by addition of 0.25% Trypsin-EDTA solution (Sigma, T3924), 2-3 minutes incubation at 37° C., and trituration before cell seeding. Cells were maintained in culture for up to 15 passages.

For experimental use, 12,500 cells per well were seeded in 96 well plates (Nunc cat. no 167008) in 100 µL growth media. Oligonucleotides were prepared from a 750 µM stock. ASO dissolved in PBS was added approximately 24 hours after the cells were seeded to a final concentration of 25 µM for single point studies. Cells were incubated for 4 days without any media change. For potency determination, 8 concentrations of ASO were prepared for a final concentration range of 16-50,000 nM. ASO-004316 (CcAAAtct-tataataACtAC, SEQ ID NO: 7) and ASO-002816 (TTCctt-tacaccACAC, SEQ ID NO: 8) were included as controls.

After incubation, cells were harvested by removal of media followed by addition of 125 µL PURELINK® Pro 96 Lysis buffer (Invitrogen 12173.001A) and 125 µL 70% ethanol. RNA was purified according to the manufacture's instruction and eluted in a final volume of 50 µL water resulting in an RNA concentration of 10-20 ng/µl. RNA was diluted 10 fold in water prior to the one-step qPCR reaction. For one-step qPCR reaction qPCR-mix (qScript TMXLE 1-step RT-qPCR TOUGHMIX® Low ROX from QauntaBio, cat. no 95134-500) was mixed with two Taqman probes in a ratio 10:1:1 (qPCR mix:probe1:probe2) to generate the mastermix. Taqman probes were acquired from LifeTechnologies: SNCA: Hs01103383_m1; PROS1: Hs00165590_m1: TBP: 4325803; GAPDH 4325792. Mastermix (6 µL) and RNA (4 µL, 1-2 ng/µL) were then mixed in a qPCR plate (MICROAMP® optical 384 well, 4309849). After sealing, the plate was given a quick spin, 1000 g for 1 minute at RT, and transferred to a Viia™ 7 system (Applied Biosystems, Thermo), and the following PCR conditions used: 50° C. for 15 minutes; 95° C. for 3 minutes; 40 cycles of: 95° C. for 5 sec followed by a temperature decrease of 1.6° C./sec followed by 60° C. for 45 sec. The data was analyzed using the QuantStudio™ Real_time PCR Software.

Example 6: In Vitro Analysis of ASO-005459 on the Reduction of Human SNCA mRNA Potency of ASO-005459 in Mouse Neurons Using the methods described above in Example 2, ASO-005459 was tested for its ability to reduce SNCA protein expression as a downstream result of reduction in SNCA mRNA. Briefly, primary neurons derived from PAC-A53T mice were treated with ASO-005459 or control ASOs for 14 days. Cells were then fixed and the levels of SNCA protein and tubulin protein were measured by high content imaging. Tubulin levels were measured to monitor toxicity and to normalize SNCA protein reduction.

As shown in Table 1 below, incubation of cells with 4 nM of ASO-005459 resulted in a 21% reduction in the SNCA protein expression. With 40 nM and 5 μM of ASO-005459, the SNCA protein expression was reduced by 84% and 86%, respectively. In contrast, ASO-005459 had minimal to no effect on the level of tubulin protein expression.

TABLE 1

ASO-005459 activity in A53T-PAC neurons

| ASO-005459 concentration | aSyn/tub % inh | SD | N | Tub % inh | SD | N |
|---|---|---|---|---|---|---|
| 4 nM | 21.11 | 33.71 | 3 | −8.60 | 12.07 | 4 |
| 40 nM | 84.28 | 13.21 | 8 | 4.32 | 28.65 | 7 |
| 5 μM | 86.45 | 7.91 | 2 | 29.01 | 18.06 | 2 |

SD = standard deviation
N = number of tests

Figure 2B:
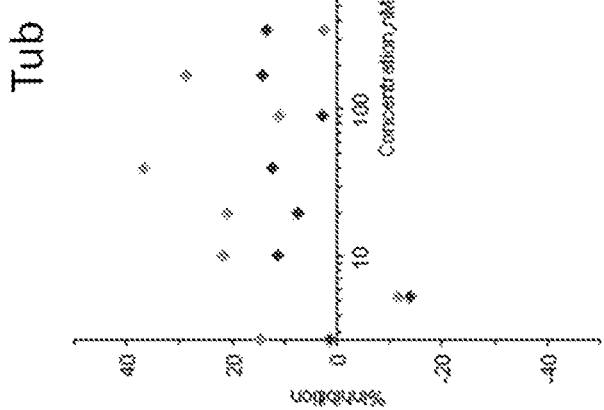
FIGS. 2A and 2B show the effect of ASO-005459 on SNCA and tubulin (Tub) protein expression in primary neurons isolated from A53T-PAC transgenic mice. Neurons were treated with a 10-point titration of ASO-005459 and amounts of SNCA and tubulin protein measured. Percent inhibition of α-Syn/Tub ratio (FIG. 2A) and Tub levels (FIG. 2B) are shown. Each data point represents an individual replicate.
Figure 2A:
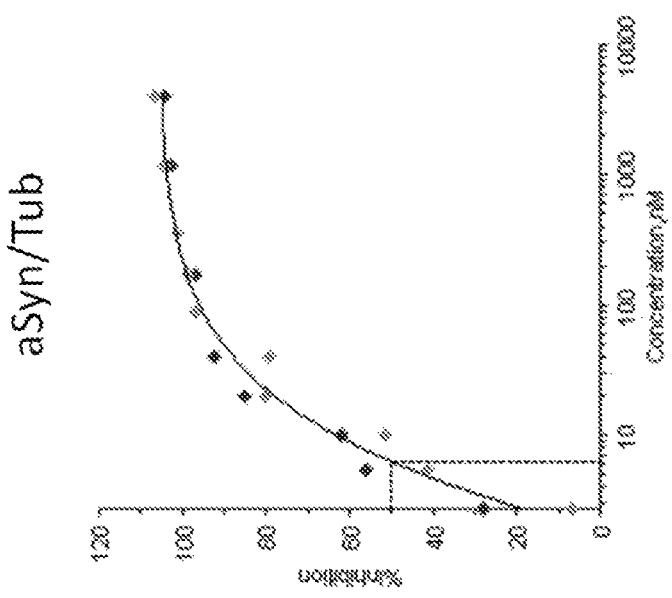

To further evaluate potency, A53T-PAC neurons were treated with a 10-point titration of ASO-005459, as described above in Example 2A, and the $IC_{50}$ s for the effect on SNCA and tubulin proteins determined. As shown in FIGS. 2A and 2B, and Table 2 (below), a concentration-dependent reduction in α-Syn/tubulin ratio was observed, with an average $IC_{50}$ of 7.4 nM. This observation was consistent with the single point activity data shown in Table 1 (above). Moreover, ASO-005459 produced negligible effects on Tub levels. Taken together these results indicate that ASO-005459 potently reduces SNCA protein levels with minimal effect on overall cell viability.

TABLE 2

Potency and selectivity estimate for ASO-005459 for SNCA and tubulin protein in A53T-PAC neurons

| aSyn/tub $IC_{50}$ (nM) | SD | N | tub $IC_{50}$ (nM) | SD | N |
|---|---|---|---|---|---|
| 7.42 | 2.73 | 6 | >4000 | NA | 5 |

SD = standard deviation
N = number of tests

Efficacy of ASO-005459 in SK-N-BE(2) Cells

Using the method described in Example 5, ASO-005459 was tested for its ability to reduce SNCA mRNA in SK-N-BE(2) after 4 days treatment.

Incubation of cells with 25 μM ASO-005459 resulted in 92% reduction in SNCA mRNA in SK-N-BE(2) cells.

Potency of ASO-005459 in Human Neurons

ASO-005459 potency for SNCA was confirmed using primary human neurons as described above in Example 3. Briefly, human neurons were derived from induced pluripotent stem (iPS) cells. Cells were treated with ASO-005459 or control ASOs for 6 days and then, mRNA levels were measured by QUANTIGENE® Assay. Because human neurons also express PROS1, a potential off-target for ASO-005459, the PROS1 mRNA level was also measured to assess the effect of ASO-005459 on off-target genes. In addition, tubulin (TUBB) mRNA was measured to monitor toxicity.

Figure 3:
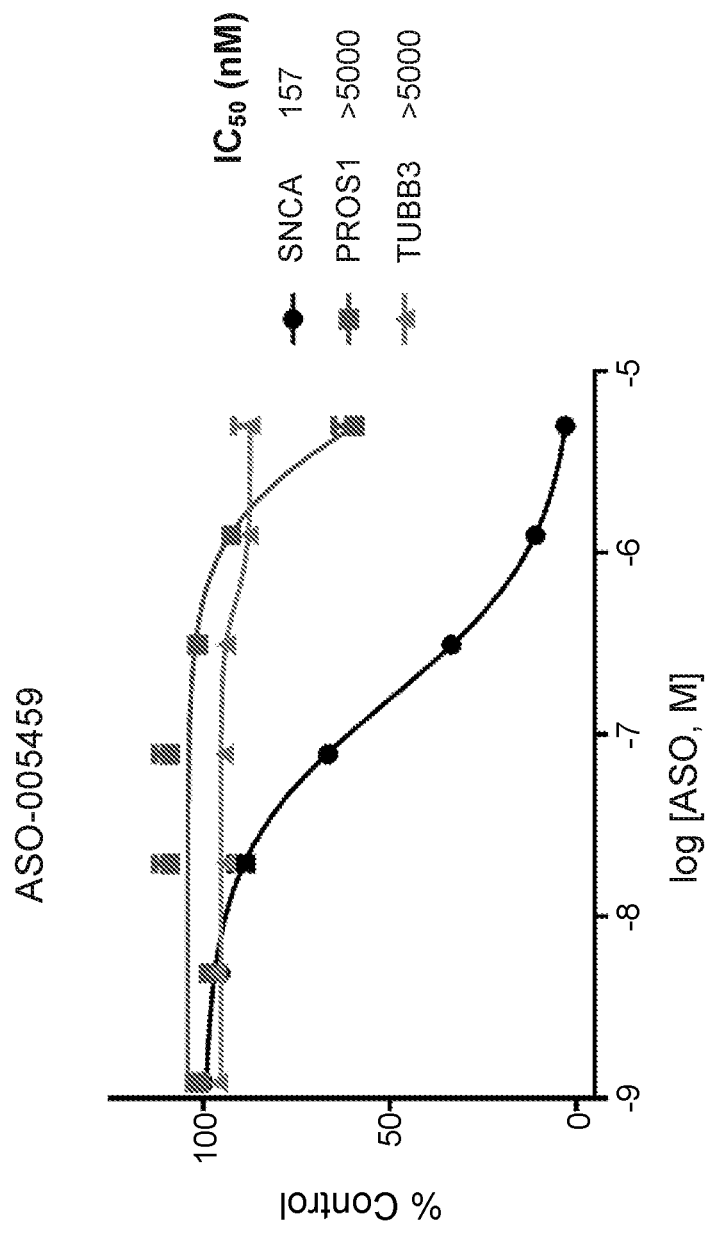
FIG. 3 shows the effect of ASO-005459 on the expression level of SNCA (circle), Protein S (alpha) (PROS1 (square)), and Tubulin (TUBB3 (triangle)) mRNAs in human neurons. The neurons were treated with various concentrations of ASO-005459 for 6 days, and then, the mRNA levels were measured by QUANTIGENE® assay. The expression level of the mRNAs is shown as a percent of the control. Data shown represents the mean±SD from duplicate determinations.

As shown in FIG. 3 and Table 3 (below), ASO-005459 induced a concentration-dependent reduction in SNCA expressed in human neurons, with an average $IC_{50}$ of 100 nM. This $IC_{50}$ is ~13-fold weaker than the $IC_{50}$ for reducing SNCA protein in PAC-A53T neurons (Table 2, above). The reason for this potency shift is not clear but could be due to differences in ASO uptake, metabolism, or kinetics of SNCA knock-down. While ASO-005459 also exhibited concentration-dependent reductions of PROS1 mRNA in the human neurons; the $IC_{50}$ was 30-50 fold weaker than the $IC_{50}$ for SNCA. These results confirm ASO-005459 activity for SNCA in human neurons and indicate that ASO-005459 is 30-50-fold more selective for SNCA compared to PROS1.

TABLE 3

Potency and Selectivity of ASO-005459 on SNCA and PROS1 mRNA in human neurons

| Assay Date | Batch | SNCA $IC_{50}$ (nM) | PROS1 $IC_{50}$ (nM) | TUBB3 $IC_{50}$ (nM) | PROS1/ SWG4 $IC_{50}$ ratio |
|---|---|---|---|---|---|
| Aug. 26, 2016 | 01-001 | 42 | 2127 | >5000 | 51 |
| Dec. 8, 2016 | 01-004 | 157 | >5000 | >5000 | >32 |

Batch = particular lot-number of ASO-005459 used

Potency of ASO-005459 in Ramos Cells

IKZF3 is another potential off-target for ASO-005459, but, unlike PROS1, it is not expressed in human neurons. Instead, IKZF3 is robustly expressed in Ramos cells, a human lymphocytic cell line. Ramos cells were treated with 1 μM ASO-005459 and the effect on IKZF3 mRNA expression was measured. To monitor toxicity, beta-2 microglobulin mRNA was also measured. Since Ramos cells do not express SNCA, another gene, RB1 (RB transcriptional corepressor 1), was used as a positive control for ASO-mediated knockdown. ASO-006754 (GGTgaggtttggtaGA, SEQ ID NO: 9) and ASO-006755 (GGTgaggtttggtagaAG, SEQ ID NO: 10) target RB1 and were included the study. As shown in Table 4 (below), at 1 μM concentration, ASO-005459 did not affect IKZF3 mRNA expression, demonstrating ASO-005459's specificity for SNCA. ASO-005459 also did not affect the expression of RB1 and β2M mRNAs, indicating that ASO-005459 is not toxic to Ramos cells. In contrast, ASO-006754 and ASO-006755 (the control ASOs) reduced RB1 levels by 87% and 83%, respectively, confirming the ASO activity in Ramos cells.

TABLE 4

Effect of 1 μM ASO-005459 on IKZF3 in Ramos cells

| ASO | Target | Batch | IKZF3 (% con) | RB1 (% con) | β2M (% con) |
|---|---|---|---|---|---|
| ASO-005459 | SNCA | 01-004 | 102 | 99 | 94 |
| ASO-006754 | RB1 | 01-001 | 104 | 13 | 87 |
| ASO-006755 | RB1 | 01-001 | 116 | 17 | 83 |

Batch = particular lot-number of the ASO used

Collectively, the results presented here demonstrate that ASO-005459 is potent and highly selective for reducing SNCA mRNA, which in turn mediates the reduction of SNCA protein levels. The results also show ASO-005459 is well tolerated both in mouse and in human neurons. These findings support the continued development of ASO-005459 as a disease-modifying therapeutic for the treatment of synucleinopathies.

Example 7: In Vivo Tolerability and In Vivo SNCA mRNA Reduction

The in vivo tolerability of the ASO of the present disclosure was tested to see how the ASO was tolerated when injected into different animal models (i.e., mice and cynomolgous monkeys).

Mice

Subjects: Male and female (2-3 months old) PAC-Tg (SNCA$^{A53T}$)$^{+/+}$; SNCA$^{-/-}$ ("PAC-A53T") mice carrying the entire human SNCA gene with a A53T mutation on a mouse SNCA knockout background were used for acute, long term, and PK/PD in vivo efficacy studies. In some cases wild-type (WT) C57B/6 mice were used for long term (i.e., 4 weeks) health assessment. Mice were housed in groups of 4 or 5 in a temperature controlled housing room with food and water available ad libitum. All procedures involving mice were conducted according to Animal Test Methods (ATM) approved by the Bristol-Myers Squibb Animal Care and Use Committee (ACUC).

ASO Dosing Solution Preparation: Sterile saline (1 mL) syringes fitted with 0.2 m Whatman filters and nuclease free centrifuge tubes were used to prepare dosing solutions. Indicated volume of water or saline was added to an ASO powder and was vortexed (~1 min) to dissolve the ASO powder. The solution was then allowed to sit for 10 min and was vortexed again for ~1 min. The tubes were briefly centrifuged to return all of the liquid to the bottom of the tube, and then, the solution was filtered through a 0.2 m sterile filter into a 2nd RNase free tube. A small aliquot of the primary stock was diluted to 1 mg/ml for analysis of the concentration using Nanodrop. The analytical sample was vortexed three times with manual inversion to mix thoroughly. Then, the UV absorbance of the sample was measured twice at 260 nm with Nanodrop (the pedestal was rinsed and wiped three times before applying the sample). The test sample was discarded once the analysis was complete. The sample was considered ready for dosing if UV absorbance was between 90 and 110% of the sample. If UV absorbance exceeded 110% of the sample, a secondary dilution was prepared; if the absorbance was <90%, the sample was prepared at a higher initial concentration and similar steps were followed as described above. Samples were stored at 4° C. until use.

Freehand Intracerebroventricular (ICV) Injection: ICV injections were performed using a Hamilton micro syringe fitted with a 27 or 30-gauge needle, according to the method of Haley and McCormick. The needle was equipped with a polyethylene guard at 2.5-3 mm from the tip in order to limit its penetration into the brain. Mice were anesthetized using isoflurane anesthetic (1-4%). Once sufficiently anesthetized, the mice were held by the loose skin at the back of the neck with the thumb and first fingers of one hand. Applying gentle but firm pressure, the head of the animal was then immobilized by pressing against a firm flat level surface. Dosing was conducted using 10 μL Hamilton syringes fitted with a 27½ g needle. The needle tip was then inserted through the scalp and the skull, about 1 mm lateral and 1 mm caudal to bregma (i.e., right of the midline, about 3 mm back as measured from the eye line). Once the needle was positioned, the ASO was given in a volume of 5 μl in saline vehicle and injected over ~30 seconds. The needle was left in place for 5-10 seconds before removal. The mice were returned to their home cage and allowed to recover for ~2-4 min. Mice were observed continuously for 30 minutes immediately after dosing for adverse behavioral effects of drug and/or dosing. During this time, any mouse that convulsed more than 3 separate times was immediately euthanized and given an automatic score of 20. Drug tolerability was scored 1 hr±15 min post dosing. Animals dosed with non-tolerated compounds (tolerability score >4) were euthanized immediately following the 1 hr evaluation.

ASO Tolerability Assessment: Animals dosed with the ASOs were evaluated right after the dosing and monitored for 2 hours for any adverse effects. For acute tolerability (AT) studies, mice were evaluated at the time of dosing and again at the takedown, i.e., 3 days post ASO injection. For long term health assessment, the mice were weighed weekly and monitored for any health and behavioral issues until the completion of the experiment. Mice that had weight losses of greater than 15% of their initial body weight or exhibited tolerability issues were removed from the studies and euthanized. Health and tolerability assessments were conducted according to the following chart:

TABLE 5

| Tolerability scoring system$^a$ | | | | |
|---|---|---|---|---|
| Category | Score 1 | Score 2 | Score 3 | Score 4 |
| Hyperactivity, stereotypies, home cage behavior | Very slightly increased home cage exploration or rearing compared to controls | Increased home cage exploration (e.g. digging, burying, etc.) Increased grooming | Moderately increased home cage activity Detectable stereotypies (e.g. circling, repetitive behaviors, etc.) | Marked hyperactivity Marked stereotypies |
| Decreased vigilance, exploration and responsiveness | Some reduction in exploratory activity Responds normally to stimulation | Drowsiness Slightly reduced response to touch or handling | Stupor (reduced responsiveness, decreased corneal reflex) | Coma (does not respond to stimulation, e.g. pinch), no corneal reflex |

TABLE 5-continued

Tolerability scoring system[a]

| Category | Score 1 | Score 2 | Score 3 | Score 4 |
|---|---|---|---|---|
| Motor coordination and strength | Mild change to gait or grip strength (falls between 5-10 sec) No falls, normal righting response | Reduced grip strength (falls in less than 5 sec) Mild ataxia (e.g. slow righting response, swaying) | Highly reduced grip strength (falls in less than 2 sec) Ataxia (e.g. staggering, falling impaired walking) | Severe ataxia (e.g. crawling, fails to grip bar) No ability to right |
| Posture, appearance, breathing | Very slight abnormal posture (subtle) | Slight abnormal posture (e.g. hunched, extended, low posture, tail position, straub tail) Piloerection or ptosis unkempt coat | Moderately abnormal posture (e.g. ventral recumbency) Shallow breathing | Markedly abnormal posture (e.g. lateral recumbency) Facial paralysis (e.g. drooling, protruding tongue) Labored breathing |
| Tremor, hyper-activity, convulsion | Detectable tremor | Hyper-responsive to stimuli (e.g. noise) Marked tremors | Few or partial seizures, rearing and falling as part of convulsing | Repeated or continuous seizure (running, bouncing, clonic and/or tonic) |

[a]Normal is scored as "0". Animals are scored on an individual basis at successive time points post dosing. Observations are rated at 1 h ± 15 min, then 24 h ± 2 h, then 7 days (if appropriate). Convulsions count for the 1 hr timepoint, even if they occur prior to the observation window. A total tolerability score is calculated based on the sum of the individual category scores, with a maximum possible score of 20.

Tissue Collection: Following final behavioral and health assessments, mice were decapitated on a guillotine and the brains were quickly removed. Each brain was split into two hemispheres and a) hippocampus was dissected for mRNA measurements in the 3-day acute tolerability studies; b) hippocampus, brain stem, and striatum from one hemisphere were dissected for mRNA measurements, whereas the same regions were dissected from the second hemisphere for protein/PK measurements in the dose-response time course PK/PD studies.

In some of the studies, the blood and the cerebrospinal fluid (CSF) were also collected for PK (blood) and PK/protein (CSF) measurements. To collect the blood and the CSF, the mice were deeply anesthetized with Isoflurane (4%). Blood was collected via cardiac puncture using 23G needle. Once removed, the blood was transferred into 2 ml BD Microtainer (K2EDTA BD #365974) tubes and placed on ice until processing. To process the blood, the tubes were centrifuged at 4500×g for 10 min at 4° C. Then, the plasma was removed and placed into 0.5 ml Eppendorf tubes and stored at −80° C. until use. To collect the CSF, the thoracic cavity was opened exposing the heart, and as much of the blood was drained to avoid contamination of the CSF. The CSF samples were collected via Cisterna magna using micropipettes and placed into lo-bind protein Eppendorf tubes. Then, the tubes were centrifuged at 4500×g for 15 min at 4° C. The CSF was carefully transferred to clean lo-bind 0.5 ml Eppendorf tubes and stored at −80° C. until further use.

Cyno Data

Subject: Male cynomolgus monkeys weighing 3.5-10.0 kg at the start of the study were used. Each was implanted with an intrathecal cerebrospinal fluid (CSF) catheter entering at the L3 or L4 vertebrae. The distal tip of the polyurethane catheter extended within the intrathecal space to approximately the L1 vertebrae. The proximal end was connected to a subcutaneous access port located on the animal's lower back. Animals were allowed to heal for at least two weeks prior to the start of the study. Laboratory animal care was according to Public Health Service Policy on the Humane Care and Use of Laboratory Animals and the Guide for the Care and use of Laboratory Animals NRC (2011) (National Research Council: Guide for the Care and Use of Laboratory Animals (The National Academies Collection: Reports funded by National Institutes of Health). National Academies Press (US), Washington (DC)). The protocol was approved by the Wallingford Animal Care and Use Committee of the Bristol-Myers Squibb Company.

CSF & Blood Sampling: The CSF port was accessed subcutaneously using aseptic techniques, and CSF was sampled from awake animals sitting upright in a primate restraint chair. Approximately 0.1 ml of CSF was discarded at the start of collection to clear dead space in the catheter and port. CSF was collected by gravity flow to a maximum of 0.5 ml CSF per sample. CSF was spun at 2,000 g at 4° C. for 10 min. The supernatant was frozen on dry ice or in liquid nitrogen and kept at −90° C. until analyzed.

Blood was sampled from an available vein, typically the saphenous vein. Blood samples were prepared in a number of procedures depending upon the particular measure in question. For plasma, blood was collected into EDTA-treated tubes. For serum, blood was collected into serum-separator tubes and allowed to clot for at least 30 min prior to centrifugation. For measures of clotting and clotting factors, blood was collected into citrated tubes, and for analysis of RNA, blood was collected into tubes containing RNAlater. After processing, samples were frozen on dry ice or in liquid nitrogen and kept frozen until analyzed.

Intrathecal Dosing: Animals were trained to be dosed while awake and using modified commercially-available restraint chairs, animals were maintained in a prone position. SNCA-targeted anti-sense oligonucleotides (ASOs) were dissolved in saline, sterilized by filtration, and administered at 0.33 ml/min in a 1.0 ml volume followed by a 0.5 ml sterile water flush. Total infusion time was 4.5 min. Animals remained in the prone position for 30 min post infusion.

Necropsy: Cynomolgus monkeys were administered the appropriate volume of a commercially available euthanasia solution while anesthetized with ketamine and/or isoflurane. Necropsy tissues were obtained immediately thereafter and the brain was transferred to wet ice for dissection. Areas of interest were dissected using 4-6 mm slices in an ASI Cyno Brain Matrix as well as free handed techniques. Samples were placed fresh in RNAlater®, or frozen on dry ice for later analysis. CNS tissue was rapidly dissected form cynomolgus monkeys and pieces no longer than 4 mm on any axis were collected and placed in 5 mLs of RNA later. Samples were stored at 4° C. overnight then transferred to −20° C. for storage until analyzed.

Brain regions analyzed included medulla, pons, midbrain, cerebellum, caudate-putamen (left and right), hippocampus (left and right), frontal cortex (left and right), temporal cortex (left and right), parietal cortex (left and right), occipital cortex (left and right) and cortical white matter. Additionally, spinal cord was sampled at the cervical, thoracic and lumbar regions. Samples were also collected from liver, kidney and heart. On some occasions, samples of trigeminal nuclei, tibial nerve and the aorta were collected to examine off-target pharmacology in those areas.

ELISA Quantitation of ASO Concentration in Mouse or Monkey Tissue, Plasma, and CSF:

Tissue was homogenized with plasma and water in a 1:1 ratio. Standard curve was generated by 2-fold serial dilution from 5000 to 4.9 nM in plasma (for plasma and CSF) and in plasma:water (for tissues samples) and then further diluted to 5000-fold total with 5×SSCT (750 mM NaCl, and 75 mM sodium citrate, pH 7.0, containing 0.05% (v/v) Tween-20) alone and in 5×SSCT containing 35 nM capture and 35 nM detection reagents to obtain a standard range of 1-1000 pM. The dilution factor used varied depending on the expected sample concentration range. The capture probe was AAAGGAA with a 3' Biotin (Exiqon) and the detection probe was 5' DigN-isopropyl 18 linker—GTGTGGT (Exiqon).

Experimental samples and standards were added to Clarity lysis buffer (Phenomenex, cat #AL0-8579) in a 1:1 ratio prior to dilution with capture and detection buffer and before transferring to the ELISA plate. CSF samples were diluted with plasma (2-fold) prior to addition of lysis buffer. A streptavidin-coated plate (Thermo 15119) was washed 3 times with 5×SSCT buffer. 100 µl samples were added and incubated for 60 min at room temperature. The detection probe, 100 µl anti-Dig-AP Fab fragment diluted 1:4000 in PBS containing 0.05% Tween-20 (Roche Applied Science, Cat. No. 11 093 274 910), was added and incubated for 60 min at room temperature. After washing the plate with 2×SSCT buffer, 100 µl Tropix CDP-star Sapphire II substrate (Applied Biosystems) was added for 30 min at room temperature. ASO concentrations were measured by luminescence (Enspire-PerkinElmer).

Alpha-Synuclein Protein Measurements:

Brain tissue samples were homogenized at 10 ml/g tissue in RIPA buffer (50 mM Tris HCl, 150 mM NaCl, 1% NP-40, 0.5% sodium deoxycholate, 0.1% sodium dodecyl sulfate) using bead homogenizer Qiagen Tissuelyser II for 25 cycles/sec, with a 5 mm stainless steel bead for 2 min total. Homogenized samples were incubated 30 min on ice. 50 µL aliquot of each sample was retained for PK analysis. The remaining samples were centrifuged 20,800 g, for 60 min, 4° C. The supernatant was retained and used for analysis. Total protein was measured using Pierce BCA protein assay kit (23227).

Brain tissue extracts: SNCA protein was measured using the MJFR1+4B12 ELISA. Briefly, ELISA plates (Costar) were coated with 100 µl of the anti-SNCA antibody MJFR1 (Abcam) at a concentration of 0.1 µg/ml diluted in BupH carbonate-bicarbonate buffer, pH 9.4 (Thermo Scientific) overnight (O/N) at 4° C. The next day plates were washed 4-times with Dulbecco's PBS (Life Technologies) and blocked with 3% BSA (bovine serum albumin, protease free, Fraction V, Roche Diagnostic) in PBS for 2~3 h at room temperature (RT) or overnight at 4° C. Both the standards and the brain samples were diluted with 1% BSA/0.05% Tween/PBS containing Roche protease inhibitor (Roche 11836145001, 1 pellet/25 ml) and Phosphatase Inhibitor 2&3 (Sigma, 1:100). SNCA wild-type (rPeptide) was used as a standard. Samples were loaded in duplicate (50 l/well) and incubated for O/N at 4° C. After plates were equilibrated to RT, 50 µl of the detection antibody 4B12 (Biolegend) (diluted 1:4000 in 1% BSA/0.1% Tween/DPBS) was added to each well and co-incubated with the samples at RT for ~2 hours. Detection antibody was pre-conjugated with alkaline phosphatase (AP kit from Novus Biologicals). Plates were then washed 4-times with 0.05% Tween/PBS and developed with 100 µl of alkaline phosphatase substrate (Tropix CDP Star Ready-to-Use with Sapphire II, T-2214, Life Technologies) for 30 minutes. Luminescence counts were measured with Perkin Elmer EnVision (2102 Multilabel Reader). The plates were kept constant shaking (Titer plate shaker, speed 3) during the assay. Data was analyzed using GraphPad Prism. Total protein in brain tissue was measured using a Micro protein assay kit (Thermofisher #23235) according to manufacturer's instructions.

Cerebral spinal fluid (CSF): SNCA protein was measured using the U-PLEX Human SNCA Kit: (cat #K151WKK-2, Meso Scale Discovery) according to manufacturer's instructions. CSF samples were diluted 10-fold. Hemoglobin was measured in CSF samples using the Abcam mouse Hemoglobin ELISA kit (ab157715). CSF samples were diluted 40-fold for the hemoglobin measurements.

mRNA Measurements by qRT-PCR

Brain regions were harvested and placed in 1.5 ml RNA-later Tissue Protect tubes (Qiagen cat #76514) that were prefilled with RNA-later, a RNA stabilization solution. Tissue in RNA-later solution can be stored at 4° C. for 1 month, or at −20° C. or −80° C. indefinitely.

RNA Isolation: RNeasy Plus Mini Kit: RNA from mouse hippocampus and cortex and was isolated using the RNeasy Plus Mini Kit (Qiagen cat #74134). Tissue samples were homogenized in a volume of 600 µL or 1200 µL RLT Plus buffer containing 10 l/ml of 2-mercaptoethanol and 0.5% Reagent Dx. 600 µL lysis buffer was used if the tissue sample was <20 mg, 1200 µl lysis buffer was used for tissue samples >20 mg. For homogenization, tissue sample was transferred to a 2.0 mL round-bottom Eppendorf Safe-Lock tube (Eppendorf cat #022600044) containing 600 µL RLT Plus Buffer (plus 10 µl/ml of 2-mercaptoethanol and 0.5% Reagent Dx), and a 5 mm stainless steel Bead (Qiagen cat #69989) Samples were homogenized, using a Qiagen's TissueLyser II instrument. Samples were processed for 2.0 min at 20 Hz, samples rotated 1800 and processed for another 2.0 min at 20 Hz. Samples were then processed 2.0 min at 30 Hz, samples rotated 180° and processed for another 2.0 min at 30 Hz. Longer and/or at higher frequency homogenization used if processing not complete. A 600 µL of the tissue lysate was then transferred into a gDNA Eliminator spin column in a 2.0 mL collection tube and samples centrifuged for 30 secs at 10,000 g. All centrifugation steps were performed at RT. The flow-through was collected and an equal volume of 70% ethanol added and mixed. 600 µL was transferred to RNeasy spin column placed in a 2.0 mL collection tube and samples centrifuged for 15 secs at 10,000 g. The flow-through was discarded and the remaining 600 µL sample added to the spin column. The spin columns were centrifuged and the flow-through discarded. Columns were washed with 700 µL of Wash Buffer RW1, centrifuged for 15 secs at 10,000 g, and the flow-through discarded The columns were then washed 2-times with 500 µL of Buffer RPE containing 4 volumes of ethanol as described in kit protocol. Columns were first centrifuged for 15 secs at 10,000 g for first wash and then for 2.0 min at 10,000 g for the second wash. After second wash, columns were centrifuged once for 1.0 min at 10,000 g to dry the membranes. Columns were then transferred to a new 1.5 mL collection tube and 30 µL of RNase-free water was added directly to the center of the membrane. The membranes were allowed to incubate for 10 min at RT. Then, the columns were centrifuged for 1.0 min at 10,000 g to elute the RNA. The elution, containing the RNA, was collected and stored on ice until the RNA concentrations could be determined by UV absorbance using a NanoDrop Spectrophotometer (Thermo). RNA samples were stored at −80° C.

RNA Isolation: RNEASY® Plus Universal Mini Kit: RNA from all other Cyno, Mouse, and Rat tissue samples was isolated using RNEASY® Plus Universal Mini Kit (Qiagen cat #73404). For homogenization, 50 µg or less of tissue sample was transferred to a 2.0 mL round-bottom Eppendorf Safe-Lock tube (Eppendorf cat #022600044) containing 900 µL QIAZOL® Lysis Reagent, and a 5 mm stainless steel Bead (Qiagen cat #69989) Samples were homogenized, using a Qiagen's TissueLyser II instrument. Samples were processed for 2.0 min at 20 Hz, samples rotated 1800 and processed for another 2.0 min at 20 Hz. Samples were then processed 2.0 min at 30 Hz, samples rotated 180° and processed for another 2.0 min at 30 Hz. Longer and/or at higher frequency homogenization used if processing not complete. Homogenized tissue lysate was then transferred into a new 2.0 mL round-bottom Eppendorf Safe-Lock tube and left at RT for 5.0 min. 100 µL of gDNA Eliminator Solution was added to each tube and tubes were vigorously shaken for 30 secs. 180 µL of Chloroform (Sigma cat #496189) was added to each tube and tubes were vigorously shaken for 30 secs. Tubes were left at RT for 3 min. Centrifuge tubes at 12,000 g for 15 min at 4° C. After centrifugation the upper aqueous phase was transferred to a new 2.0 mL round-bottom Eppendorf Safe-Lock tube ~500 µL. An equal volume of 70% ethanol added and mixed. All future centrifugation steps were performed at RT. 500 µL was transferred to RNeasy spin column placed in a 2.0 mL collection tube and samples centrifuged for 15 secs at 10,000 g. The flow-through was discarded and the remaining 500 µL sample added to the spin column. The spin columns were centrifuged and the flow-through discarded and the columns washed with 700 µL of Wash Buffer RWT containing 2 volumes of ethanol. Columns were centrifuged for 15 secs at 10,000 g, the flow-through discarded. The columns were then washed twice with 500 µL of Buffer RPE containing 4-volumes of ethanol as described in kit protocol. Columns were first centrifuged for 15 secs at 10,000 g for first wash and then for 2.0 min at 10,000 g for the second wash. After second wash, columns were centrifuged once for 1.0 min at 10,000 g to dry the membranes. Columns were then transferred to a new 1.5 mL collection tube and 30 µL of RNase-free water added directly to the center of the membrane. Membranes were allowed to incubate for 10 min at RT. Columns were centrifuged for 1.0 min at 10,000 g to elute the RNA. The elutions, containing the RNA, were collected and stored on ice until RNA concentration determined by UV absorbance using a NanoDrop Spectrophotometer (Thermo). RNA samples were stored at −80° C.

cDNA Synthesis by Reverse Transcription: 300 ng of RNA was diluted to a final volume of 10.8 µL using nuclease-free water (Invitrogen cat #10977-015) in a PCR-96-AB-C microplate (Axygen cat #321-65-051). Added 6.0 µL to each well of reaction mix 1 containing the following: 2.0 µL of 50 µM random decamers (Ambion cat #AM5722G) and 4.0 µL of a 1× dNTP mix (Invitrogen cat #10297-018). The plate was sealed with optical sealing tape (Applied Biosystems cat #4360954) and centrifuged for 1.0 min at 1,000×g at RT. Next, the plate was heated for 3.0 min at 70° C. using a 96-well Thermal Cycler GeneAmp PCR System 9700 (Applied Biosystems). The plate was then cooled completely on ice. Next, 3.25 µL of the reaction mix 2 (containing 2 µL of 10× strand buffer, 1.0 µL of MMLV-RT 200 U/µL reverse transcriptase enzyme (Ambion cat #2044), and 0.25 µL of RNase inhibitor 40 U/µL (Ambion cat #AM2682)) were added to each of the wells. Plate was sealed with optical sealing tape and centrifuged for 1.0 min at 1,000×g at RT. Using a 96-well Thermal Cycler, the plate was heated at 42° C. for 60 min proceeded by 95° C. for 10 min. Then, the plates were cooled on ice. The cDNA plates were stored at −20° C. until ready to use for PCR analysis.

qPCR for amplification and quantification of SNCA and GAPDH mRNA expression: cDNA was diluted 5-fold in nuclease free water in a PCR-96-AB-C microplate. 16 µL of Master Mix solution consisting of the following: 10 µL of 2× Taqman Gene Expression Master Mix (Applied Biosystems cat #4369016), 1.0 µL of 20× Taqman primer-probe set (Applied Biosystems), and 5.0 µL of nuclease-free water, was added to each well of a 384-well optical PCR plate (Applied Biosystems cat #4483315). 4.0 µL of diluted cDNA was added to each well of the 384-well optical PCR plate. Plate was sealed with optical sealing tape and centrifuged for 1.0 min at 1,000×g at RT. PCR was performed on the Applied Biosystems 700 HT Fast Real-Time PCR System using the following parameters in standard mode: 50° C. for 2.0 min, 95° C. for 10 min, followed by 40 cycles of 95° C. for 15 secs and 60° C. for 1.0 min.

qRT-PCR primer-probe sets: Primer-probes sets from Applied Biosystems (Thermo Fisher) included the following:
1) Human alpha synuclein (cat #Hs01103383_m1) FAM labelled
2) Human PROS1 (cat #HS00165590_m1) FAM labelled
3) Cyno alpha synuclein (cat #Mf02793033_m1) FAM labelled
4) Cyno GAPDH (cat #Mf04392546_g1) FAM labelled
5) Cyno GAPDH (cat #Mf04392546_g1) VIC labelled Primer Limited
6) Rat alpha synuclein (cat #Rn01425141_m1) FAM labelled
7) Rat GAPDH (cat #Rn01775763-g1) FAM labelled
8) Rat GAPDH (cat #4352338E) VIC labelled Primer Limited
9) Mouse GAPDH (cat #Mm99999915-g1) FAM labelled
10) Mouse GAPDH (cat #4352339E) VIC labelled Primer Limited.

Example 8: Analysis of In Vivo Activity and Tolerability of ASO-005459 in Mice

ASO-005459 is a LNA-modified ASO specific for human SNCA. The in vitro results (described above) demonstrate that ASO-005459 is potent and selective for reducing SNCA mRNA in primary neurons. The in vitro results also suggest that that ASO-005459 is well tolerated.

A53T-PAC Mice

To evaluate whether these results are also true in vivo, 100 µg of ASO-005459 was administered to A53T-PAC mice via ICV injection, and both the tolerability and the SNCA mRNA knockdown (KD) in the hippocampus were assessed at 3 days post injection, as described in Example 4 (above).

Figure 4:
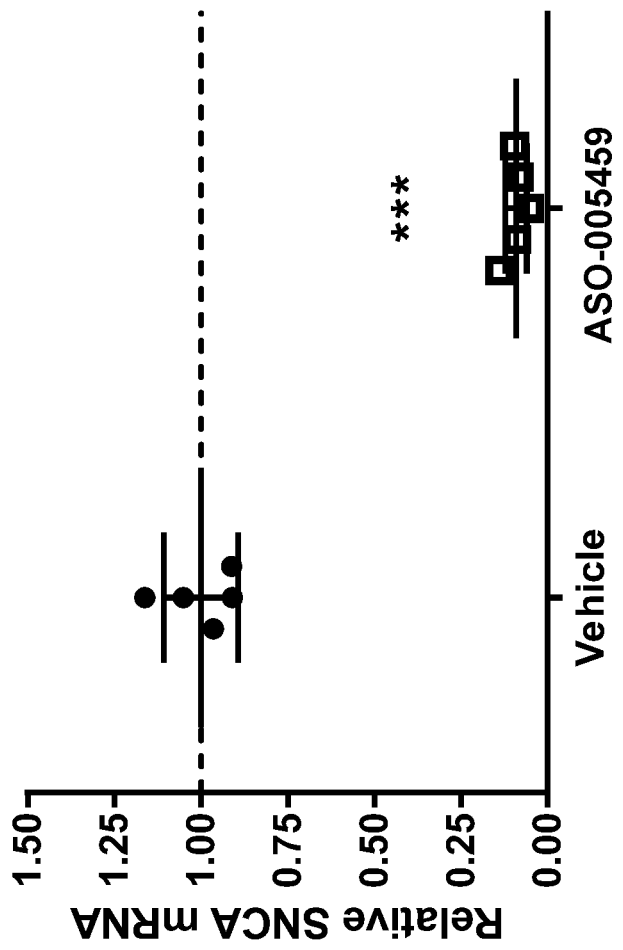
FIG. 4 shows the SNCA mRNA expression levels in the hippocampus of A53T-PAC mice at three days post ICV administration of 100 μg of ASO-005459 (open square) or control vehicle (closed circle). SNCA mRNA expression levels were measured by qRT-PCR, normalized to GAPDH mRNA, and then expressed relative to the mean expression level of the vehicle group. The horizontal line marks the reference value of 1 (i.e., value at which the SNCA mRNA expression would be equivalent to expression level observed in the vehicle control group). Data shown represents the mean±SD from duplicate determination. Statistics shown is based on 1-way ANOVA with Dunnett's post-test. ***p<0.001.

As shown in Tables 6 and 7 (below), ASO-005459 was well tolerated with an overall mean tolerability score of 1. In addition, ASO-005459 significantly reduced SNCA mRNA levels by >90% in the hippocampus at 3 days post administration. (FIG. 4).

TABLE 6

| | Tox Score @1 D | 3D mRNA % KD | Tox Score @28 D | Tox Score WT @28 D |
|---|---|---|---|---|
| ASO-005459 | 0.50 | 90.83 | | 0.00 |

TABLE 7

ASO-005459 tolerability in A53T-PAC mice, 3-day study

| Animal# | Hyper-activity | Vigilance | Motor S&C | Posture/ Breathing | Tremor/ Convulsions | Total Score |
|---|---|---|---|---|---|---|
| 31 | 0 | 2 | 1 | 2 | 0 | 5 |
| 32 | 0 | 0 | 0 | 0 | 0 | 0 |
| 33 | 0 | 0 | 0 | 0 | 0 | 0 |
| 34 | 0 | 0 | 0 | 0 | 0 | 0 |
| 35 | 0 | 0 | 0 | 0 | 0 | 0 |
| mean |   |   |   |   |   | 1.00 |
| SEM |   |   |   |   |   | 1.00 |

To evaluate activity in vivo, A53T-PAC mice were dosed with ASO-005459 at 3.13 µg, 12.5 µg, 25 µg, or 50 µg concentration via ICV injection. Tolerability was assessed by measuring body weights at days 7 and 14 post dosing. The expression of SNCA mRNA was assessed at 14 days post dosing, when the animals were sacrificed and their tissues harvested. SNCA mRNA knockdown was measured in three brain regions: Hippocampus, brainstem, and striatum. Brainstem and striatum are two of the regions that are most affected in the brains of MSA and PD patients. In a separate study, C57BL/6 mice were dosed with 100 µg of ASO-005459 and tolerability was assessed by measuring the body weight of the animals at days 7, 14, 21, and 28 post dosing. 100 µg ASO-005459 was dosed ICV in wild-type (WT) C57BL/6 mice, and the body weight and behavior were monitored over a 4-week period. Because ASO-005459 does not target mouse SNCA, reduction in SNCA mRNA expression was not measured in these animals.

Figure 5A:
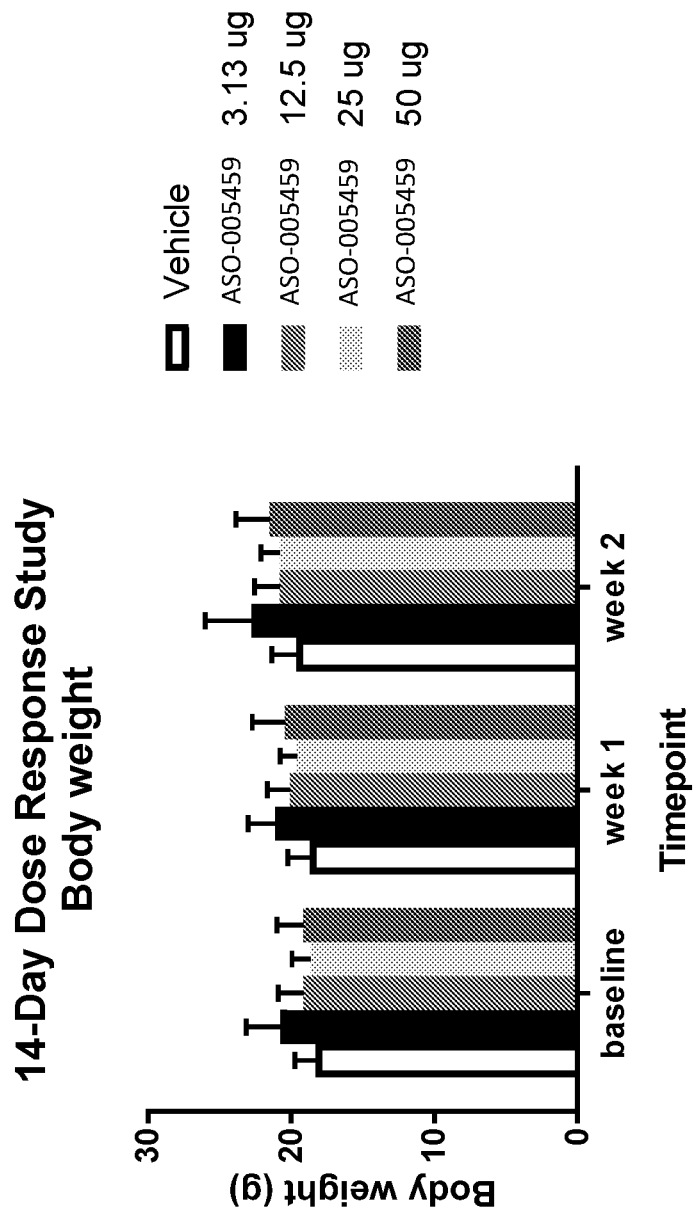
FIGS. 5A and 5B show a comparison of the average body weight of mice treated with ASO-005459.
Figure 5B:
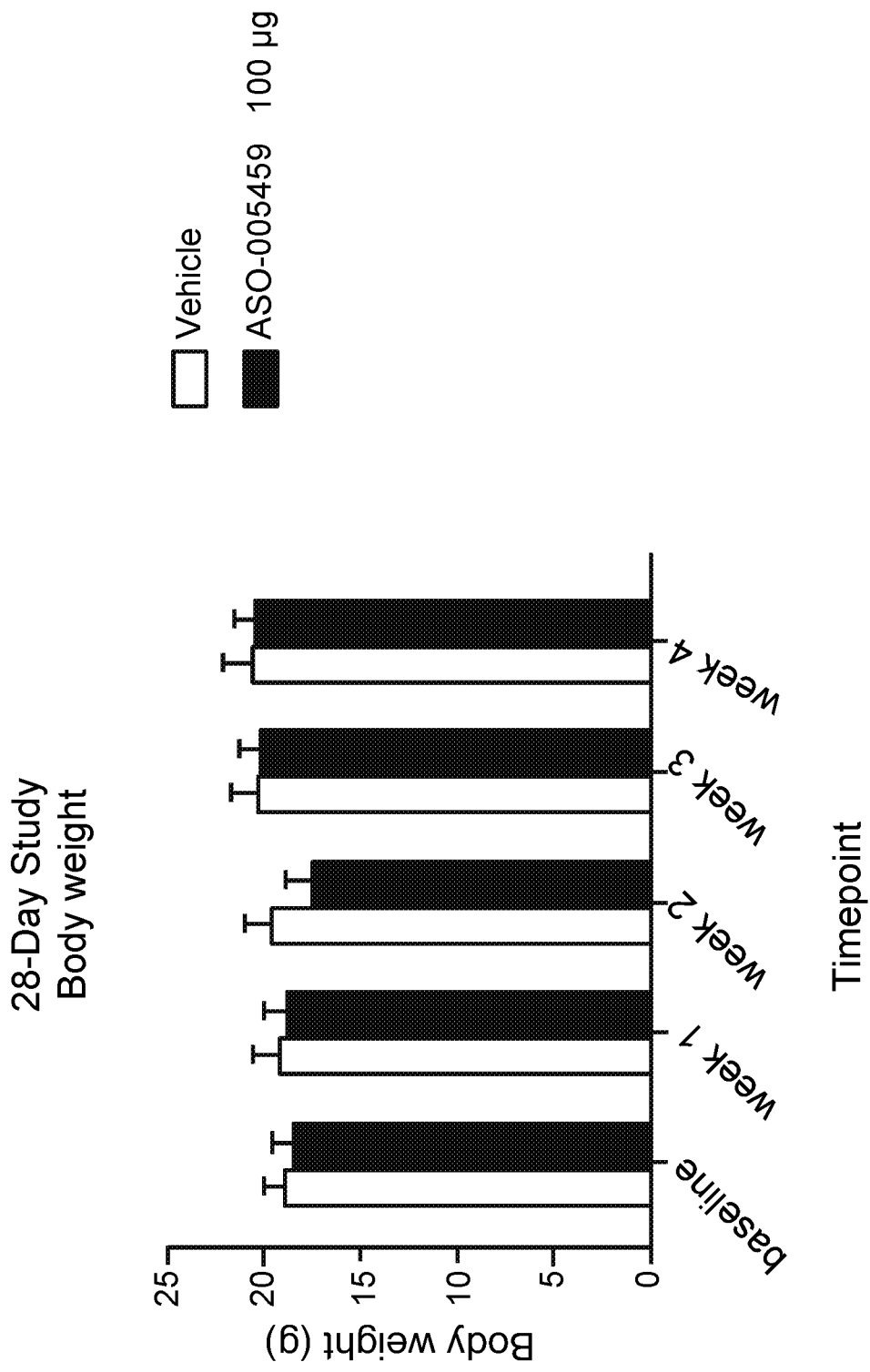
Figure 6B:
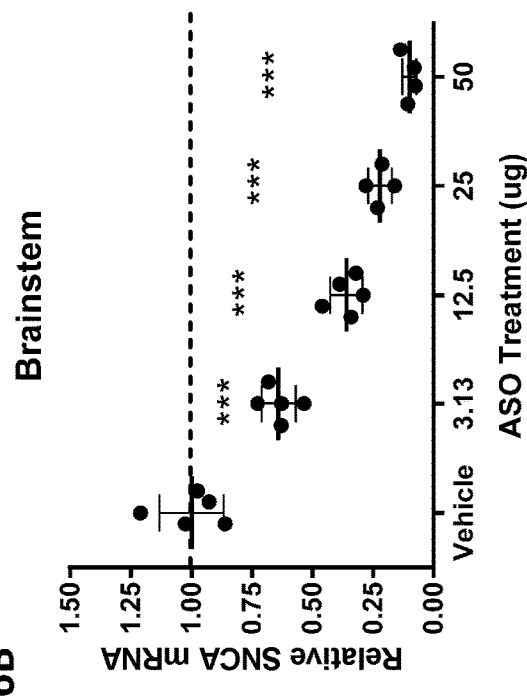
FIGS. 6A, 6B, and 6C show the SNCA mRNA expression levels in the hippocampus (FIG. 6A), brainstem (FIG. 6B), and striatum (FIG. 6C) of A53T-PAC mice at 14 days post ICV administration of ASO-005459 (3.13 μg, 12.5 μg, 25 μg, or 50 μg) or the vehicle control. SNCA mRNA levels were measured by qRT-PCR, normalized to GAPDH mRNA, and then expressed relative to the mean of the vehicle group. Data shown represents the mean±SD from multiple animals (n=5). Each circle represents an individual animal. The horizontal line marks the reference value of 1 (i.e., value at which the SNCA mRNA expression would be equivalent to expression level observed in the vehicle control group). Statistics shown is based on 1-way ANOVA with Dunnett's post-test. ***p<0.001.
Figure 6A:
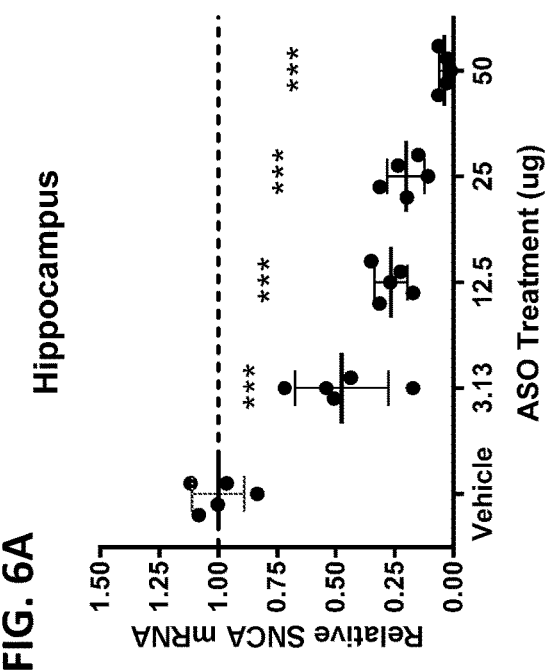
Figure 6C:
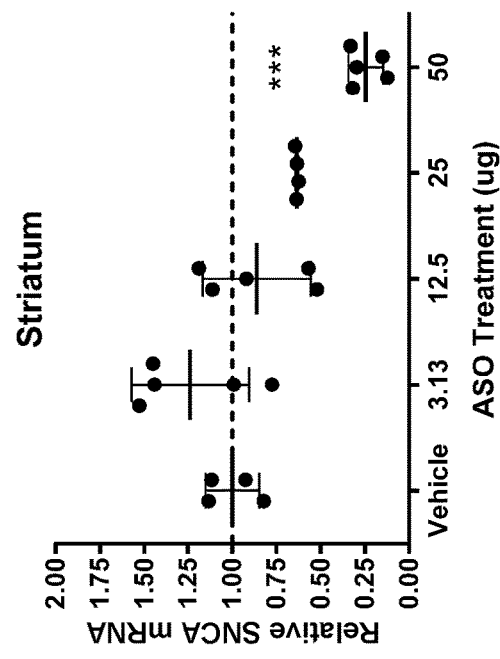

As shown in FIGS. 5A and 5B, there were no significant differences in the body weight of the mice (both A53T-PAC mice and C57BL/6 mice) treated with ASO-005459 (for all concentrations) and those treated with the control vehicle. The animals (C57BL/6) did not exhibit any abnormal behaviors during the course of the experiment. See Table 8 (below). Such results demonstrate that ASO-005459 was well tolerated. Also, in mice treated with ASO-005459, there was a significant and dose-dependent reduction in SNCA mRNA expression in all three brain regions tested. See FIGS. 6A-6C. In the hippocampus, the SNCA mRNA expression was reduced by 53%, 73%, 80%, and 96% for 3.13, 12.5, 25, and 50 µg ASO-005459, respectively. Similar dose-dependent knockdowns were also observed in the brainstem. In the striatum, SNCA mRNA knockdowns were more variable and less robust compared to the other regions (FIGS. 6A-6C): a 75% and 46% knockdown was observed with 50 µg and 25 µg of ASO-005459, respectively. However, with 12.5 µg and 3.13 µg of ASO-005459, there was no significant reduction in SNCA mRNA expression. Possible explanations for the lower activity observed in the striatum could be due to differences in the ASO levels or the kinetics of SNCA mRNA knockdown.

TABLE 8

ASO-005459 tolerability in 28-day study

| Animal# | Timepoint (day) | Hyperactivity | Vigilance | Motor S&C | Posture/ Breathing | Tremor/ Convulsions | Total Score |
|---|---|---|---|---|---|---|---|
| 26 | 1 | 0 | 0 | 0 | 0 | 0 | 0 |
| 26 | 28 | 0 | 0 | 0 | 0 | 0 | 0 |
| 27 | 1 | 0 | 0 | 0 | 0 | 0 | 0 |
| 27 | 28 | 0 | 0 | 0 | 0 | 0 | 0 |
| 28 | 1 | 0 | 0 | 0 | 0 | 0 | 0 |
| 28 | 28 | 0 | 0 | 0 | 0 | 0 | 0 |
| 29 | 1 | 0 | 0 | 0 | 0 | 0 | 0 |
| 29 | 28 | 0 | 0 | 0 | 0 | 0 | 0 |
| 30 | 1 | 0 | 0 | 0 | 0 | 0 | 0 |
| 30 | 28 | 0 | 0 | 0 | 0 | 0 | 0 |

Figure 7:
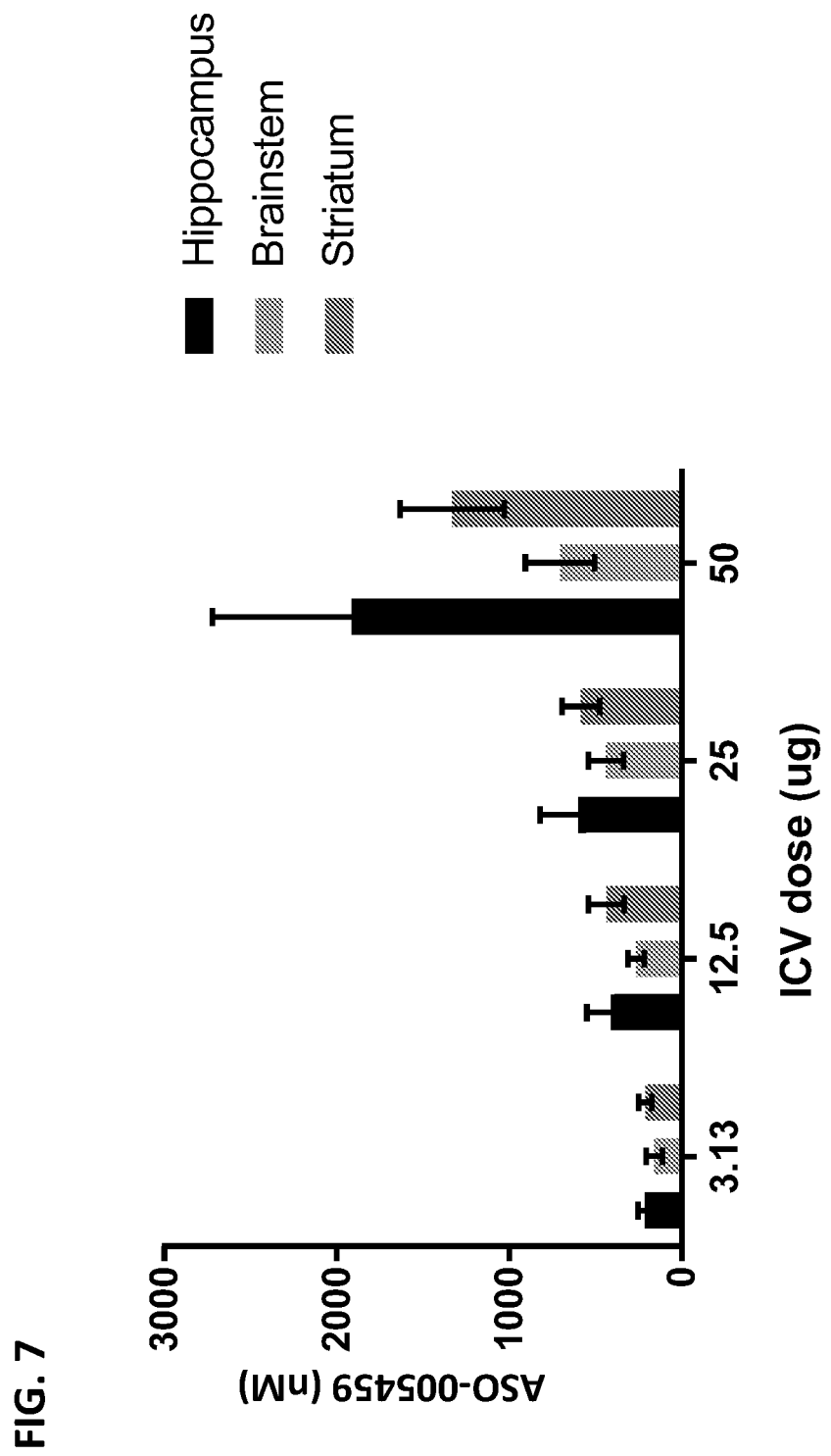
FIG. 7 shows the level of ASO-005459 detected in the hippocampus (black), brainstem (light gray), and the striatum (dark gray) of A53T-PAC mice at 14 days post ASO-005459 treatment. The mice received 3.13 μg, 12.5 μg, 25 μg, or 50 μg of ASO-005459 via ICV administration. Data shown represents the mean±SD from multiple animals (n=5).
Figure 8A:
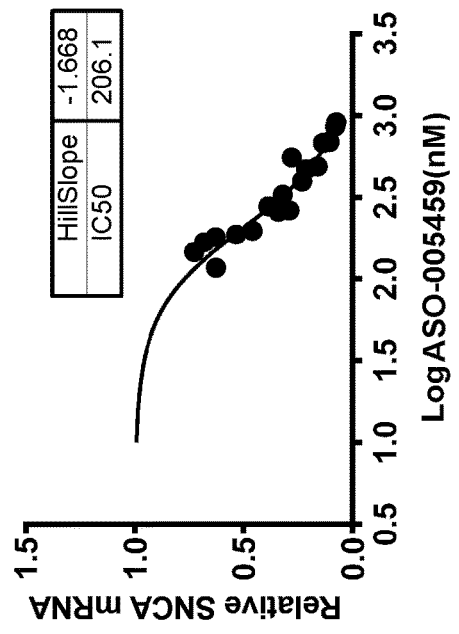
FIGS. 8A, 8B, 8C, and 8D show the relationship between ASO-005459 exposure levels and SNCA mRNA expression in the hippocampus (FIG. 8A), brainstem (FIG. 8B), and striatum (FIG. 8C) of A53T-PAC mice at fourteen days post ASO-005459 treatment.
Figure 8B:
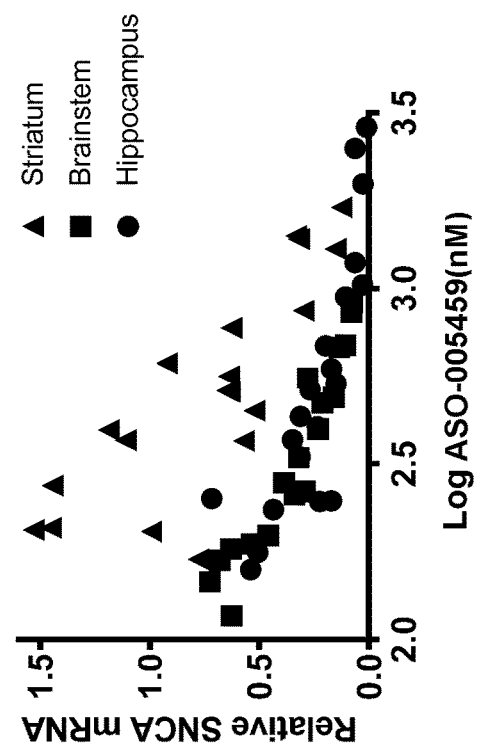
Figure 8C:
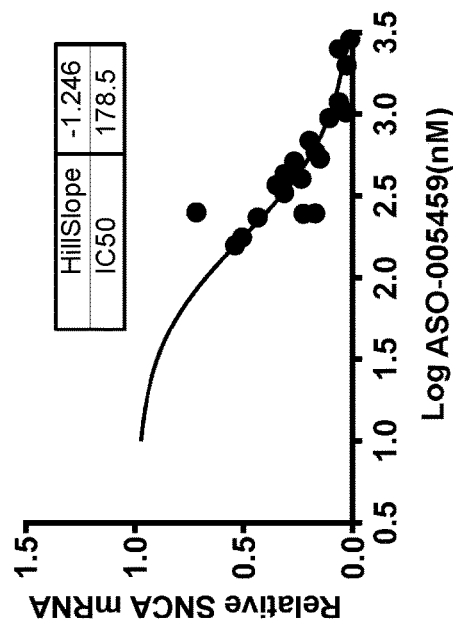
Figure 8D:
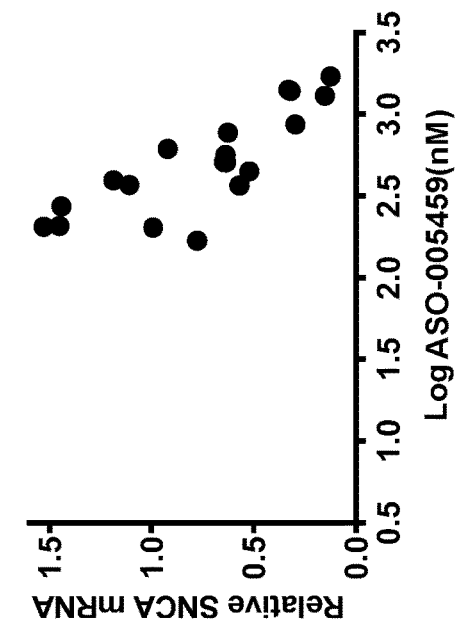

The ASO-005459 levels were measured in all three brain regions of the A53T-PAC mice. As shown in FIG. 7 and Table 9 (below), brain exposures were approximately dose proportional and similar across all three regions, including the striatum. The ASO-005459 exposure-response relationships for the different brain regions are shown in FIGS. 8A-8D. Similar exposure-response relationships were observed in the hippocampus and brainstem with estimated $IC_{50}$s of 179 and 206 nM, respectively. In comparison, the exposure response relationship in the striatum was relatively steep suggesting slower kinetics of SNCA mRNA reduction in that region. See FIG. 8C.

TABLE 9

Summary of ASO-005459 brain exposure in 14-day A53T-PAC study

|   | Dose (µg) | Mean (nM) | SD | Relative to hippo |
|---|---|---|---|---|
| Hippocampus | 3.13 | 214 | 43 |   |
|   | 12.5 | 411 | 140 |   |
|   | 25 | 600 | 223 |   |
|   | 50 | 1916 | 807 |   |
| Brainstem | 3.13 | 160 | 47 | 0.7 |
|   | 12.5 | 266 | 47 | 0.6 |
|   | 25 | 440 | 102 | 0.7 |
|   | 50 | 707 | 202 | 0.4 |
| Striatum | 3.13 | 212 | 38 | 1.0 |
|   | 12.5 | 438 | 103 | 1.1 |
|   | 25 | 586 | 109 | 1.0 |
|   | 50 | 1332 | 302 | 0.7 |

To provide a more extensive dose-response/time course data, ASO-005459 was again administered (0, 12.5, 25, or 50 µg) directly into the cerebral ventricles of A53T-PAC mice by ICV freehand injection. The animals were sacrificed at 24 hours, 3 days, 4, 8, 12, 16, and 20 weeks post dosing and the SNCA mRNA expression in the brain stem and the striatum was assessed.

Figure 9A:
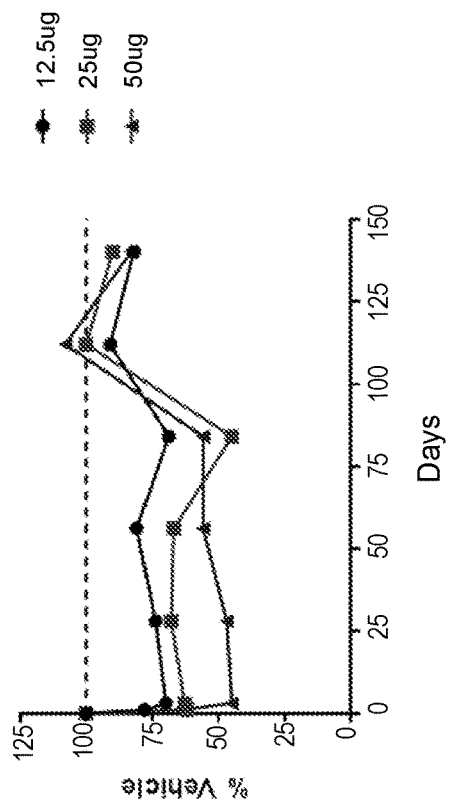
FIGS. 9A and 9B show the dose response curve of the effect of ASO-005459 on SNCA mRNA expression level in A53T-PAC mice. The animals received (via ICV injection) 12.5 μg (circle), 25 μg (box), or 50 μg (triangle) of ASO-005459 and were sacrificed at 24 hours, 3 days, 4, 8, 12, 16, and 20 weeks post-dosing. SNCA mRNA expression levels both in the brain stem (FIG. 9A) and in the striatum (FIG. 9B) were assessed via qRT-PCR and then normalized to the vehicle control. The mean data is shown. The horizontal line marks the reference value of 100% (i.e., value at which the SNCA mRNA expression would be equivalent to expression level observed in the vehicle control group).
Figure 9B:
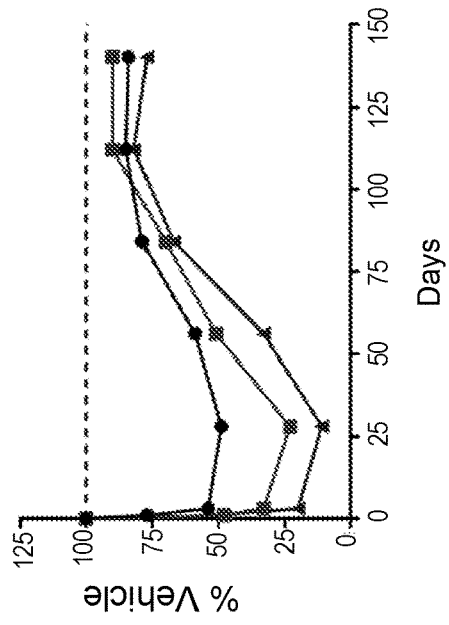
Figure 10B:
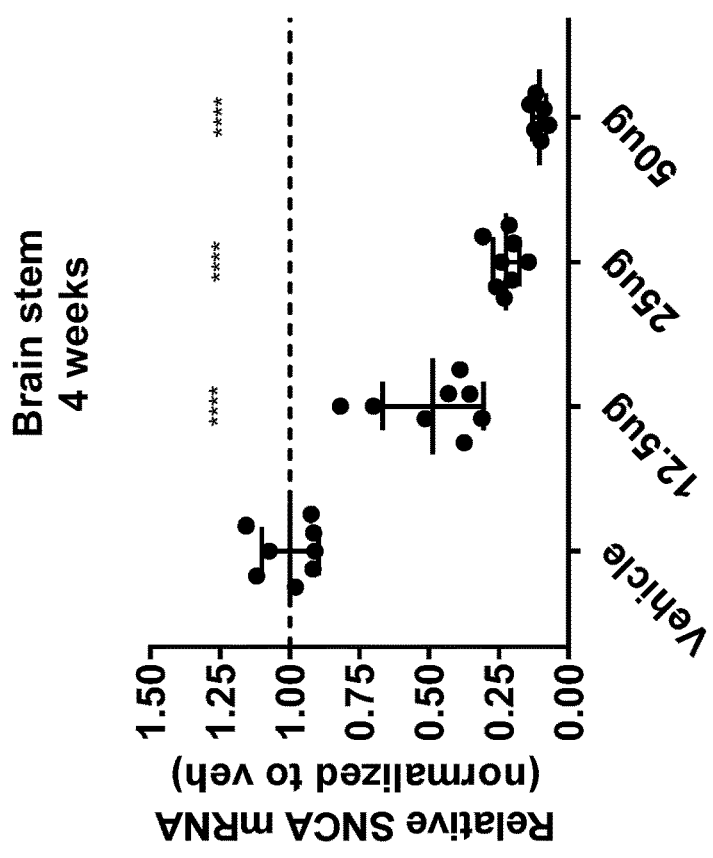
FIGS. 10A and 10B show the effect of ASO-005459 on SNCA mRNA expression level in A53T-PAC mice after 4 weeks post ASO-005459 administration. The animals received either the vehicle control or varying concentration s of ASO-005459 (12.5, 25, or 50 μg). The relative SNCA mRNA expression level (normalized to the vehicle control) are shown for both the brain stem (FIG. 10A) and the striatum (FIG. 10B). Each data point represents an individual animal. The mean±SD from multiple animals is also shown. Statistics shown is based on comparison to the vehicle group using 1-way ANOVA with Dunnett's correction for multiple comparisons. The horizontal line marks the reference value of 1 (i.e., value at which the SNCA mRNA expression would be equivalent to expression level observed in the vehicle control group). *p<0.05, p<0.01, *p<0.001, ****p<0.0001.
Figure 10A:
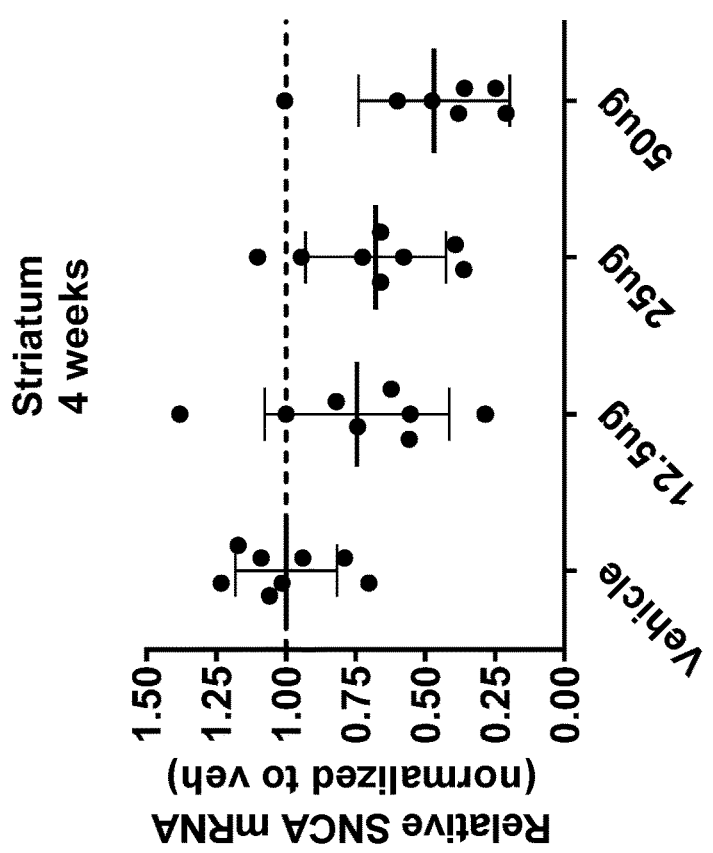

As shown in FIGS. 9A and 9B (and in agreement with the data provided above), administration of ASO-005459 to the A53T-PAC mice resulted in significant reduction of SNCA mRNA expression level (relative to the vehicle control) in both the brain stem and the striatum. The reduction appeared to be both time- and dose-dependent, with peak reduction (~90%) observed in the brain stem with 50 μg ASO-005459 at about 4 weeks post dosing (FIG. 9A). In the striatum, peak reduction (~55%) was observed with 50 μg ASO-005459 at about 3 days post dosing (FIG. 9B). SNCA mRNA expression levels remained significantly reduced compared to the vehicle control at 4 weeks post dosing (FIGS. 10A and 10B) and returned to baseline control by about 16 weeks post-dosing (FIGS. 9A and 9B).

Figure 11A:
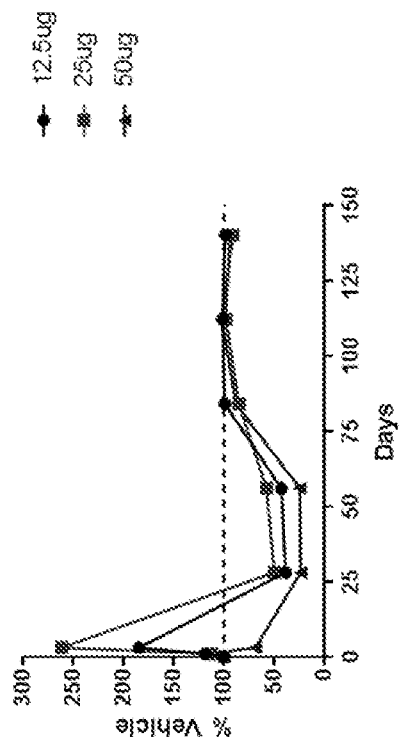
FIGS. 11A and 11B show the dose response curve of the effect of ASO-005459 on SNCA protein expression level in the brain tissues of A53T-PAC mice. The animals received (via ICV injection) 12.5 μg (circle), 25 μg (box), or 50 μg (triangle) of ASO-005459 and were sacrificed at 24 hours, 3 days, 4, 8, 12, 16, and 20 weeks post-dosing. SNCA proteins levels were measured both in the brain stem (FIG. 11A) and in the striatum (FIG. 11B) by ELISA and then normalized to the vehicle control. The mean data is shown. The horizontal line marks the reference value of 100% (i.e., value at which the SNCA mRNA expression would be equivalent to expression level observed in the vehicle control group).
Figure 11B:
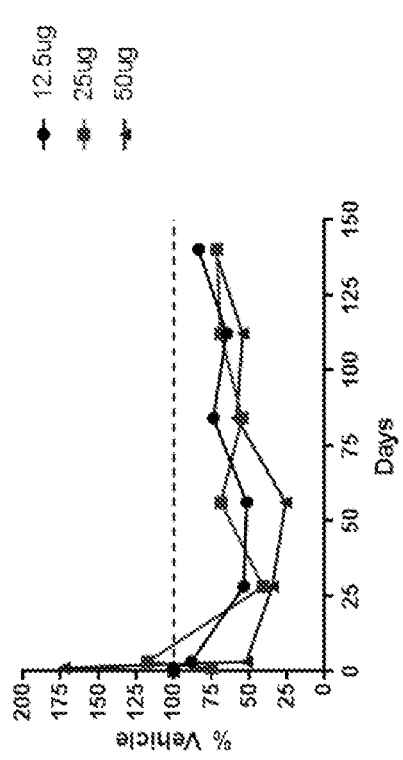
Figure 12A:
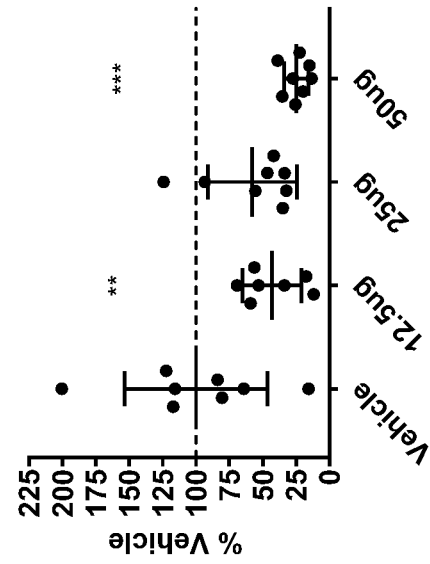
FIGS. 12A and 12B show the effect of ASO-005459 on SNCA protein expression level in A53T-PAC mice at 8 weeks post ASO-005459 administration. The animals received either the vehicle control or varying concentrations of ASO-005459 (12.5, 25, or 50 μg). The relative SNCA protein expression levels (normalized to the vehicle control) are shown for both the brain stem (FIG. 12A) and the striatum (FIG. 12B). Each data point represents an individual animal. The horizontal line marks the reference value of 100% (i.e., value at which the SNCA mRNA expression would be equivalent to expression level observed in the vehicle control group). The mean±SD from multiple animals is also shown. Statistics shown is based on comparison to the vehicle group using 1-way ANOVA with Dunnett's correction for multiple comparisons.
Figure 12B:
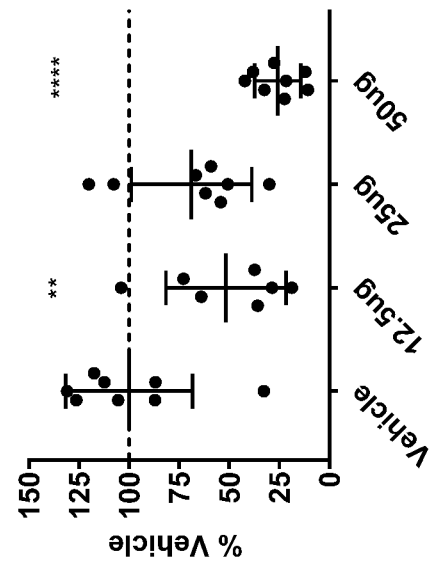

As shown in FIGS. 11A and 11B, administration of ASO-005459 to the animals also resulted in a time- and dose-dependent reduction in the SNCA protein level in both the brain stem and the striatum brain tissue. Peak reduction (~75%) was observed in the brain stem with a dose of 50 μg at 8 weeks post dosing (FIG. 11A). For the striatum brain tissue, peak reduction (~75%) was also observed with the 50 μg dose but at 4 weeks post dosing (FIG. 11B). Expression levels for the individual mice at 8 weeks post dosing are provided in FIGS. 12A (brain stem) and 12B (striatum). While SNCA protein level returned close to baseline by about 12 weeks post dosing in the striatum, expression level was still significantly reduced (~25%) in the brain stem as far out as 16 weeks post-dosing.

Example 9: Analysis of In Vivo Activity and Tolerability of SNCA-Targeted Antisense Oligonucleotides (ASOs) in Cynomolgous Monkeys To further evaluate the ASO activity and tolerability in vivo, an intrathecal ported Cynomolgus monkey model (Cyno IT) was developed. This model enables the evaluation of ASO-005459-mediated knockdown of SNCA as well as knockdown of the potential 1-basepair mismatch off-targets PROS1 and IKZF3. The ASO-005459 target sites in SNCA, PROS1, and IKZF3 are completely conserved between human and cyno.

As described above in Example 6, each animal was implanted with an intrathecal cerebrospinal fluid (CSF) catheter entering at the L3 or L4 vertebrae. ASO-005459 was dissolved in saline and administered to the animals (8 mg/animal), infused over 4.5 min using the IT port (2 animals per dose group). Animals were then euthanized at 24 hours and 3 days post dosing, when the tissues were harvested for analysis of the ASO exposure and activity. Brain regions analyzed included medulla (Med), pons (V-Pons), midbrain (V-MB), cerebellum (CBL), caudate-putamen (left and right) (CauP), hippocampus (left and right) (Hip), frontal cortex (left and right) (FrC), temporal cortex (left and right) (TeC), parietal cortex (left and right) (PaC), occipital cortex (left and right) (Occ), and cortical white matter (WM). Additionally, spinal cord was sampled at the cervical (CSC), thoracic (TSC), and lumbar (LSC) regions. Samples were also collected from liver, kidney, heart, trigeminal nuclei, tibial nerve, and aorta to examine off-target pharmacology in those areas.

As was observed in mice, ASO-005459 was well tolerated in cyno with no adverse effects being observed (data not shown). And as shown in Table 10 below, the administration of ASO-005459 exhibited robust knockdown of SNCA mRNA in various regions of the cyno brain.

TABLE 10

Effect of ASO-005459 on brain SNCA mRNA levels in cyno brain

| ASO No. | Dose (mg) | Timepoint (weeks) | Med | CBL | FrC | PaC | CauP | TeC | Occ | Hip | V-MB | V-Pons | CSC | TSC | LSC | WM |
|---|---|---|---|---|---|---|---|---|---|---|---|---|---|---|---|---|
| ASO-005459 | 8 | 24 hours | 174 | 140 | 146 | | 149 | | | | | 137 | | | 73 | |
| | 8 | 24 hours | 129 | 108 | 138 | | 133 | | | | | 145 | | | 90 | |
| | 8 | 3 days | 162 | 69 | 69 | | 112 | | | | | 62 | | | 19 | |
| | 8 | 3 days | 127 | 67 | 72 | | 114 | | | | | 87 | | | 31 | |
| | 2 | 2 | 133 | 140 | 109 | | 161 | | | | | 104 | | | 21 | |
| | 2 | 2 | 117 | 127 | 100 | | 126 | | | | | 180 | | | 111 | |
| | 4 | 2 | 62 | 86 | 22 | | 116 | | | | | 49 | | | 4 | |
| | 4 | 2 | 81 | 72 | 50 | | 145 | | | | | 97 | | | 13 | |
| | 8 | 2 | 31 | 97 | 7 | | 124 | | | | | 66 | | | 14 | |
| | 8 | 2 | 30 | 38 | 15 | 26 | 75 | 12 | 29 | 29 | 86 | 29 | 13 | 6 | 2 | 79 |
| | 8 | 4 | 26 | 50 | 4 | 12 | 53 | 3 | 13 | 9 | 24 | 21 | 4 | 6 | 4 | 87 |
| | 8 | 4 | 38 | 61 | 9 | | 120 | | | | | 30 | | | 10 | |
| | 8 | 8 | 121 | 85 | 40 | | 98 | | | | | 78 | | | 5 | |
| | 8 | 8 | 93 | 52 | 14 | | 61 | | | | | 36 | | | 11 | |
| | 8 | 13 | 30 | 63 | 8 | | 81 | | | | | 27 | | | 1 | |
| | 8 | 13 | 25 | 28 | 8 | | 49 | | | | | 22 | | | 1 | |
| | 8 | 20 | 40 | 38 | 35 | | 76 | | | | | 63 | | | 9 | |
| | 8 | 20 | 22 | 52 | 35 | | 76 | | | | | 26 | | | 11 | |

Figure 13A:
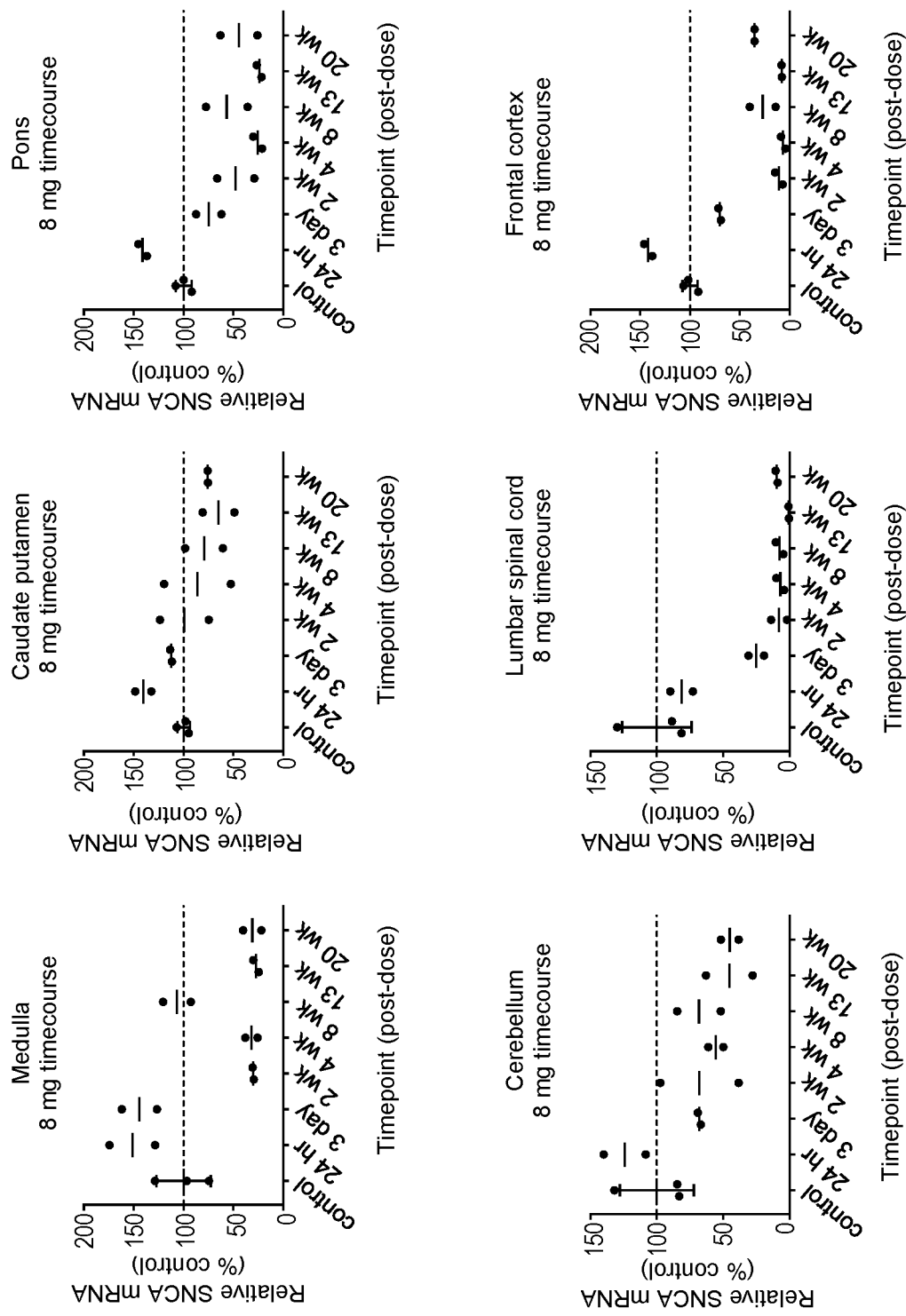
FIGS. 13A and 13B show the kinetics of SNCA mRNA and SNCA protein expression levels in cyno monkeys after ASO-005459 administration. Each of the animals received either the vehicle control or ASO-005459 (8 mg) and then were sacrificed at 24 hours, 3 days, 2, 4, 8, 13, or 20 weeks post-dosing. At each time point, the expression levels of SNCA mRNA (FIG. 13A) and SNCA protein (FIG. 13B) were assessed in the following tissues: medulla (top left panel), caudate putamen (top middle panel), pons (top right panel), cerebellum (bottom left panel), lumbar spinal cord (bottom middle panel), and frontal cortex (bottom right panel). The expression levels are shown as a percentage of the vehicle control. Both the data for the individual animals and the mean are shown. The horizontal line marks the reference value of 100% (i.e., value at which the SNCA mRNA expression would be equivalent to expression level observed in the vehicle control group).
Figure 13B:
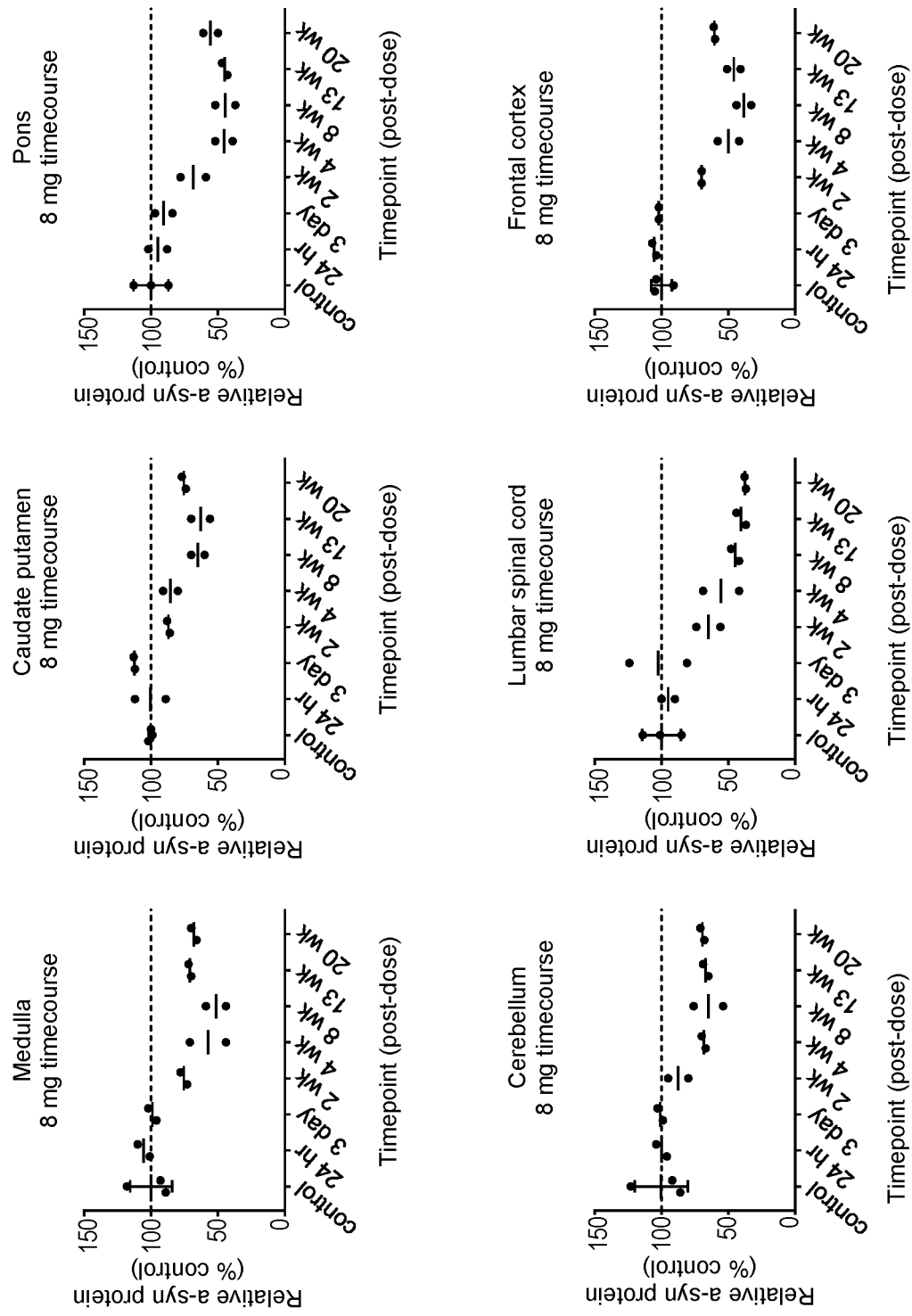

To further characterize the reduction of SNCA mRNA described above, cyno monkeys were dosed with ASO-005459 (8 mg total per animal) and sacrificed at 24 hour, 3 days, 2, 4, 8, 13, or 20 weeks post-dosing to assess the SNCA mRNA expression level in the different tissues. As shown in FIG. 13A, peak reduction was observed between 2 weeks and 13 weeks post-dosing. Peak reductions of 70%, 65%, 75%, 35%, 94% and 99% were observed in the medulla, cerebellum, pons, caudate-putamen, frontal cortex and lumbar spinal cord, respectively. This reduction in SNCA mRNA expression level also correlated with a time-dependent reduction in the SNCA protein expression level (FIG. 13B).

Figure 14A:
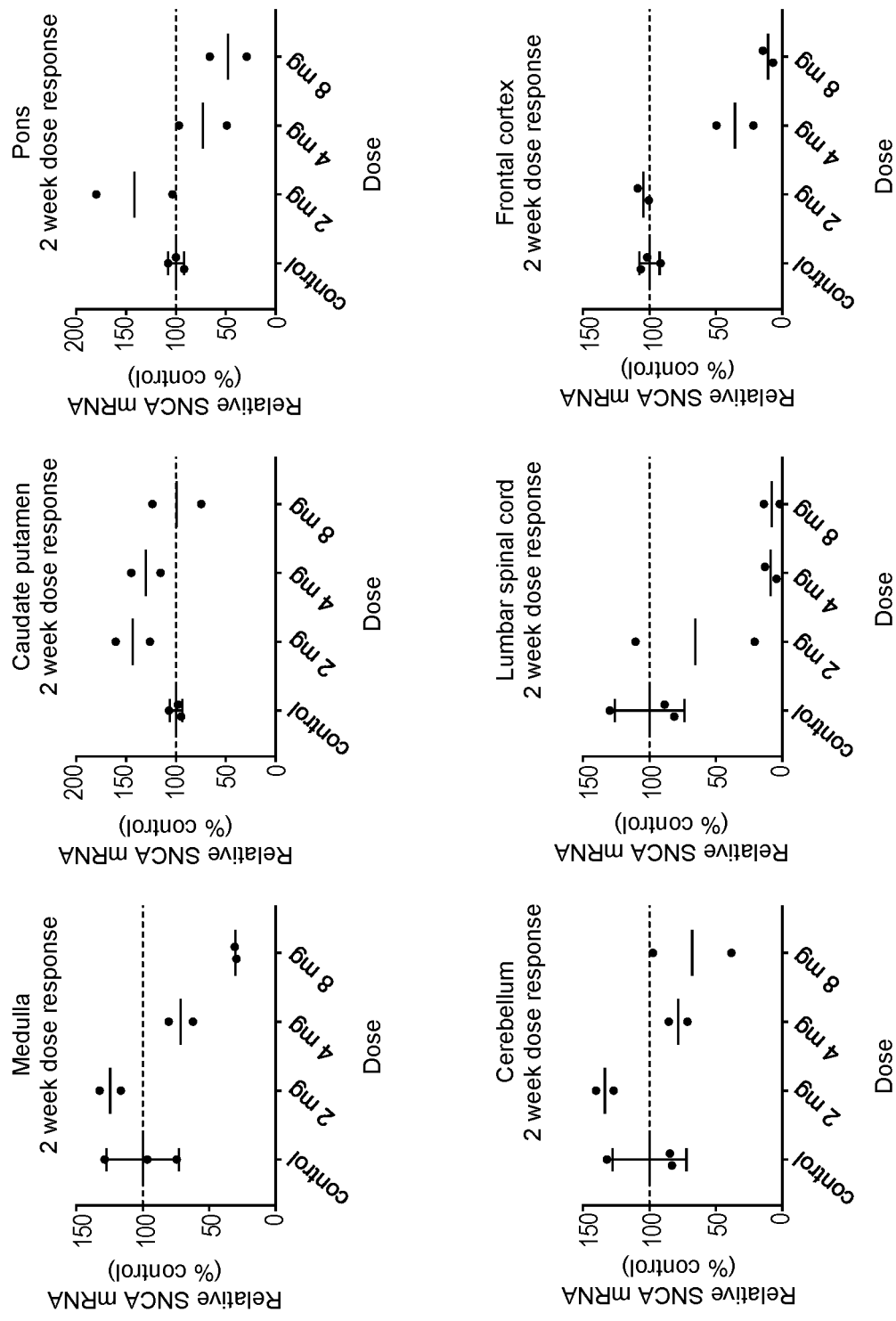
FIGS. 14A and 14B show the relative expression level (as percentage of the vehicle control) for both the SNCA mRNA (FIG. 14A) and SNCA protein (FIG. 14B) in cyno monkeys at 2 weeks post ASO-005459 administration. The animals received either the vehicle control or varying concentrations of the ASO-005459 (2, 4, or 8 mg). The expression levels were assessed in the following tissues: medulla (top left panel), caudate putamen (top middle panel), pons (top right panel), cerebellum (bottom left panel), lumbar spinal cord (bottom middle panel), and frontal cortex (bottom right panel). The expression levels are shown as a percentage of the vehicle control. Both the data for the individual animals and the mean are shown. The horizontal line marks the reference value of 100% (i.e., value at which the SNCA mRNA expression would be equivalent to expression level observed in the vehicle control group).
Figure 14B:
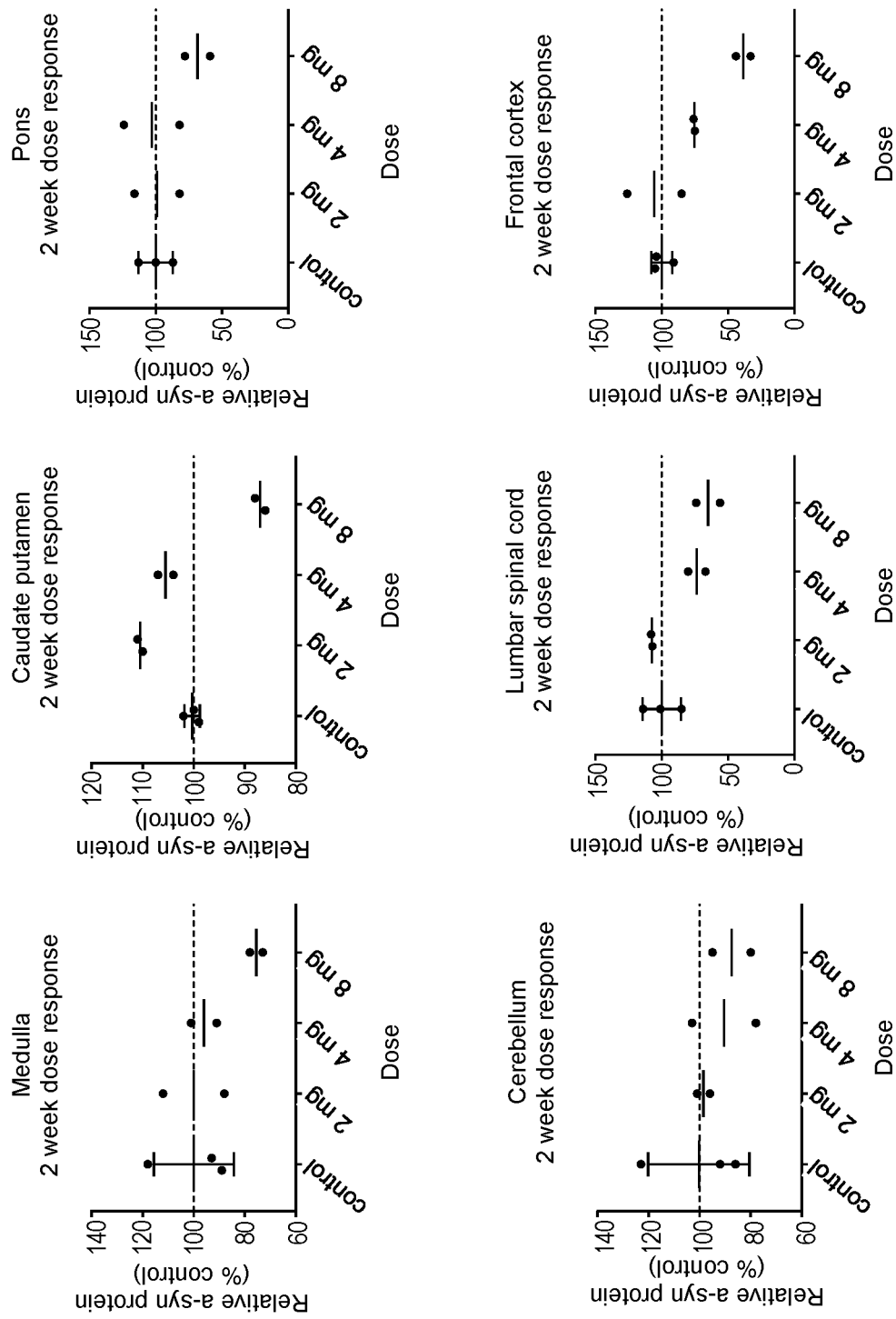

Next, to assess whether the reduction in expression level in the cyno monkeys was also dependent on the dose, the animals received 2, 4, or 8 mg of ASO-005459 and then, were sacrificed at 2 weeks post-dosing. As shown in FIGS. 14A and 14B, the reduction in both the SNCA mRNA and the SNCA protein expression levels was also dependent on the dose, with the greatest reduction observed with 8 mg of ASO-005459.

The results presented here demonstrate that ASO-005459 is potent and selective for reducing SNCA mRNA and that ASO-005459 is well tolerated in neurons and in preclinical species in vivo. Moreover, results from the A53T-PAC neurons confirm that ASO-005459-mediated reductions of mRNA result in reductions of SNCA protein levels in vitro and in vivo. In addition, results in A53T-PAC mice and cyno monkeys demonstrate that ASO-005459 reduces SNCA mRNA and SNCA protein in brain at doses that are well tolerated. Taken together, these findings support the continued development of ASO-005459 as a disease-modifying therapeutic for the treatment of synucleinopathies.

This PCT application claims priority benefit of U.S. Provisional Application No. 62/616,937, filed Jan. 12, 2018, which is incorporated herein by reference in its entirety.

What is claimed:

1. An antisense oligonucleotide (ASO) comprising the contiguous nucleotide sequence of AtTcctttacaccACAC (SEQ ID NO: 4), wherein the upper letter is beta-D-oxy-LNA and the lower letter is DNA.

2. The ASO of claim 1, which comprises an internucleotide linkage selected from the group consisting of a phosphodiester linkage, a phosphotriester linkage, a methylphosphonate linkage, a phosphoramidate linkage, a phosphorothioate linkage, and combinations thereof.

3. The ASO of claim 2, wherein the internucleotide linkage is a phosphorothioate linkage.

4. The ASO of claim 1, wherein the contiguous nucleotide sequence is OxyAs DNAts OxyTs DNAcs DNAcs DNAts DNAts DNAts DNAas DNAcs DNAas DNAcs DNAcs OxyAs OxyMCs OxyAs OxyMC, wherein the OxyA, OxyT, and Oxy MC are adenine beta D-oxy-LNA, thymine beta D-oxy-LNA, and methyl cytosine beta D-oxy-LNA, respectively, wherein DNAt, DNAc, and DNAa are thymine DNA, cytosine DNA, and adenine DNA, respectively, and wherein s is a phosphorothioate linkage between two nucleotides.

5. The ASO of claim 1, comprising the structure:

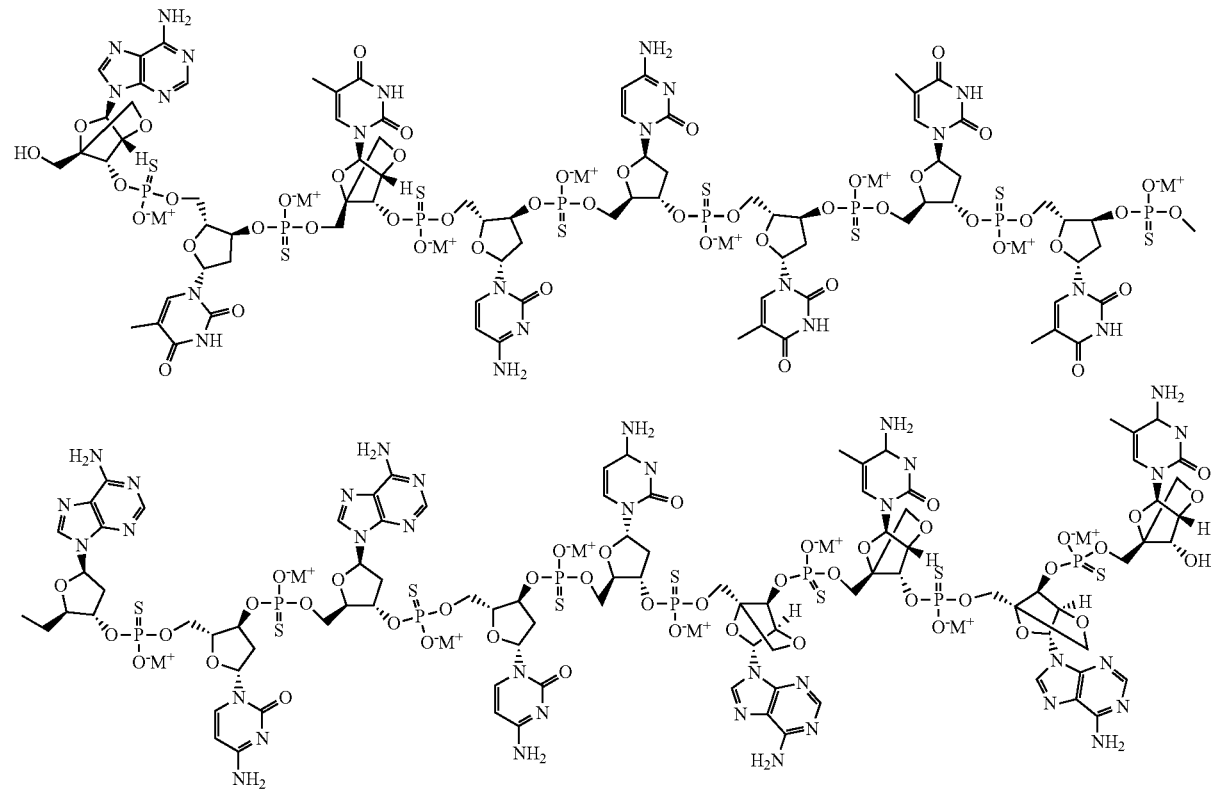

wherein M⁺ is a counterion.

6. The ASO of claim 5, wherein the counterion is selected from the group consisting of $H^+$, $Na^+$, $NH_4^\pm$, and any combination thereof.

7. The ASO of claim 6, wherein the counterion is $Na^+$.

8. A conjugate comprising the ASO of claim 1, wherein the ASO is covalently attached to at least one non-nucleotide or non-polynucleotide moiety.

9. The conjugate of claim 8, wherein the non-nucleotide or non-polynucleotide moiety comprises a protein, a fatty acid chain, a sugar residue, a glycoprotein, a polymer, or any combinations thereof.

10. A pharmaceutical composition comprising the ASO of claim 1 and a pharmaceutically acceptable carrier.

11. The composition of claim 10, which further comprises a therapeutic agent.

12. The composition of claim 11, wherein the therapeutic agent is an alpha-synuclein antagonist.

13. A kit comprising the ASO of claim 1 and instructions for use.

14. A method of inhibiting or reducing expression of SNCA mRNA and/or SNCA protein in a cell, the method comprising administering the ASO of claim 1 to the cell expressing SNCA mRNA and/or SNCA protein, wherein the expression of SNCA mRNA and/or SNCA protein in the cell is inhibited or reduced after the administration.

15. A method for treating a synucleinopathy in a subject in need thereof, comprising administering an effective amount of the ASO of claim 1 to the subject.

16. The method of claim 15, wherein the synucleinopathy is selected from the group consisting of Parkinson's disease, Parkinson's Disease Dementia (PDD), multiple system atrophy, dementia with Lewy bodies, and any combinations thereof.

17. A pharmaceutical composition comprising the ASO of claim 3 and a pharmaceutically acceptable carrier.

18. A pharmaceutical composition comprising the ASO of claim 4 and a pharmaceutically acceptable carrier.

19. A pharmaceutical composition comprising the ASO of claim 5 and a pharmaceutically acceptable carrier.

20. A pharmaceutical composition comprising the ASO of claim 7 and a pharmaceutically acceptable carrier.

\* \* \* \* \*

UNITED STATES PATENT AND TRADEMARK OFFICE
CERTIFICATE OF CORRECTION

PATENT NO. : 11,447,775 B2  
APPLICATION NO. : 16/961624  
DATED : September 20, 2022  
INVENTOR(S) : Richard E. Olson et al.

Page 1 of 1

It is certified that error appears in the above-identified patent and that said Letters Patent is hereby corrected as shown below:

In the Claims

In Column 48, Claim 4, Line 26, delete "Oxy MC" and insert --OxyMC--, therefor.

In Columns 48-49, Claim 5, Line 34, delete

"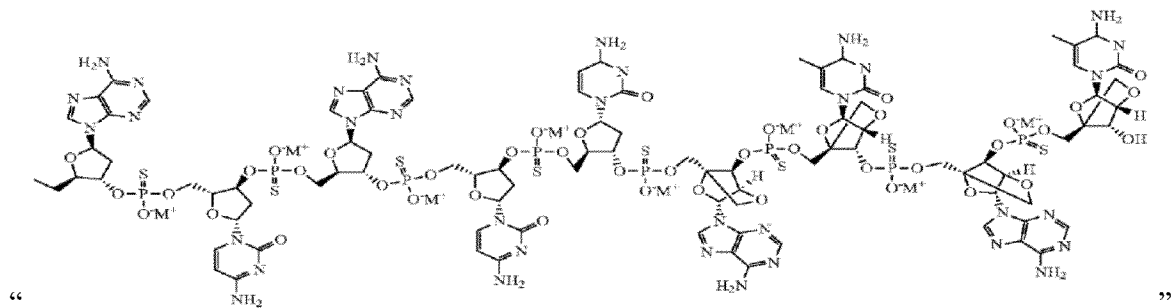"

and insert

--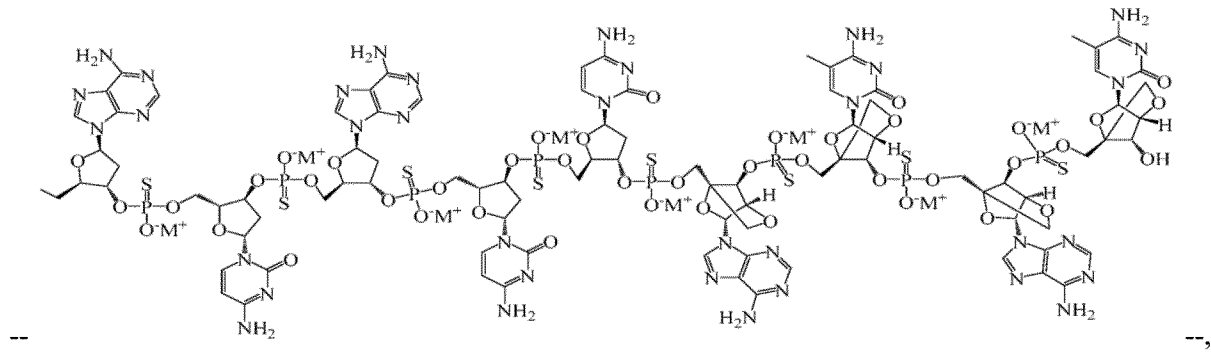--, therefor.

In Column 49, Claim 6, Line 2, delete "$NH_4^{\pm}$," and insert --$NH_4^+$,--, therefor.

Signed and Sealed this  
Twenty-first Day of March, 2023

Katherine Kelly Vidal  
*Director of the United States Patent and Trademark Office*

SEQUENCE LISTING

```
<160> NUMBER OF SEQ ID NOS: 10

<210> SEQ ID NO 1
<211> LENGTH: 2400
<212> TYPE: DNA
<213> ORGANISM: Homo sapiens

<400> SEQUENCE: 1
gagataggga cgaggagcac gctgcaggga aagcagcgag cgccgggaga ggggcgggca      60
gaagcgctga caaatcagcg gtggggcgg agagccgagg agaaggagaa ggaggaggac     120
taggaggagg aggacggcga cgaccagaag gggcccaaga gaggggcga gcgaccgagc     180 gccgcgacgc ggaagtgagg tgcgtgcggg ctgcagcgca gacccggcc cggcccctcc     240 gagagcgtcc tgggcgctcc ctcacgcctt gccttcaagc cttctgcctt tccaccctcg     300
tgagcggaga actgggagtg gccattcgac gacaggttag cgggtttgcc tcccactccc     360
ccagcctcgc gtcgccggct cacagcggcc tcctctgggg acagtccccc ccgggtgccg     420
cctccgccct tcctgtgcgc tccttttcct tcttctttcc tattaaatat tatttgggaa     480
ttgtttaaat ttttttttta aaaaagaga gaggcgggga ggagtcggag ttgtggagaa     540
gcagagggac tcaggtaagt acctgtggat ctaaacgggc gtctttggaa atcctggaga     600
acgccggatg ggagacgaat ggtcgtgggc accgggaggg ggtggtgctg ccatgaggac     660
ccgctgggcc aggtctctgg gaggtgagta cttgtccctt tggggagcct aaggaaagag     720
acttgacctg gctttcgtcc tgcttctgat attcccttct ccacaagggc tgagagatta     780
ggctgcttct ccgggatccg cttttccccg ggaaacgcga ggatgctcca tggagcgtga     840
gcatccaact tttctctcac ataaaatctg tctgcccgct ctcttggttt ttctctgtaa     900
agtaagcaag ctgcgtttgg caaataatga aatggaagtg caaggaggcc aagtcaacag     960
gtggtaacgg gttaacaagt gctggcgcgg ggtccgctag ggtggaggct gagaacgccc    1020
cctcgggtgg ctggcgcggg gttggagacg gcccgcgagt gtgagcggcg cctgctcagg    1080
gtagatagct gagggcgggg gtggatgttg gatggattag aaccatcaca cttgggcctg    1140
ctgtttgcct gagtttgaac cacacccga gtgagcagtt agttctgttg cctacgcctt    1200
tccaccatca acctgttagc cttcttctgg gattcatgtt aaggataccc ctgaccctaa    1260
gcctccagct tccatgcttc taactcatac tgttacccct tagaccccgg gaatttaaaa    1320 aagggttaa tcttttcatg caactccact tctgaaatgc agtaataaca actcagagga    1380
ttcatcctaa tccgtggtta ggtggctaga cttttactag ccaagatgga tgggagatgc    1440
taaattttta atgccagagc taaaaatgtc tgctttgtcc aatggttaaa tgagtgtaca    1500
cttaaaagag tctcacactt tggagggttt ctcatgattt ttcagtgttt tttgttatt     1560 tttccccgaa agttctcatt caaagtgtat tttatgtttt ccagtgtggt gtaaaggaat    1620
tcattagcca tggatgtatt catgaaagga cttcaaagg ccaaggaggg agttgtggct    1680
gctgctgaga aaaccaaaca gggtgtggca gaagcagcag gaaagacaaa agagggtgtt    1740
```

-continued

| | |
|---|---|
| ctctatgtag gtaggtaaac cccaaatgtc agtttggtgc ttgttcatga gtgatgggtt | 1800 |
| aggataatca atactctaaa tgctggtagt tctctctctt gattcatttt tgcatcattg | 1860 |
| cttgtcaaaa aggtggactg agtcagaggt atgtgtaggt aggtgaatgt gaacgtgtgt | 1920 |
| atttgagcta atagtaaaaa atgcgactgt ttgcttttcc agattttttaa ttttgcccta | 1980 |
| atatttatga cttttttaaaa atgaatgttt ctgtacctac ataattctat ttcagagaac | 2040 |
| agttttaaaa actcatagtc ttttaaaaaa taatcaagaa tattcttaag aatcaaaatc | 2100 |
| attgatggat ctgtgatttc ttttaccatc atgaaaaatg tttgtcaatt ttaatccatt | 2160 |
| ctgattttta aaatatgact ttgatatgcc cctgtgatgt gtataaagag acctatttgt | 2220 |
| ggccctaaaa tggaaagaac agattagtct ttgatagagt tacttcatgt gatcatttgg | 2280 |
| tctctgtgaa cactgaggac agagaaaagt gcttgagggc tgctactaat ctctcagaaa | 2340 |
| catttgtata gttcatccat caaatgacac acatactaaa agaataaaga aattgatgct | 2400 |

<210> SEQ ID NO 2
<211> LENGTH: 3215
<212> TYPE: DNA
<213> ORGANISM: Homo sapiens

<400> SEQUENCE: 2

| | |
|---|---|
| aggagaagga gaaggaggag gactaggagg aggaggacgg cgacgaccag aaggggccca | 60 |
| agagaggggg cgagcgaccg agcgccgcga cgcggaagtg aggtgcgtgc gggctgcagc | 120 |
| gcagaccccg gccggcccc tccgagagcg tcctgggcgc tccctcacgc cttgccttca | 180 |
| agccttctgc ctttccaccc tcgtgagcgg agaactggga gtggccattc gacgacagtg | 240 |
| tggtgtaaag gaattcatta gccatggatg tattcatgaa aggactttca aaggccaagg | 300 |
| agggagttgt ggctgctgct gagaaaacca aacagggtgt ggcagaagca gcaggaaaga | 360 |
| caaaagaggg tgttctctat gtaggctcca aaaccaagga gggagtggtg catggtgtgg | 420 |
| caacagtggc tgagaagacc aaagagcaag tgacaaatgt tggaggagca gtggtgacgg | 480 |
| gtgtgacagc agtagcccag aagacagtgg agggagcagg gagcattgca gcagccactg | 540 |
| gctttgtcaa aaaggaccag ttgggcaaga tgaagaagg agccccacag gaaggaattc | 600 |
| tggaagatat gcctgtggat cctgacaatg aggcttatga aatgccttct gaggaagggt | 660 |
| atcaagacta cgaacctgaa gcctaagaaa tatctttgct cccagtttct tgagatctgc | 720 |
| tgacagatgt tccatcctgt acaagtgctc agttccaatg tgcccagtca tgacatttct | 780 |
| caaagttttt acagtgtatc tcgaagtctt ccatcagcag tgattgaagt atctgtacct | 840 |
| gcccccactc agcatttcgg tgcttccctt tcactgaagt gaatacatgg tagcagggtc | 900 |
| tttgtgtgct gtggatttg tggcttcaat ctacgatgtt aaaacaaatt aaaaacacct | 960 |
| aagtgactac cacttatttc taaatcctca ctattttttt gttgctgttg ttcagaagtt | 1020 |
| gttagtgatt tgctatcata tattataaga tttttaggtg tcttttaatg atactgtcta | 1080 |
| agaataatga cgtattgtga aatttgttaa tatatataat acttaaaaat atgtgagcat | 1140 |
| gaaactatgc acctataaat actaaatatg aaatttacc attttgcgat gtgttttatt | 1200 |
| cacttgtgtt tgtatataaa tggtgagaat taaaataaaa cgttatctca ttgcaaaaat | 1260 |
| atttattttt tatcccatct cactttaata ataaaaatca tgcttataag caacatgaat | 1320 |
| taagaactga cacaaaggac aaaaatataa agttattaat agcccatttga agaaggagga | 1380 |
| attttagaag aggtagagaa aatggaacat taaccctaca ctcggaattc cctgaagcaa | 1440 |

```
cactgccaga agtgtgtttt ggtatgcact ggttccttaa gtggctgtga ttaattattg    1500
aaagtggggt gttgaagacc ccaactacta ttgtagagtg gtctatttct cccttcaatc    1560
ctgtcaatgt ttgctttacg tattttgggg aactgttgtt tgatgtgtat gtgtttataa    1620
ttgttataca ttttttaattg agccttttat taacatatat tgttattttt gtctcgaaat    1680
aattttttag ttaaaatcta ttttgtctga tattggtgtg aatgctgtac ctttctgaca    1740
ataaataata ttcgaccatg aataaaaaaa aaaaaaaagt gggttcccgg gaactaagca    1800
gtgtagaaga tgattttgac tacaccctcc ttagagagcc ataagacaca ttagcacata    1860
ttagcacatt caaggctctg agagaatgtg gttaactttg tttaactcag cattcctcac    1920
tttttttttt taatcatcag aaattctctc tctctctctc tcttttttctc tcgctctctt    1980 tttttttttt ttttttacagg aaatgccttt aaacatcgtt ggaactacca gagtcacctt    2040
aaaggagatc aattctctag actgataaaa atttcatggc ctcctttaaa tgttgccaaa    2100
tatatgaatt ctaggatttt tccttaggaa aggttttttct ctttcaggga agatctatta    2160
actccccatg ggtgctgaaa ataaacttga tggtgaaaaa ctctgtataa attaatttaa    2220
aaattatttg gtttctcttt ttaattattc tggggcatag tcatttctaa aagtcactag    2280
tagaaagtat aatttcaaga cagaatattc tagacatgct agcagtttat atgtattcat    2340
gagtaatgtg atatatattg ggcgctggtg aggaaggaag gaggaatgag tgactataag    2400
gatggttacc atagaaactt cctttttttac ctaattgaag agagactact acagagtgct    2460
aagctgcatg tgtcatctta cactagagag aaatggtaag tttcttgttt tatttaagtt    2520
atgtttaagc aaggaaagga tttgttattg aacagtatat ttcaggaagg ttagaaagtg    2580
gcggttagga tatatttttaa atctacctaa agcagcatat tttaaaaatt taaaagtatt    2640
ggtattaaat taagaaatag aggacagaac tagactgata gcagtgacct agaacaattt    2700
gagattagga aagttgtgac catgaattta aggatttatg tggatacaaa ttctcccttta    2760 aagtgtttct tcccttaata tttatctgac ggtaattttt gagcagtgaa ttactttata    2820
tatcttaata gtttatttgg gaccaaacac ttaaacaaaa agttctttaa gtcatataag    2880
ccttttcagg aagcttgtct catattcact cccgagacat tcacctgcca agtggcctga    2940
ggatcaatcc agtcctaggt ttattttgca gacttacatt ctcccaagtt attcagcctc    3000
atatgactcc acggtcggct ttaccaaaac agttcagagt gcactttggc acacaattgg    3060
gaacagaaca atctaatgtg tggtttggta ttccaagtgg ggtcttttttc agaatctctg    3120 cactagtgtg agatgcaaac atgtttcctc atctttctgg cttatccagt atgtagctat    3180
ttgtgacata ataaatatat acatatatga aaata                              3215
```

<210> SEQ ID NO 3
<211> LENGTH: 140
<212> TYPE: PRT
<213> ORGANISM: Homo sapiens

<400> SEQUENCE: 3

```
Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60
```

```
Asn Val Gly Gly Ala Val Val Thr Gly Val Thr Ala Val Ala Gln Lys
 65                  70                  75                  80

Thr Val Glu Gly Ala Gly Ser Ile Ala Ala Ala Thr Gly Phe Val Lys
                 85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 4
<211> LENGTH: 17
<212> TYPE: DNA
<213> ORGANISM: Artificial Sequence
<220> FEATURE:
<223> OTHER INFORMATION: Antisense Oligonucleotides

<400> SEQUENCE: 4
attcctttac accacac                                                    17

<210> SEQ ID NO 5
<211> LENGTH: 15
<212> TYPE: DNA
<213> ORGANISM: Artificial Sequence
<220> FEATURE:
<223> OTHER INFORMATION: Antisense Oligonucleotides

<400> SEQUENCE: 5
tctgtcttgg ctttg                                                      15

<210> SEQ ID NO 6
<211> LENGTH: 16
<212> TYPE: DNA
<213> ORGANISM: Artificial Sequence
<220> FEATURE:
<223> OTHER INFORMATION: Antisense Oligonucleotides

<400> SEQUENCE: 6
agaaataagt ggtagt                                                     16

<210> SEQ ID NO 7
<211> LENGTH: 20
<212> TYPE: DNA
<213> ORGANISM: Artificial Sequence
<220> FEATURE:
<223> OTHER INFORMATION: Antisense Oligonucleotides

<400> SEQUENCE: 7
ccaaatctta taataactac                                                 20

<210> SEQ ID NO 8
<211> LENGTH: 16
<212> TYPE: DNA
<213> ORGANISM: Artificial Sequence
<220> FEATURE:
<223> OTHER INFORMATION: Antisense Oligonucleotides

<400> SEQUENCE: 8
ttcctttaca ccacac                                                     16

<210> SEQ ID NO 9
<211> LENGTH: 16
```

```
<212> TYPE: DNA
<213> ORGANISM: Artificial Sequence
<220> FEATURE:
<223> OTHER INFORMATION: Antisense Oligonucleotides

<400> SEQUENCE: 9
ggtgaggttt ggtaga                                              16

<210> SEQ ID NO 10
<211> LENGTH: 18
<212> TYPE: DNA
<213> ORGANISM: Artificial Sequence
<220> FEATURE:
<223> OTHER INFORMATION: Antisense Oligonucleotides

<400> SEQUENCE: 10
ggtgaggttt ggtagaag                                            18
```